US008823490B2

(12) United States Patent
Libbus et al.

(10) Patent No.: US 8,823,490 B2
(45) Date of Patent: Sep. 2, 2014

(54) PATIENT MONITORING SYSTEMS AND METHODS

(75) Inventors: Imad Libbus, St. Paul, MN (US); Badri Amurthur, Los Gatos, CA (US); Yatheendhar D. Manicka, Woodbury, MN (US); Scott T. Mazar, Woodbury, MN (US); Matt Merkert, Redwood City, CA (US); Brett A. Landrum, Shoreview, MN (US)

(73) Assignee: Corventis, Inc., St. Paul, MN (US)

( * ) Notice: Subject to any disclaimer, the term of this patent is extended or adjusted under 35 U.S.C. 154(b) by 403 days.

(21) Appl. No.: 13/139,996

(22) PCT Filed: Dec. 15, 2009

(86) PCT No.: PCT/US2009/068007
§ 371 (c)(1),
(2), (4) Date: Dec. 29, 2011

(87) PCT Pub. No.: WO2010/077851
PCT Pub. Date: Jul. 8, 2010

(65) Prior Publication Data
US 2012/0108917 A1    May 3, 2012

Related U.S. Application Data

(60) Provisional application No. 61/122,477, filed on Dec. 15, 2008, provisional application No. 61/158,304, filed on Mar. 6, 2009, provisional application No. 61/252,410, filed on Oct. 16, 2009.

(51) Int. Cl.
*G08B 25/00* (2006.01)

(52) U.S. Cl.
USPC ......................................... 340/6.1

(58) Field of Classification Search
USPC .............. 340/6.1, 5.64, 506, 524, 517; 705/2; 600/347, 365, 301
See application file for complete search history.

(56) References Cited

U.S. PATENT DOCUMENTS

| 4,451,254 A | 5/1984 | Dinius et al. |
| 4,711,248 A * | 12/1987 | Steuer et al. .................. 600/561 |

(Continued)

FOREIGN PATENT DOCUMENTS

| EP | 1 579 801 A1 | 9/2005 |
| JP | H05-161610 | 6/1993 |

(Continued)

OTHER PUBLICATIONS

International Search Report and The Written Opinion of the ISA for International Patent Application PCT/US2010/026977 filed Mar. 11, 2010.

(Continued)

*Primary Examiner* — Vernal Brown
(74) *Attorney, Agent, or Firm* — Billion & Armitage; Benjamin C. Armitage; Michael A. Collins

(57) ABSTRACT

An adherent patient device is configured to adhere to the skin of the patient and measure electrocardiogram data, impedance data, accelerometer data, blood oxygen data and temperature data. The adherent device can communicate wirelessly with gateways and a local processor system, such that the patient can wander about the hospital and update the monitoring station with the patient data when the patient is ambulatory. The local processor system can be configured to customize alerts for the patient, for example to notify automatically a specialist in response to a special condition of the patient. The adherent device may comprise a unique adherent device identifier such that the customized alert can be sent based on the unique device identifier. Each of the gateways can be carried and may comprise a unique gateway identifier, such that the unique device identifier and the unique gateway identifier can be used to locate the ambulatory patient.

63 Claims, 23 Drawing Sheets

(56) References Cited

U.S. PATENT DOCUMENTS

| | | |
|---|---|---|
| 4,730,611 A | 3/1988 | Lamb |
| 5,086,781 A | 2/1992 | Bookspan |
| 5,282,840 A | 2/1994 | Hudrlik |
| 5,511,548 A | 4/1996 | Riazz et al. |
| 5,511,553 A | 4/1996 | Segalowitz |
| 5,564,434 A | 10/1996 | Halperin et al. |
| 5,607,454 A | 3/1997 | Cameron et al. |
| 5,678,562 A | 10/1997 | Sellers |
| 5,778,882 A | 7/1998 | Raymond et al. |
| 5,788,643 A | 8/1998 | Feldman |
| 5,814,079 A | 9/1998 | Kieval |
| 5,860,860 A | 1/1999 | Clayman |
| 5,984,102 A | 11/1999 | Tay |
| 6,047,203 A | 4/2000 | Sackner et al. |
| 6,049,730 A | 4/2000 | Kristbjamarson |
| 6,080,106 A | 6/2000 | Lloyd et al. |
| 6,117,076 A * | 9/2000 | Cassidy ........................ 600/300 |
| 6,398,727 B1 | 6/2002 | Bui et al. |
| 6,416,471 B1 | 7/2002 | Kumar et al. |
| 6,459,934 B1 | 10/2002 | Kadhiresan |
| 6,473,640 B1 | 10/2002 | Erlebacher |
| 6,491,647 B1 | 12/2002 | Bridger et al. |
| 6,579,231 B1 | 6/2003 | Phipps |
| 6,580,942 B1 | 6/2003 | Willshire |
| 6,584,343 B1 | 6/2003 | Ransbury et al. |
| 6,595,927 B2 | 7/2003 | Pitts-Crick et al. |
| 6,697,658 B2 | 2/2004 | Al-Ali |
| 6,714,813 B2 | 3/2004 | Ishigooka et al. |
| 6,804,558 B2 * | 10/2004 | Haller et al. ..................... 607/30 |
| 6,893,396 B2 | 5/2005 | Schulze et al. |
| 7,071,820 B2 * | 7/2006 | Callaway ................. 340/539.12 |
| 7,127,518 B2 * | 10/2006 | Vange et al. ................... 709/230 |
| 7,177,681 B2 | 2/2007 | Zhu et al. |
| 7,206,630 B1 | 4/2007 | Tarler |
| 7,269,427 B2 * | 9/2007 | Hoctor et al. ............... 455/456.2 |
| 7,318,808 B2 | 1/2008 | Tarassenko et al. |
| 7,384,398 B2 | 6/2008 | Gagnadre et al. |
| 7,387,607 B2 * | 6/2008 | Holt et al. ..................... 600/301 |
| 7,400,920 B1 | 7/2008 | Gill et al. |
| 7,411,509 B2 * | 8/2008 | Rosenfeld et al. ......... 340/573.1 |
| 7,647,101 B2 | 1/2010 | Libbus et al. |
| 2002/0138017 A1 | 9/2002 | Bui et al. |
| 2003/0009092 A1 | 1/2003 | Parker |
| 2003/0055461 A1 | 3/2003 | Girouard et al. |
| 2003/0083581 A1 | 5/2003 | Taha et al. |
| 2003/0135127 A1 | 7/2003 | Sackner et al. |
| 2003/0149349 A1 | 8/2003 | Jensen |
| 2003/0221687 A1 | 12/2003 | Kaigler |
| 2003/0233129 A1 | 12/2003 | Matos |
| 2004/0006279 A1 | 1/2004 | Arad (Abboud) |
| 2004/0015058 A1 | 1/2004 | Besson et al. |
| 2004/0044293 A1 | 3/2004 | Burton |
| 2004/0073094 A1 | 4/2004 | Baker |
| 2004/0098060 A1 | 5/2004 | Ternes |
| 2004/0102683 A1 | 5/2004 | Khanuja et al. |
| 2004/0158132 A1 | 8/2004 | Zaleski |
| 2004/0215240 A1 | 10/2004 | Lovett et al. |
| 2004/0215247 A1 | 10/2004 | Bolz |
| 2004/0220639 A1 | 11/2004 | Mulligan et al. |
| 2005/0027207 A1 | 2/2005 | Westbrook et al. |
| 2005/0054944 A1 | 3/2005 | Nakada et al. |
| 2005/0059867 A1 | 3/2005 | Chung |
| 2005/0070768 A1 | 3/2005 | Zhu et al. |
| 2005/0070778 A1 | 3/2005 | Lackey et al. |
| 2005/0085734 A1 | 4/2005 | Tehrani |
| 2005/0113703 A1 | 5/2005 | Farringdon et al. |
| 2005/0158539 A1 | 7/2005 | Murphy et al. |
| 2005/0228238 A1 | 10/2005 | Monitzer |
| 2005/0280531 A1 | 12/2005 | Fadem et al. |
| 2006/0030892 A1 | 2/2006 | Kadhiresan et al. |
| 2006/0064030 A1 | 3/2006 | Cosentino et al. |
| 2006/0064142 A1 | 3/2006 | Chavan et al. |
| 2006/0135858 A1 | 6/2006 | Nidd et al. |
| 2006/0155183 A1 | 7/2006 | Kroecker et al. |
| 2006/0235316 A1 | 10/2006 | Ungless et al. |
| 2006/0241701 A1 | 10/2006 | Markowitz et al. |
| 2006/0252999 A1 | 11/2006 | Devaul et al. |
| 2006/0264730 A1 | 11/2006 | Stivoric et al. |
| 2006/0264767 A1 | 11/2006 | Shennib |
| 2006/0271116 A1 | 11/2006 | Stagmann et al. |
| 2007/0015976 A1 | 1/2007 | Miesel et al. |
| 2007/0027382 A1 | 2/2007 | Berman et al. |
| 2007/0027497 A1 | 2/2007 | Parnis |
| 2007/0073132 A1 | 3/2007 | Vosch |
| 2007/0073181 A1 | 3/2007 | Pu et al. |
| 2007/0106132 A1 | 5/2007 | Elhag et al. |
| 2007/0106167 A1 | 5/2007 | Kinast |
| 2007/0123756 A1 | 5/2007 | Kitajima et al. |
| 2007/0129622 A1 | 6/2007 | Bourget et al. |
| 2007/0142732 A1 | 6/2007 | Brockway et al. |
| 2007/0167850 A1 | 7/2007 | Russel et al. |
| 2007/0172424 A1 | 7/2007 | Roser |
| 2007/0173705 A1 | 7/2007 | Teller et al. |
| 2007/0175827 A1 | 8/2007 | Wariar |
| 2007/0191723 A1 | 8/2007 | Prystowsky |
| 2007/0208262 A1 | 9/2007 | Kovacs |
| 2007/0270678 A1 | 11/2007 | Fadem et al. |
| 2007/0270707 A1 | 11/2007 | Belalcazar |
| 2008/0004664 A1 | 1/2008 | Hopper et al. |
| 2008/0004904 A1 * | 1/2008 | Tran ................................... 705/2 |
| 2008/0091090 A1 | 4/2008 | Guillory et al. |
| 2008/0120784 A1 | 5/2008 | Warner et al. |
| 2008/0139953 A1 | 6/2008 | Baker et al. |
| 2008/0220865 A1 | 9/2008 | Hsu |
| 2008/0259577 A1 | 10/2008 | Hu et al. |
| 2008/0288026 A1 | 11/2008 | Cross et al. |
| 2008/0293491 A1 | 11/2008 | Wu et al. |
| 2008/0319282 A1 | 12/2008 | Tran |
| 2008/0319290 A1 | 12/2008 | Mao et al. |
| 2009/0018456 A1 | 1/2009 | Hung |
| 2009/0048526 A1 | 2/2009 | Aarts et al. |
| 2009/0062670 A1 | 3/2009 | Sterling et al. |
| 2009/0076336 A1 | 3/2009 | Mazar et al. |
| 2009/0076345 A1 * | 3/2009 | Manicka et al. ............... 600/301 |
| 2009/0137888 A9 * | 5/2009 | Berman et al. ................. 600/347 |

FOREIGN PATENT DOCUMENTS

| | | |
|---|---|---|
| JP | 2004-242945 | 9/2004 |
| JP | 2004-275272 | 10/2004 |
| JP | 2005-149085 | 6/2005 |
| JP | 2005-538784 | 12/2005 |
| WO | WO9851211 A1 | 11/1998 |
| WO | WO0079255 A1 | 12/2000 |
| WO | 0189362 A2 | 11/2001 |
| WO | WO 2004/026126 A1 | 4/2004 |
| WO | WO2005104930 A1 | 11/2005 |
| WO | WO2005122888 A1 | 12/2005 |
| WO | WO2007041783 A1 | 4/2007 |
| WO | WO2008068695 A1 | 6/2008 |
| WO | WO2009036260 A1 | 3/2009 |
| WO | WO2009036313 A1 | 3/2009 |
| WO | WO2009036321 A1 | 3/2009 |
| WO | WO2009036327 A1 | 3/2009 |
| WO | WO2009036329 A1 | 3/2009 |
| WO | WO2009036369 A1 | 3/2009 |

OTHER PUBLICATIONS

International Preliminary Report on Patentability for International Patent Application PCT/US2010/026977 filed Mar. 11, 2010.

International Search Report and The Written Opinion of the ISA for International Patent Application PCT/US2010/027663 filed Mar. 17, 2010.

International Preliminary Report on Patentability for International Patent Application PCT/US2010/027663 filed Mar. 17, 2010.

Cianci, R., et al. Body fluid compartments in hypertension. European Review for Medical and Pharmacological Sciences 2006, 10, pp. 75-78.

Yu, C-M., et al. Intrathoracic Impedance Monitoring in Patients With Heart Failure. Circulation 2005, 112, pp. 841-848.

(56) References Cited

OTHER PUBLICATIONS

Kyle, U.G., et al. Bioelectrical impedance analysis—part I: Review of principles and methods. Clinical Nutrition 2004, 23, pp. 1226-1243.
Notification of Transmittal of the International Search Report and The Written Opinion of the ISA for related International Patent Application PCT/US2009/068007 filed Dec. 15, 2009.
International Preliminary Report on Patentability for related International Patent Application PCT/US2009/068007 filed Dec. 15, 2009.
Notification of Transmittal of the International Search Report and The Written Opinion of the ISA for International Patent Application PCT/US2008/076265 filed Sep. 12, 2008.
International Preliminary Report on Patentability for International Patent Application PCT/US2008/076265 filed Sep. 12, 2008.
Notification of Transmittal of the International Search Report and The Written Opinion of the ISA for International Patent Application PCT/US2008/076235 filed Sep. 12, 2008.
International Preliminary Report on Patentability for International Patent Application PCT/US2008/076235 filed Sep. 12, 2008.
Notification of Transmittal of the International Search Report and The Written Opinion of the ISA for International Patent Application PCT/US2008/076241 filed Sep. 12, 2008.
International Preliminary Report on Patentability for International Patent Application PCT/US2008/076241 filed Sep. 12, 2008.
Notification of Transmittal of the International Search Report and The Written Opinion of the ISA for International Patent Application PCT/US2008/076288 filed Sep. 12, 2008.
International Preliminary Report on Patentability for International Patent Application PCT/US2008/076288 filed Sep. 12, 2008.
Notification of Transmittal of the International Search Report and The Written Opinion of the ISA for International Patent Application PCT/US2008/076243 filed Sep. 12, 2008.
International Preliminary Report on Patentability for International Patent Application PCT/US2008/076243 filed Sep. 12, 2008.
Notification of Transmittal of the International Search Report and The Written Opinion of the ISA for International Patent Application PCT/US2008/076226 filed Sep. 12, 2008.
International Preliminary Report on Patentability for International Patent Application PCT/US2008/076226 filed Sep. 12, 2008.
Notification of Transmittal of the International Search Report and The Written Opinion of the ISA for International Patent Application PCT/US2008/076217 filed Sep. 12, 2008.
International Preliminary Report on Patentability for International Patent Application PCT/US2008/076217 filed Sep. 12, 2008.
Notification of Transmittal of the International Search Report of the ISA for International Patent Application PCT/US2008/076240 filed Sep. 12, 2008.
Notification of Transmittal of the International Preliminary Report on Patentability for International Patent Application PCT/US2008/076240 filed Sep. 12, 2008.
Notification of Transmittal of the International Search Report and the Written Opinion of the ISA for International Patent Application PCT/US2008/076150 filed Sep. 12, 2008.
International Search Report and The Written Opinion of the ISA for International Patent Application PCT/US2008/076233 filed Sep. 12, 2008.
International Preliminary Report on Patentability for International Patent Application PCT/US2008/076233 filed Sep. 12, 2008.
International Search Report and The Written Opinion of the ISA for International Patent Application PCT/US2008/076248 filed Sep. 12, 2008.
International Preliminary Report on Patentability for International Patent Application PCT/US2008/076248 filed Sep. 12, 2008.
International Search Report and The Written Opinion of the ISA for International Patent Application PCT/US2008/076247 filed Sep. 12, 2008.
International Preliminary Report on Patentability for International Patent Application PCT/US2008/076247 filed Sep. 12, 2008.
International Search Report and The Written Opinion of the ISA for International Patent Application PCT/US2008/076230 filed Sep. 12, 2008.
International Preliminary Report on Patentability for International Patent Application PCT/US2008/076230 filed Sep. 12, 2008.
International Search Report and The Written Opinion of the ISA for International Patent Application PCT/US2008/076146 filed Sep. 12, 2008.
International Preliminary Report on Patentability for International Patent Application PCT/US2008/076146 filed Sep. 12, 2008.
International Search Report and The Written Opinion of the ISA for International Patent Application PCT/US2009/036690 filed Mar. 10, 2009.
International Preliminary Report on Patentability for International Patent Application PCT/US2009/036690 filed Mar. 10, 2009.
International Search Report and The Written Opinion of the ISA for International Patent Application PCT/US2010/053788 filed Oct. 22, 2010.
International Preliminary Report on Patentability for International Patent Application PCT/US2010/053788 filed Oct. 22, 2010.
International Search Report and The Written Opinion of the ISA for International Patent Application PCT/US2010/060121 filed Dec. 13, 2010.
International Preliminary Report on Patentability for International Patent Application PCT/US2010/060121 filed Dec. 13, 2010.
International Search Report of the ISA for International Patent Application PCT/US2011/030991 filed Apr. 1, 2011.
International Search Report and The Written Opinion of the ISA for International Patent Application PCT/US2009/068007 filed Dec. 15, 2009.
International Preliminary Report on Patentability for International Patent Application PCT/US2009/068007 filed Dec. 15, 2009.
International Search Report and The Written Opinion of the ISA for International Patent Application PCT/US2010/026828 filed Mar. 10, 2010.
International Preliminary Report on Patentability for International Patent Application PCT/US2010/026828 filed Mar. 10, 2010.
International Search Report and The Written Opinion of the ISA for International Patent Application PCT/US2010/026864 filed Mar. 10, 2010.
International Preliminary Report on Patentability for International Patent Application PCT/US2010/026864 filed Mar. 10, 2010.
International Search Report and The Written Opinion of the ISA for International Patent Application PCT/US2010/026967 filed Mar. 11, 2010.
International Preliminary Report on Patentability for International Patent Application PCT/US2010/026967 filed Mar. 11, 2010.
International Search Report and The Written Opinion of the ISA for International Patent Application PCT/US2010/026950 filed Mar. 11, 2010.
International Preliminary Report on Patentability for International Patent Application PCT/US2010/026950 filed Mar. 11, 2010.
International Search Report and The Written Opinion of the ISA for International Patent Application PCT/US2010/027202 filed Mar. 12, 2010.
International Preliminary Report on Patentability for International Patent Application PCT/US2010/027202 filed Mar. 12, 2010.
Notice of Rejection Grounds for corresponding Japanese Application No. 2011-540963 mailed on Dec. 24, 2013.

* cited by examiner

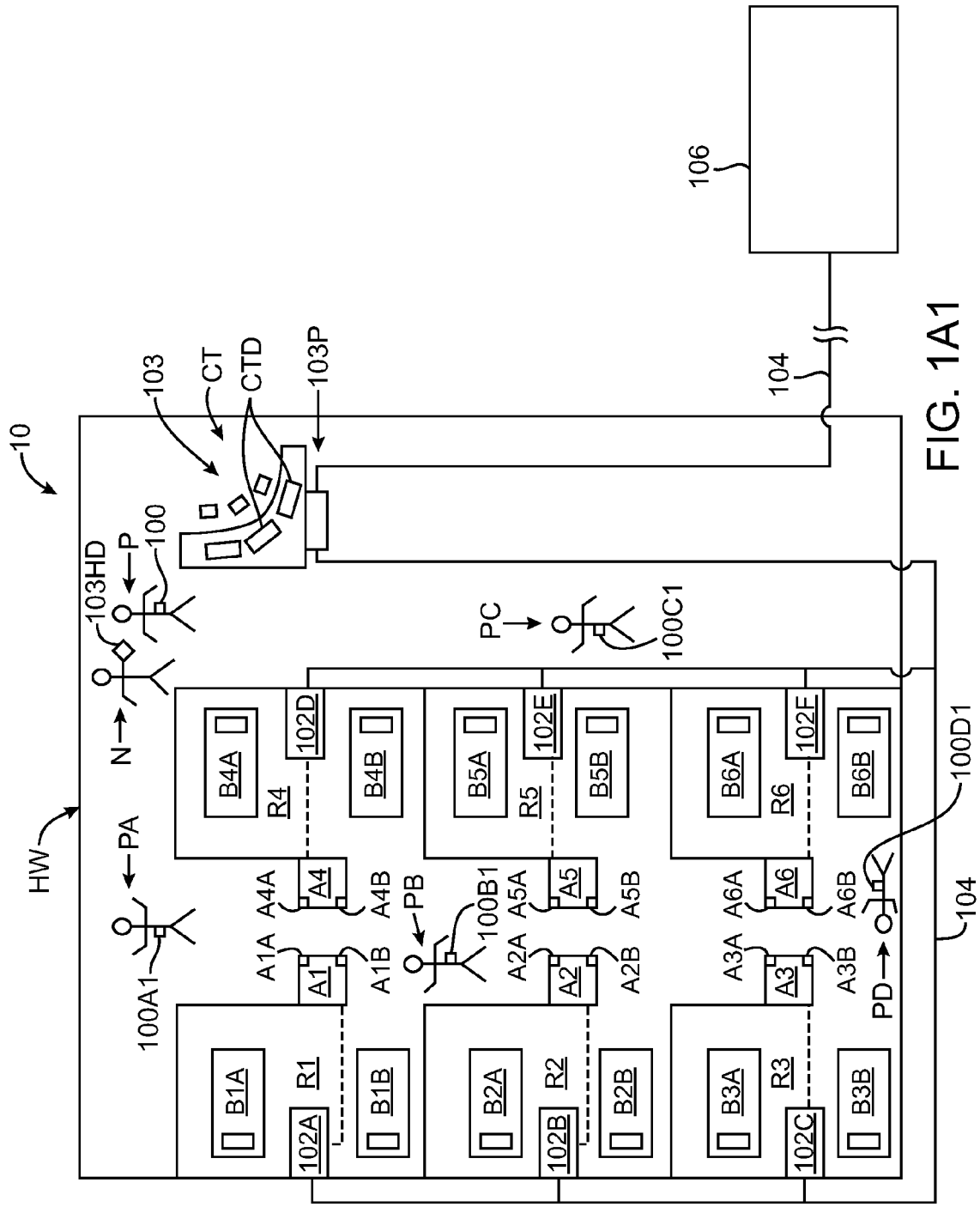
FIG. 1A1

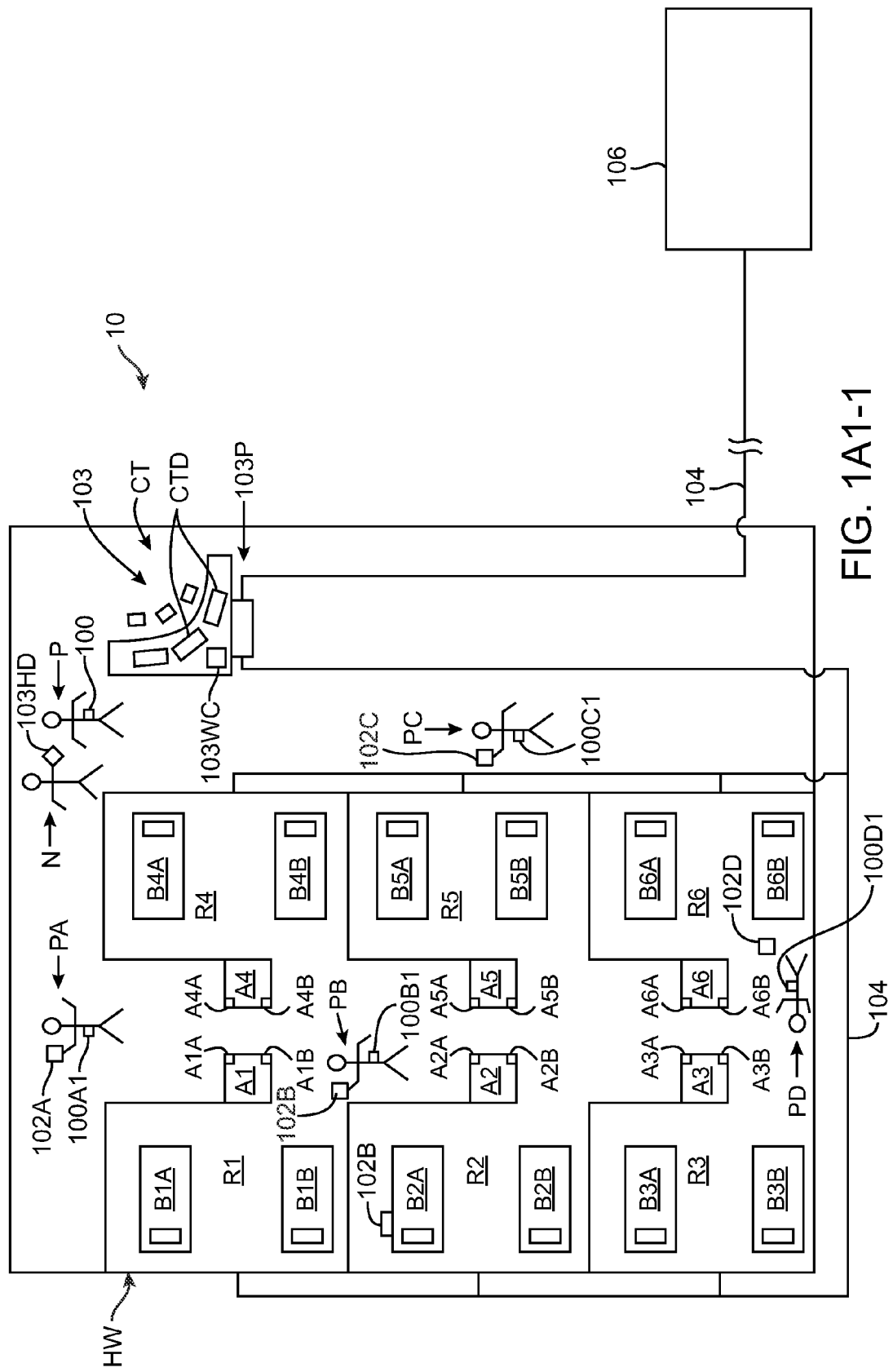
FIG. 1A1-1

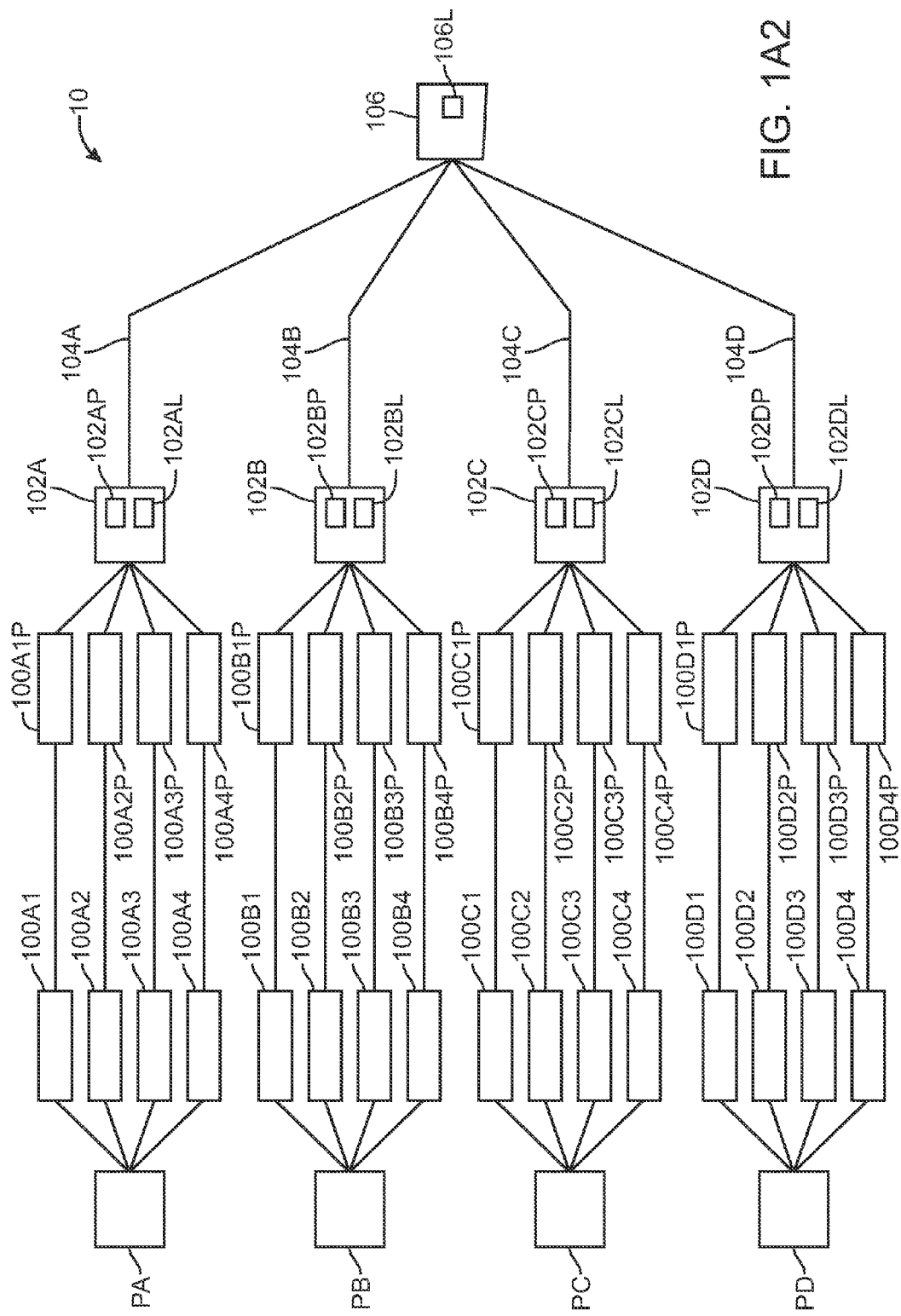
FIG. 1A2

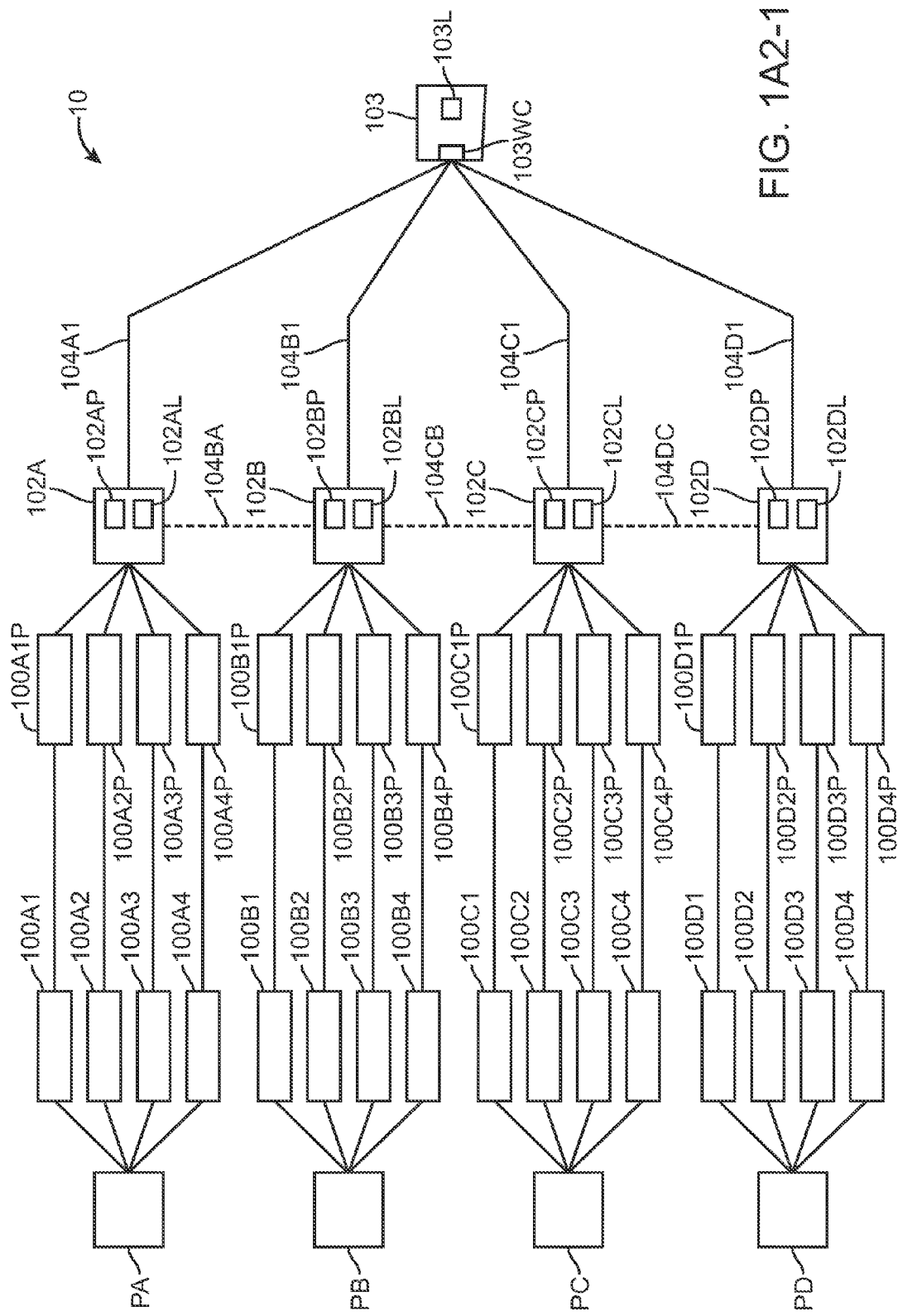
FIG. 1A2-1

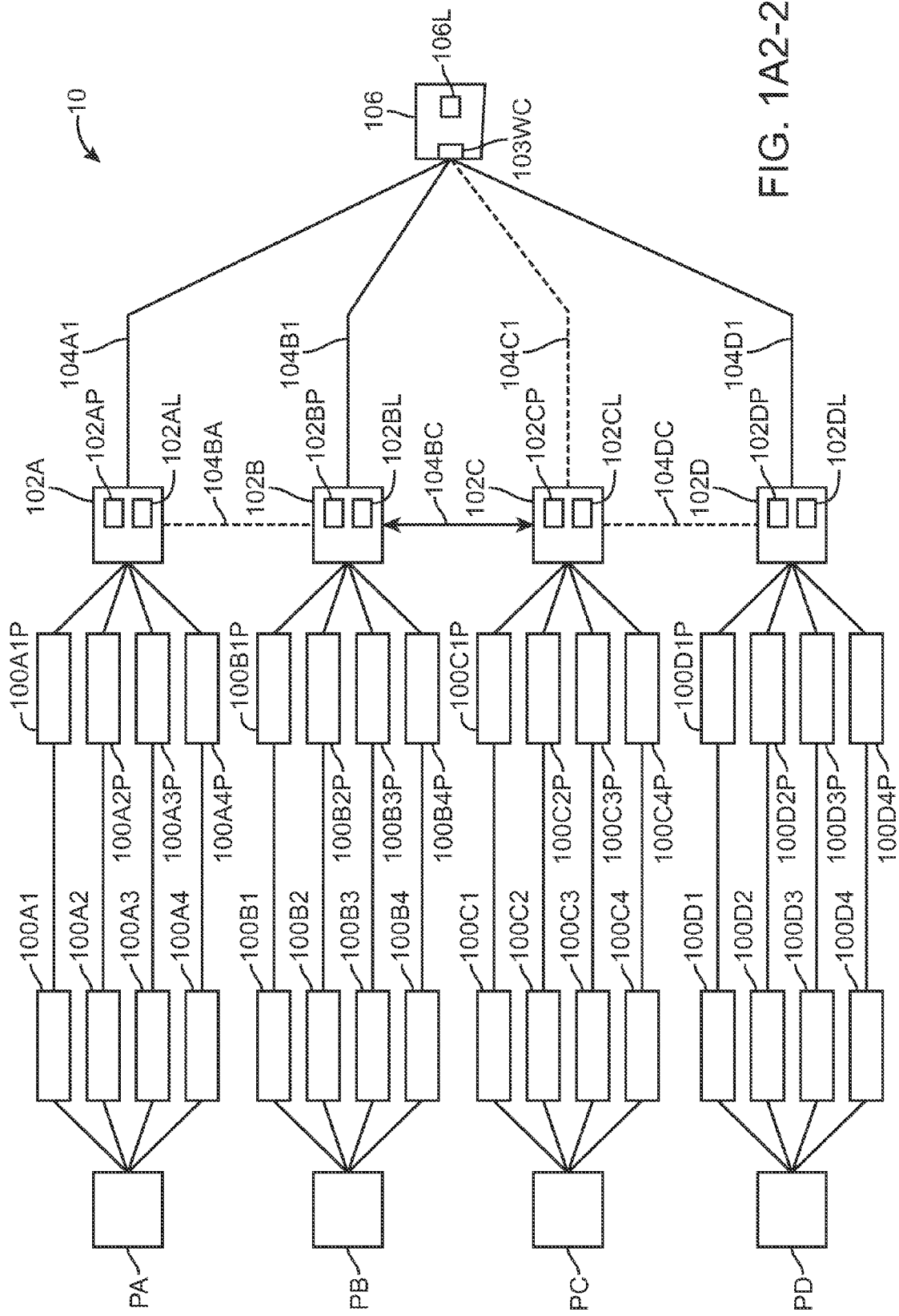
FIG. 1A2-2

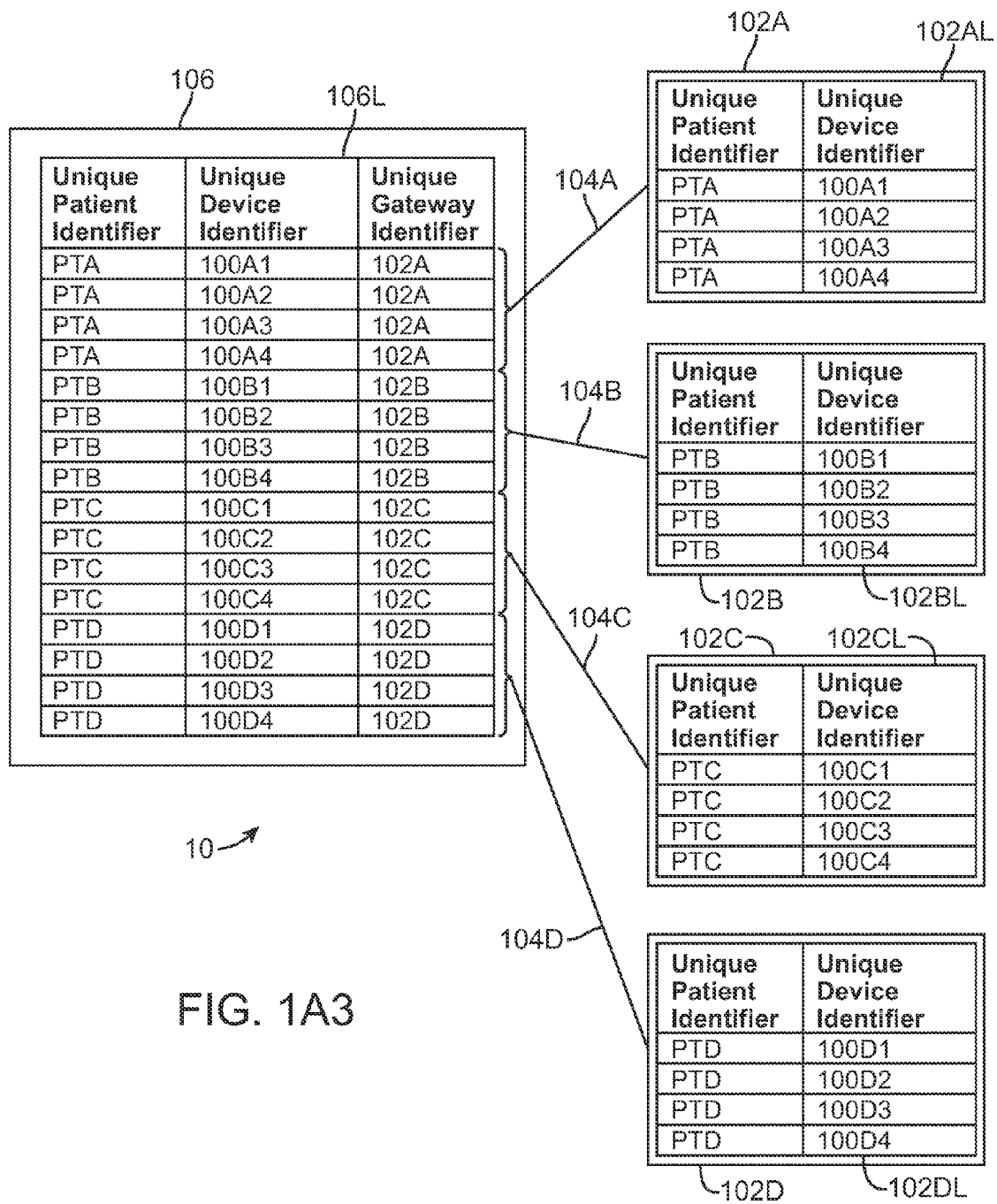
FIG. 1A3

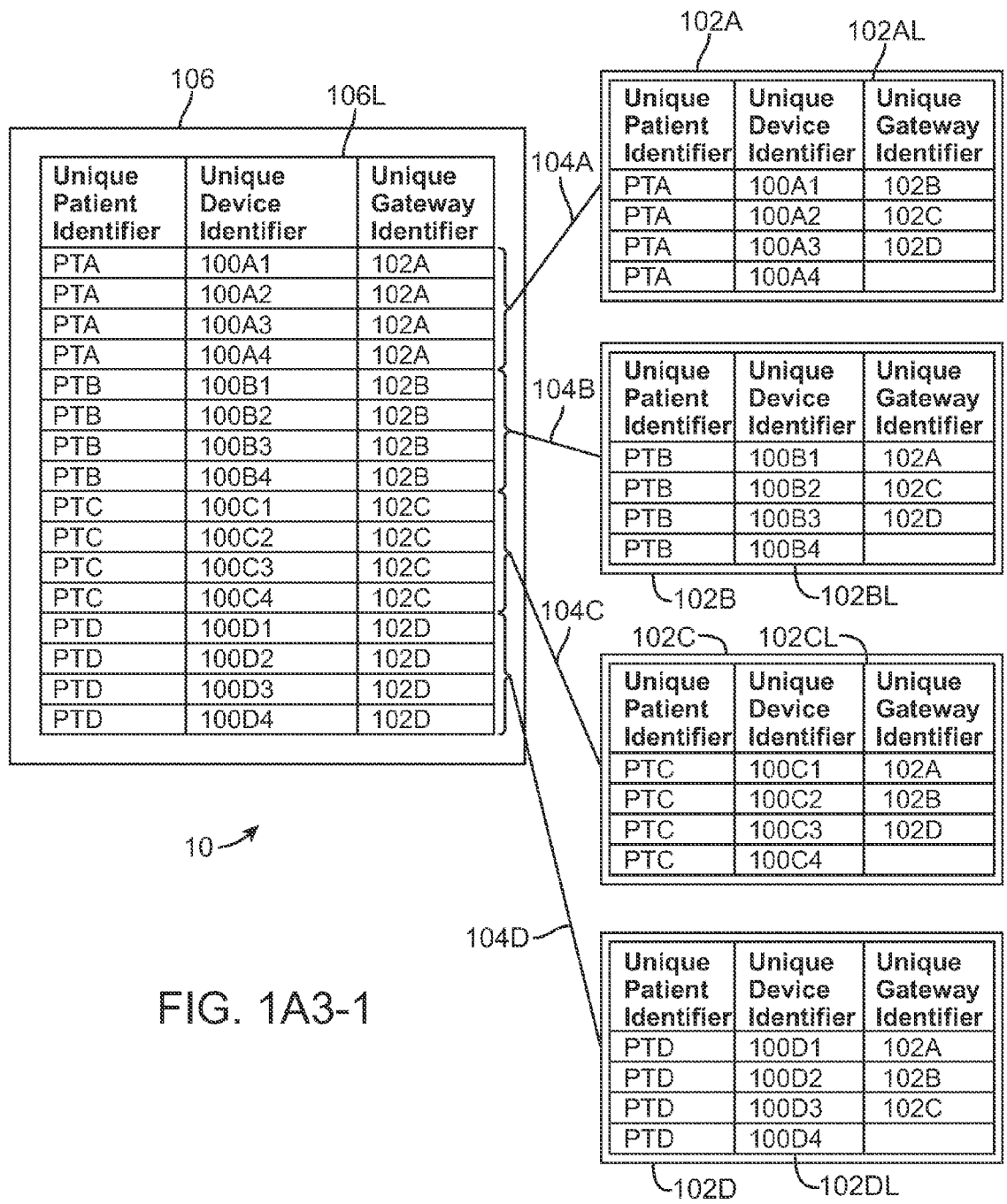
FIG. 1A3-1

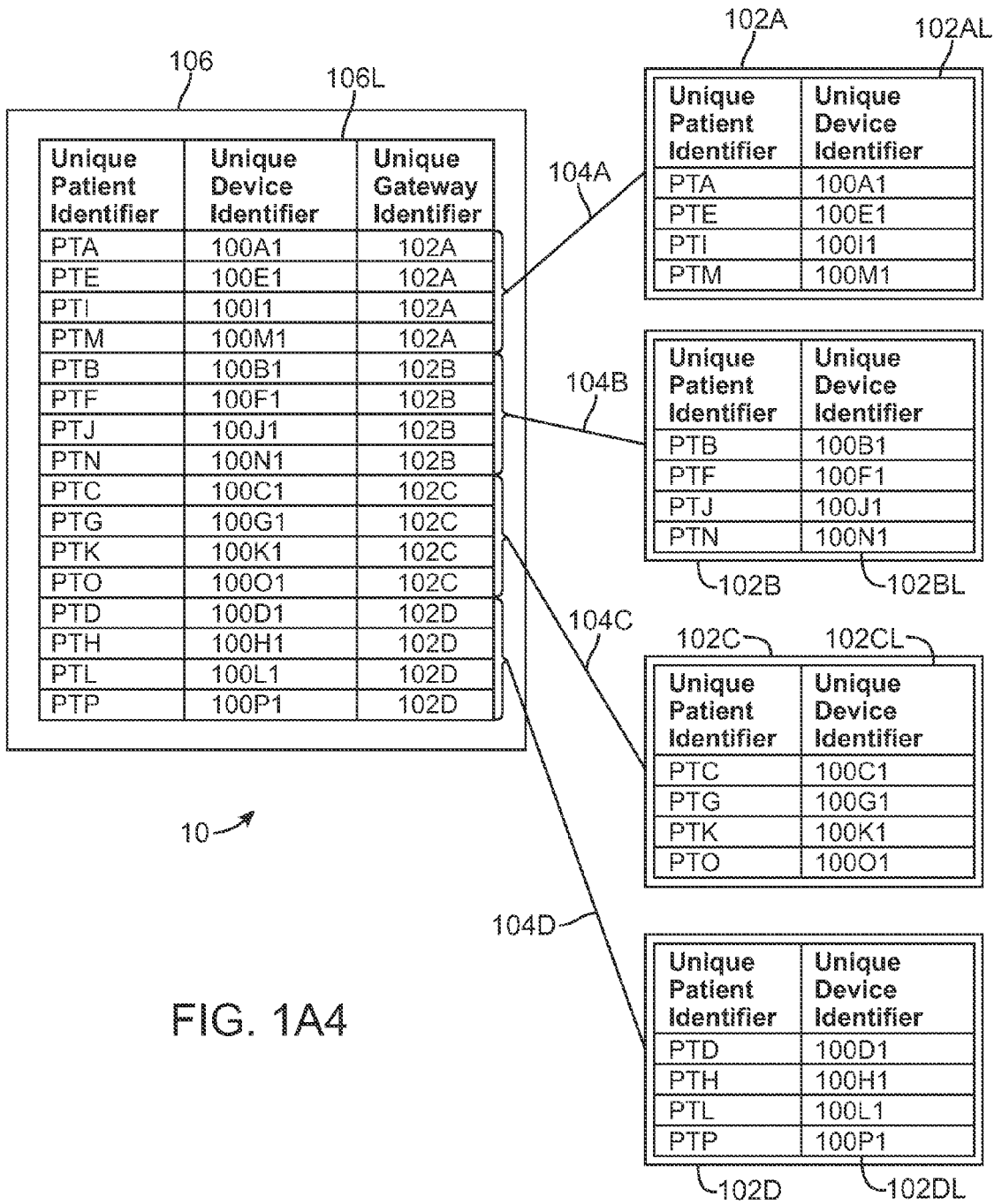
FIG. 1A4

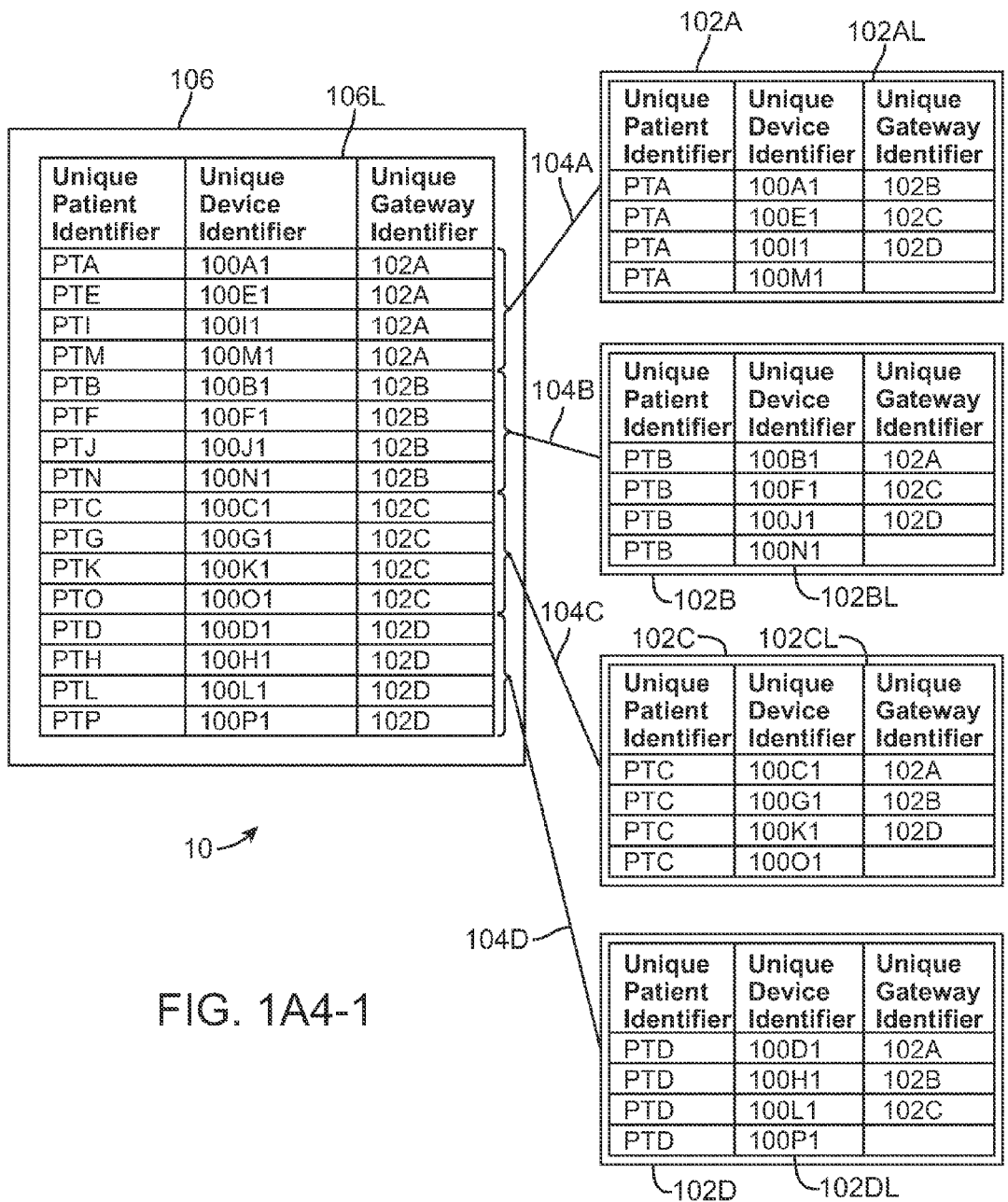
FIG. 1A4-1

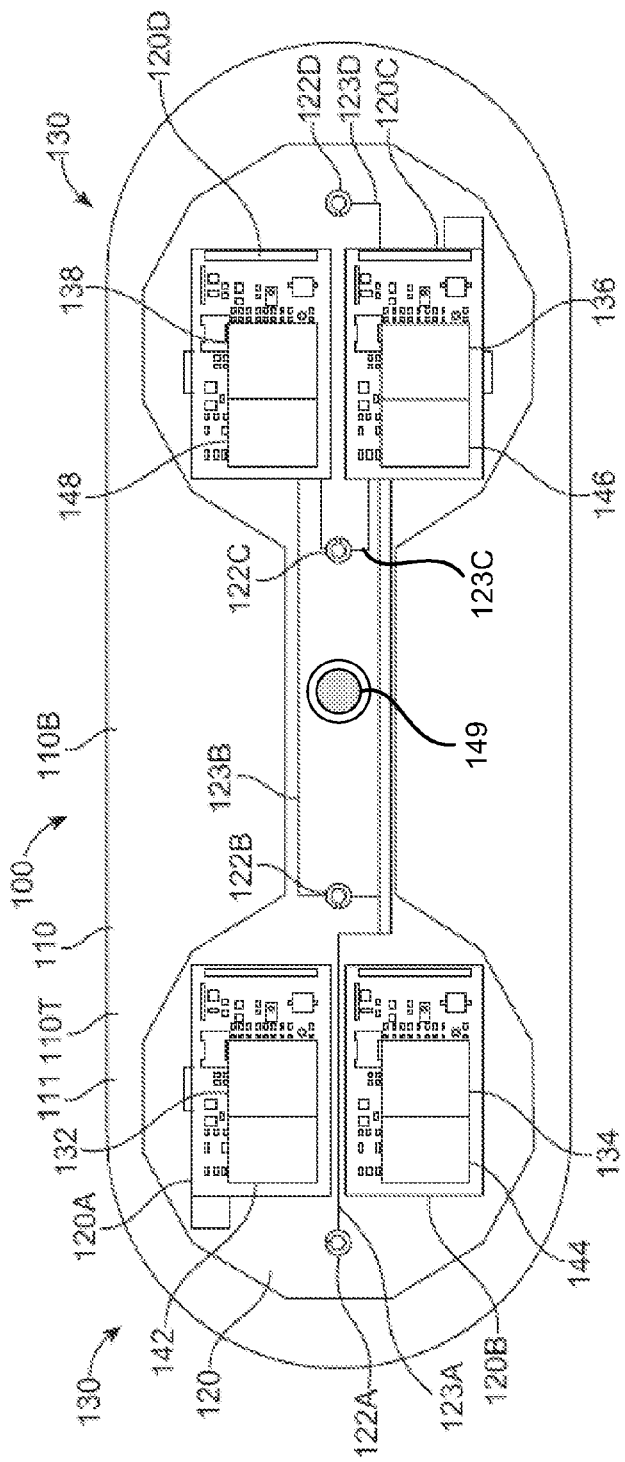
FIG. 1D
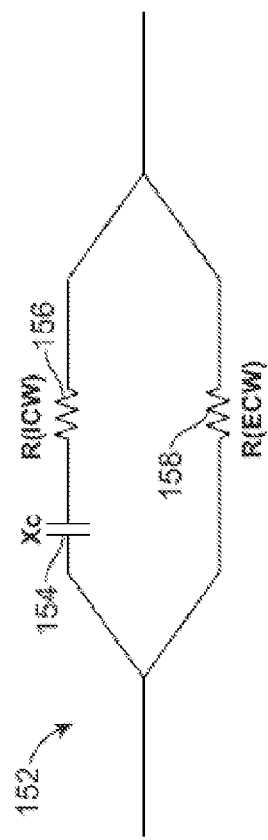
FIG. 1D1

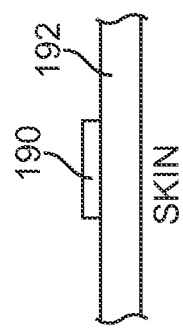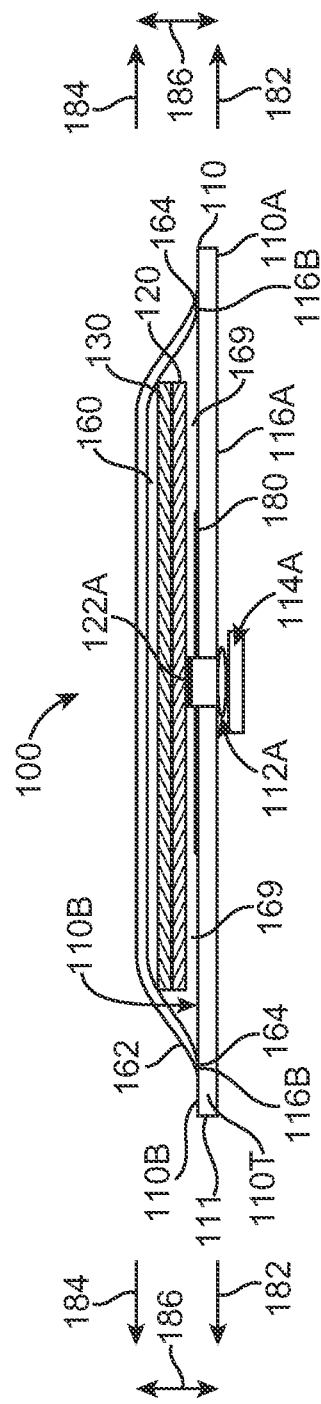

PATIENT MONITORING SYSTEMS AND METHODS

CROSS-REFERENCES TO RELATED APPLICATIONS

The present application is a national stage filing of PCT/US2009/068007, filed Dec. 15, 2009, which claims priority to U.S. Provisional Patent Application No. 61/122,477, filed on Dec. 15, 2008; and U.S. Application No. 61/158,304, filed on Mar. 6, 2009; and U.S. Application No. 61/252,410, filed Oct. 16, 2009, the full disclosures of which are incorporated herein by reference.

BACKGROUND OF THE INVENTION

1. Field of the Invention

The present invention is related to patient monitoring. Although embodiments make specific reference to acute patient monitoring in a hospital ward, the systems, methods and devices described herein may be applicable to many applications in which physiological monitoring is used, for example wireless physiological monitoring for extended periods.

Patients can be treated for diseases and/or conditions associated with a compromised status of the patient, for example a compromised physiologic status. In at least some instances patients can be placed in a ward to ensure proper care, such as ward of a convalescent hospital, a nursing home or a hospital. In some instances, a patient in a ward, for example a hospitalized patient, may be monitored to determine the underlying cause of illness. Hospital patients requiring intensive care may be admitted to an intensive care unit (hereinafter "ICU"), and hospitalized patients requiring intensive care can be admitted to a general ward of the hospital. However, health care costs continue to rise and in at least some instances people are uninsured, such that people may be unable to receive proper medical treatment in at least some instances. ICU care can be very expensive and ICU space limited, such that ICU care can significantly increase the cost of hospitalization, and in at least some instances a person may become very sick before being admitting to an ICU.

It would be helpful if improved patient monitoring were available that could at least decrease, or even minimize the need for ICU care and hospital care. An ICU can include complex instrumentation and highly trained staff, both of which may be needed to monitor and treat the patient. In at least some instances it may not be appropriate to release a patient from an ICU to a general ward of a hospital due to limitations of the instrumentation available in the general ward of a hospital. Also, there may be some patients in the general ward of a hospital who can benefit from improved monitoring, for example to detect the onset of a life threatening condition, such that the patient can be treated for the life threatening condition before ICU care is needed.

Work in relation to embodiments of the present invention suggests that known methods and apparatus for monitoring patients in hospital and long term care settings may be less than ideal. In at least some instances, the currently known methods and apparatus to monitor several patients in a hospital ward may be more difficult and time consuming for hospital staff than would be ideal. At least some of the known ICU monitoring systems may not be well suited for use in a general hospital ward. For example at least some of the known patient measurement devices may not be configured to measure and transmit data optimally from an ambulatory patient, such as may occur with a patient in a general ward who can wander about the ward. In at least some instances exercise such as walking may be helpful to the patient and increase the rate recovery. Although at least some of the known instrumentation and data systems for use in the ICU may work well with a stationary patient who remains in bed, these instrumentation and data systems may have less then ideal performance when the patient is ambulatory and moves about the hospital, for example with healthy walks for exercise.

Although wireless communication devices may transmit measured patient data, in at least some instances problems can arise with mobile patients that may not occur with stationary patients such as ICU patients. For example when several mobile patients are monitored communication through a gateway device may become slow and congested, such that communication is somewhat slower than ideal. In at least some instances, important information may not pass through the gateway to a monitoring site in a timely manner. Also, at least some of the known methods and devices that use mesh communication protocols such as ZigBee can result in communication that is slower than ideal in at least some instances.

Therefore, a need exists for improved patient monitoring in patient wards such as wards in a hospital setting. Ideally, such improved patient monitoring would minimize, or even avoid, at least some of the short-comings of the present methods and devices.

2. Background Art

The following U.S. patents and Publications may describe relevant background art: U.S. Pat. Nos. 4,121,573; 4,955,381; 4,981,139; 5,080,099; 5,319,363; 5,353,793; 5,511,553; 5,544,661; 5,558,638; 5,718,234; 5,724,025; 5,772,586; 5,862,802; 5,944,659; 6,047,203; 6,117,077; 6,129,744; 6,213,942; 6,616,606; 6,225,901; 6,385,473; 6,416,471; 6,454,707; 6,527,711; 6,527,729; 6,544,174; 6,551,252; 6,595,927; 6,595,929; 6,605,038; 6,616,606; 6,645,153; 6,659,947; 6,821,249; 6,980,851; 6,988,989; 7,020,508; 7,054,679; 7,088,242; 7,130,396; 7,153,262; 7,156,807; 7,336,187; 7,382,247; 2003/0092975; 2004/0100376; 2004/0225199; 2005/0113703; 2005/0131288; 2005/0206518; 2006/0010090; 2006/0031102; 2006/0074462; 2006/0089679; 2006/0122474; 2006/0142820; 2006/0155183; 2006/0202816; 2006/0224051; 2006/0235281; 2006/0264730; 2006/0293571; 2007/0015973; 2007/0038038; 2007/0021678; 2007/0180140; 2007/0180047; 2007/0255120; 2008/0004499; 2008/0058614

BRIEF SUMMARY OF THE INVENTION

The systems, methods and devices of embodiments of the present invention provide improved patient monitoring in wards with ambulatory patients, for example in the hospital setting with ambulatory hospital patients and patients of an extended care facility such as a convalescent hospital or a mental hospital. The systems, methods and devices of many embodiments provide an adherent patient device configured to adhere to the skin of the patient in which many measurements can be provided for many patients in the ward. The adherent device can communicate wirelessly with at least one gateway and a local processor system, such that the patient can wander about the ward and update the monitoring station with patient data when the patient is ambulatory. The adherent device can comprise an emergency notification switch operable by the patient to trigger an emergency notification transmission from the adherent device. The emergency notification transmission can be used to alert a health-care provider of the patient-initiated emergency notification. The local processor system can be configured to customize alerts for the patient, for example to notify automatically a specialist in response to a special condition of the patient. The adherent device may comprise a unique adherent device identifier, and the patient can be associated with the unique adherent device identifier, for example when the patient is admitted, such that the customized alert can be sent based on the unique adherent device identifier. Each of the gateways may comprise a unique gateway identifier, such that the unique adherent device identifier and the gateway identifier can be used to locate an ambulatory patient in the hospital, for example when the patient has walked away from his or her bed. The adherent device can be configured to measure at least one of an electrocardiogram data, impedance data, accelerometer data, blood oxygen data or temperature data. In many embodiments, the gateways comprise communication circuitry configured to communicate wirelessly to the monitoring station, for example with a cellular communication protocol, such that the adherent devices and gateways can be readily deployed in existing patient wards with existing monitoring stations. The wireless communication circuitry of the gateways may be configured to communicate wirelessly directly with communication circuitry of the monitoring station and may also be configured with a mesh networking protocol so as to communicate with the monitoring station indirectly through other gateways when the direct connection with the monitoring station circuitry is not available.

In a first aspect, embodiments of the present invention provide a system to monitor a plurality of patients. The system comprises a plurality of adherent patient devices, in which each adherent patient device comprises an adhesive and wireless communication circuitry. Each device is configured to adhere to a skin of one of the plurality of patients to measure patient data and support the wireless communication circuitry. The wireless communication circuitry is configured to transmit the patient data. A local processor system comprises a tangible medium and at least one display disposed at a monitoring station. The local processor system is configured to receive the patient data and display the patient data to a user at the monitoring station. A plurality of gateways is configured to receive the patient data from the wireless communication circuitry and transmit the patient data to the local processor system.

In many embodiments, the monitoring station comprises a nurses' station, and the user comprises a plurality of nurses. The at least one display may comprise a central terminal disposed at the nurses' station to display the patient data to the plurality of nurses. The at least one display can be configured to display a status of each of the plurality of patients.

In many embodiments, each adherent patient device comprises a unique device identifier, and the local processor system is configured to customize an alert for each adherent device of the plurality based on the unique device identifier. Each patient may have a unique patient identifier, and the local processor system can be configured to associate the unique device identifier with at least one of the unique patient identifier, a name of the patient, an assigned room of the patient or an assigned bed of the patient. For example, the local processor system may be configured to associate the unique device identifier with the unique patient identifier and send the customized alter to the physician in response to the unique device identifier.

In many embodiments, the local processor system comprises at least one handheld mobile device configured to customize the alert. The local processor system can be configured to customize the alerts with at least one of a physician to notify, a family member to notify or a health care provider to notify. The local processor system can be configured to customize the alerts in response to a condition of the patient and to select a specialized physician to notify in response to a special condition of the patient. The specialized physician may comprise at least one of a cardiologist, a nephrologist or an obstetrician, and the specialized condition may comprise at least one of a heart condition, a kidney condition or a fetal condition.

In many embodiments, the system comprises a plurality of alert devices, in which the alter devices comprise at least one of a light, a beeper, a buzzer, and each of the plurality of alert devices is located on one or more of the adherent patient device, the gateway, the monitoring station or an alarm device coupled to the gateway. For example, the alert device may comprise the alarm device coupled to the gateway, and the local processor system may be configured to activate each alarm device in response to a unique gateway identifier and a unique adherent device identifier. Each alert device may comprise a switch to deactivate the alert device.

In many embodiments, the local processor system comprises a front end server connected to the plurality of gateways, in which the front end server is configured to receive the patient data from the plurality of gateways and to show the patient data on the at least one display.

In many embodiments, the system comprises a remote processor system having a back end server located remote from the front end server, in which the back end server is configured to receive at least a portion of the patient data from the front end server. The local processor system can be configured to detect an immediate life threatening condition of the patient and issue an alert in response to the patient data, and the remote processor system can be configured to detect a non-immediate life threatening condition of the patient and issue an alert in response to the patient data. The immediate life threatening condition may comprise at least one of an immediate life threatening heart condition or an immediate life threatening fetal condition, and the non-immediate life threatening condition may comprise at least one of a non-life threatening heart condition, a non-life threatening kidney condition or a non-life threatening fetal condition. For example, the life immediate threatening condition may comprise the immediate life threatening heart condition, and the immediate life threatening heart condition may comprise at least one of a ventricular tachycardia or a ventricular fibrillation. The non-life threatening condition may comprise the non-life threatening heart condition, and the non-life threatening heart condition may comprise at least one of a non-sustained ventricular tachycardia or an atrial fibrillation.

In many embodiments, each adherent patient device comprises an adherent device processor comprising a tangible medium configured to process the patient data, and each gateway comprises a gateway processor comprising a tangible medium configured to process patient data. The local processor system is configured to process patient data transmitted from the plurality of gateway devices and transmit processed patient data to a remote processor system.

In many embodiments, each adherent patient device comprises a unique patient device identifier, and the local processor system is configured to store a list with the unique patient device identifier for each patient device adhered to the patient. Each gateway of the plurality of gateways is configured to communicate with at least one of the plurality of patient devices in response to the list. Each gateway may be configured to transmit patient data and the unique patient device identifier in response to the list.

In many embodiments, the local processor system is configured to receive the patient data and determine locations of the plurality of patients when at least some of the patients are mobile. For example, each gateway can be positioned at a unique location, and each gateway of the plurality of gateways may comprise a unique gateway identifier. Each gateway of the plurality of gateways may be configured to transmit the unique gateway identifier, the unique patient device identifier and the patient data to the local processor system, and the local processor system may be configured to determine the location of each patient in response to the unique gateway identifier and the unique patient device identifier.

In many embodiments, a first portion of the plurality of gateways is configured to communicate with a first portion of the plurality of adherent patient devices adhered to a first portion of the plurality of patients, and a second portion of the plurality of gateways is configured to communicate with a second portion of the plurality of adherent patient devices adhered to a second portion of the plurality of patients. The first portion of the plurality of gateways may cover a first area, and the second portion of the plurality of gateways may cover a second area, in which the first area overlaps substantially with the second area, such that the first portion of adherent devices transmit patient data through the first portion of the plurality of gateways when the first portion of the plurality of patients roam the second area. The second portion of adherent devices may transmit patient data through the second portion of the plurality of gateways when the second portion of the plurality of patients roam the first area.

In many embodiments, the first portion of the plurality of gateways comprises a first unique gateway device list comprising the unique identifiers of the first portion of patient devices, and the second portion of the plurality of gateways comprises a second unique gateway device list comprising the unique identifiers of the second portion of patient devices. The first portion of the plurality of gateways may comprise at least about five gateways, and the first portion of the plurality of adherent patient devices may comprise at least about ten adherent patient devices. The second portion of the plurality of gateways may comprise at least about five gateways, and the second portion of the plurality of adherent patient devices may comprise at least about ten adherent patient devices.

In many embodiments, the local processor system is configured to change the list to an updated list and transmit at least a portion of the updated list to at least a portion of the plurality of gateways when one of the plurality of adherent devices is at least one of adhered to or removed from one of the patients.

In many embodiments, the adherent patient device comprises a plurality of adherent patient devices configured to adhere simultaneously to the patient on opposite sides of a chest of the patient to enhance fidelity of data signal measured from the patient. For example, the plurality of adherent patient devices may comprise a first adherent device comprising first wireless communication circuitry, and a second adherent device comprising second wireless communication circuitry. The first adherent device may comprise a first at least two electrodes to measure a first cardiac vector on a first side of the chest, and the second adherent device may comprise a second adherent device comprising a second at least two electrodes to measure a second cardiac vector, the first wireless communication circuitry configured to transmit the first cardiac vector, the second wireless communication circuitry configured to transmit the second cardiac vector.

In many embodiments, the adherent patient device comprises a GPS receiver to locate the adherent patient device adhered to the patient.

In many embodiments, at least one of the adherent patient device, the gateway or the monitoring station comprise a battery indicator to indicate battery power.

In many embodiments, the plurality of gateways comprises a hospital-wide gateway network configured to monitor the plurality of patients when at least some the patients are ambulatory and roam the hospital.

In many embodiments, each gateway of the plurality of gateways comprises first wireless communication circuitry configured to communicate with one or more of the plurality of adherent patch devices and second wireless communication circuitry configured to communicate with a transceiver of the local processor system. Each gateway of the plurality of gateways can be configured to be carried by a patient of the plurality of patients.

The gateways can be configured in many ways to communicate with the transceiver of the local processor system. Each gateway of the plurality of gateways may be configured to communicate directly with the transceiver of the local processor system. For example, each gateway of the plurality of gateways may be configured to communicate with a cellular connection to the transceiver of the local processor system. Alternatively or in combination, each gateway of the plurality of gateways may be configured to communicate with at least one other gateway of the plurality of gateways with a mesh wireless communication protocol, for example when direct communication is not available. Many mesh protocols can be used, and the mesh wireless communication protocol may comprise a ZigBee communication protocol.

In many embodiments, each gateway of the plurality of gateways comprises a unique gateway device identifier. Each gateway of the plurality can be configured to communicate with at least one other gateway in response to the unique gateway device identifier of the at least one other gateway. For example, each gateway of the plurality may comprise a list of unique gateway device identifiers and each gateway can be configured to communicate with the at least one other gateway in response to the list.

The list at each gateway can be configured in many ways to regulate beneficially the communication among the gateways and maintain the integrity of the network. For example, the list at each gateway may comprise at least one unique gateway identifier and at least one of a unique patient identifier or a unique device identifier. Each gateway can be configured to communicate with the at least one other gateway in response to the at least one unique gateway identifier, and to communicate with one or more of the plurality of adherent devices in response to the at least one of the unique patient identifier or the unique adherent device identifier.

In many embodiments, each gateway of the plurality is configured to transmit the unique gateway device identifier with the patient data to determine which gateways transmit the patient data for each patient to the local processor system. For example, each gateway of the plurality can be configured to transmit the unique gateway device identifier with the patient data to determine a path of the patient data, which can be helpful to locate the patient and to evaluate the integrity of the network.

In many embodiments, each adherent patient device comprises impedance circuitry, electrocardiogram circuitry, accelerometer circuitry, oximetry circuitry and at least one of a temperature sensor or a heat flux sensor. The impedance circuitry may be configured to measure patient impedance data to determine at least one of patient hydration or patient respiration. The electrocardiogram circuitry may be configured to measure an electrocardiogram data of the patient. The accelerometer circuitry may be configured to measure acceleration data of the patient, for example for when the patient falls and/or for sleep orientation. The oximetry circuitry may be configured to measure patient blood oxygen, for example a percentage of oxygen saturation. The at least one of a temperature sensor or a heat flux sensor may be configured to measure temperature data of the patient. The wireless communication circuitry may be configured to transmit the impedance data, the electrocardiogram data, the accelerometer data, the blood oxygen data, or the temperature data to at least one gateway of the plurality of gateways.

In many embodiments, at least one of the local processor system or the processor of the adherent patch device is configured to trigger an alert in response to at least one of a patient fall, a patient respiratory distress or a patient oxygen distress.

In many embodiments, each adherent patient device comprises an emergency notification switch operable by the patient to trigger an emergency notification transmission. Each adherent patient device can comprise a unique device identifier, and the patient-initiated emergency notification transmission can comprise the unique device identifier. The local processor system can be configured to receive the patient-initiated emergency notification transmission (directly and/or as relayed by the plurality of gateways), and can be configured to identify the originating adherent patient device in response to the received emergency notification. Each patient can have a unique patient identifier. The local processor system can be configured to associate the unique device identifier of the received emergency notification with at least one of the unique patient identifier, a name of the patient, an assigned room of the patient, or an assigned bed of the patient.

In another aspect, embodiments of the present invention provide a method of monitoring a plurality of patients. At least one adherent patient device comprising wireless communication circuitry is adhered to a skin of at least one patient of the plurality of patients to measure patient data, such that the wireless communication circuitry is supported with the skin of the patient. The patient data is transmitted from the at least one adherent device with the wireless communication circuitry to at least one gateway. The patient data is transmitted from the at least one gateway to a local processor system.

In many embodiments, the local processor system is configured to send customized alerts in response to the patient data.

In many embodiments, the at least one adherent device comprises a plurality of adherent devices in which each of the adherent devices comprises a unique device identifier, and the at least one gateway comprises a list of unique adherent device identifiers. The at least one gateway comprises a plurality of wireless communication gateways each having a unique gateway identifier and the list of unique adherent device identifiers, and a location of the patient is determined in response to the unique adherent device identifier and the unique gateway identifier when the patient is ambulatory.

In many embodiments, the patient data are transmitted with wireless communication from the at least one gateway to a local processor system. The at least one gateway can be carried by the at least one patient, for example hand held, on a belt, in a purse or with clothing of the patient.

The gateway can be configured in many ways to transmit the patient data to the processor system. At least one gateway may transmit the patient data directly to a transceiver of the local processor system. For example, each gateway of the plurality of gateways can be configured to communicate with a cellular connection to the transceiver of the local processor system. Alternatively or in combination, the at least one gateway may communicate with at least one other gateway with a mesh wireless communication protocol, such that the patient data can be transmitted indirectly from the gateway to the local processor system with the at least one other gateway.

In many embodiments, the method of monitoring a plurality of patients further comprises transmitting an emergency notification from one of the at least one adherent patient device in response to the patient operating an emergency notification switch on the adherent patient device to trigger the emergency notification transmission. The emergency notification can be transmitted to the at least one gateway, and the method can further comprise transmitting the emergency notification from the at least one gateway to the local processor system. Each adherent patient device can comprise a unique device identifier, and the patient-initiated emergency notification can comprise the unique device identifier. The method can further comprise indicating the originating adherent device by the local processor system in response to the received emergency notification. Each patient can have a unique identifier. The method can further comprise indicating by the local processor system in response to the received emergency notification at least one of the unique patient identifier, a name of the patient, an assigned room of the patient, or an assigned bed of the patient.

In another aspect, embodiments of the present invention provide a method of monitoring a plurality of patients. First patient data are transmitted from a first patient measurement device on a first patient to a first gateway with wireless communication. The first patient data are transmitted from the first gateway to a transceiver of a local processor system with a first wireless communication link. Second patient data from a second patient measurement device on a second patient are transmitted to a second gateway with wireless communication. The second patient data are transmitted from the second gateway to the first gateway in response to decoupling of the second gateway with the transceiver. The first gateway may transmit the second patient data to the transceiver of the local processor system with the first wireless communication link.

In many embodiments, the second gateway is initially coupled directly to the transceiver and decoupled from the second transceiver in response to movement of the second patient.

In another aspect, embodiments of the present invention provide a system to monitor a plurality of patients. A plurality of patient measurement devices is configured to measure patient data from a plurality of patients and transmit the patient data. A local processor system comprising a tangible medium and at least one display is disposed at a monitoring station. The local processor system comprises a transceiver configured to receive the patient data and display the patient data to a user at the monitoring station. A plurality of gateways is configured to receive the patient data from the plurality of patient measurement devices. Each gateway is configured to couple with at least one of the patient measurement devices and transmit the patient data to the local processor system. Each of the gateways is configured to couple directly with the transceiver of the processor system when the transceiver signal is suitable for coupling and to couple with another gateway of the plurality when the transceiver signal is weak.

The transceiver of the local processor system may be configured for placement at the monitoring station.

BRIEF DESCRIPTION OF THE DRAWINGS

FIG. 1A1 a patient monitoring system as in FIG. 1A configured to monitor patients admitted to a hospital ward;

FIG. 1A1-1 a patient monitoring system as in FIGS. 1A and 1A1, in which many of the patients carry hand held portable gateway configured to pair with the patient;

FIG. 1A2 shows the patient monitoring system of FIGS. 1A and 1A1 with a plurality of gateways, in which each gateway is configured to transmit data in response to a list of allowed patient devices;

FIG. 1A2-1 shows the patient monitoring system as in FIGS. 1A to 1A2, in which each gateway is configured to transmit data to the monitoring station with a wireless mesh networking standard in response to a list of allowed patient devices corresponding to patients of the ward.

FIG. 1A2-2 shows the patient monitoring system as in FIG. 1A2-1, in which the gateways establish communication with each other in response to a weak signal between a first gateway and the monitoring station.

FIG. 1A3 shows a master approved patient device list and corresponding gateway approved patient device lists for the patient monitoring system of FIGS. 1A and 1A2;

FIG. 1A3-1 shows a master approved patient device list and corresponding lists of allowed patient devices and allowed gateways for each gateway of the patient monitoring system as in FIGS. 1A-1 to 1A3;

FIG. 1A4 shows an updated master approved patient device list and corresponding updated gateway approved patient device lists for the patient monitoring system of FIGS. 1A, 1A1 and 1A2;

FIG. 1A4-1 shows an updated master approved patient device list and corresponding updated lists stored on the tangible medium of each gateway, in which each of the gateways is configured to communicate with the adherent devices of a plurality of patients and in which the gateways are configured to communicate with each other with a mesh network for the system as in FIGS. 1A to 1A4;

FIG. 1D shows a printed circuit boards and electronic components over the adherent patch, as in FIG. 1C;

FIG. 1D1 shows an equivalent circuit that can be used to determine optimal frequencies for determining patient hydration, according to embodiments of the present invention;

FIGS. 1I and 1J show a side cross-sectional view and an exploded view, respectively, of the adherent device as in FIGS. 1A to 1H;

FIG. 1K shows at least one electrode configured to electrically couple to a skin of the patient through a breathable tape, according to embodiments of the present invention;

FIG. 2 shows a method of monitoring patients, according to embodiments of the present invention; and FIG. 3 shows a method of monitoring patient data including the transmission of data from a plurality of patient worn devices with a plurality of gateways in response to an approved device list in accordance with the methods of FIG. 2.

FIG. 3-1 shows detail of the method of transmitting data from the gateway to the server as in FIG. 3.

DETAILED DESCRIPTION OF THE INVENTION

Figure 1A:
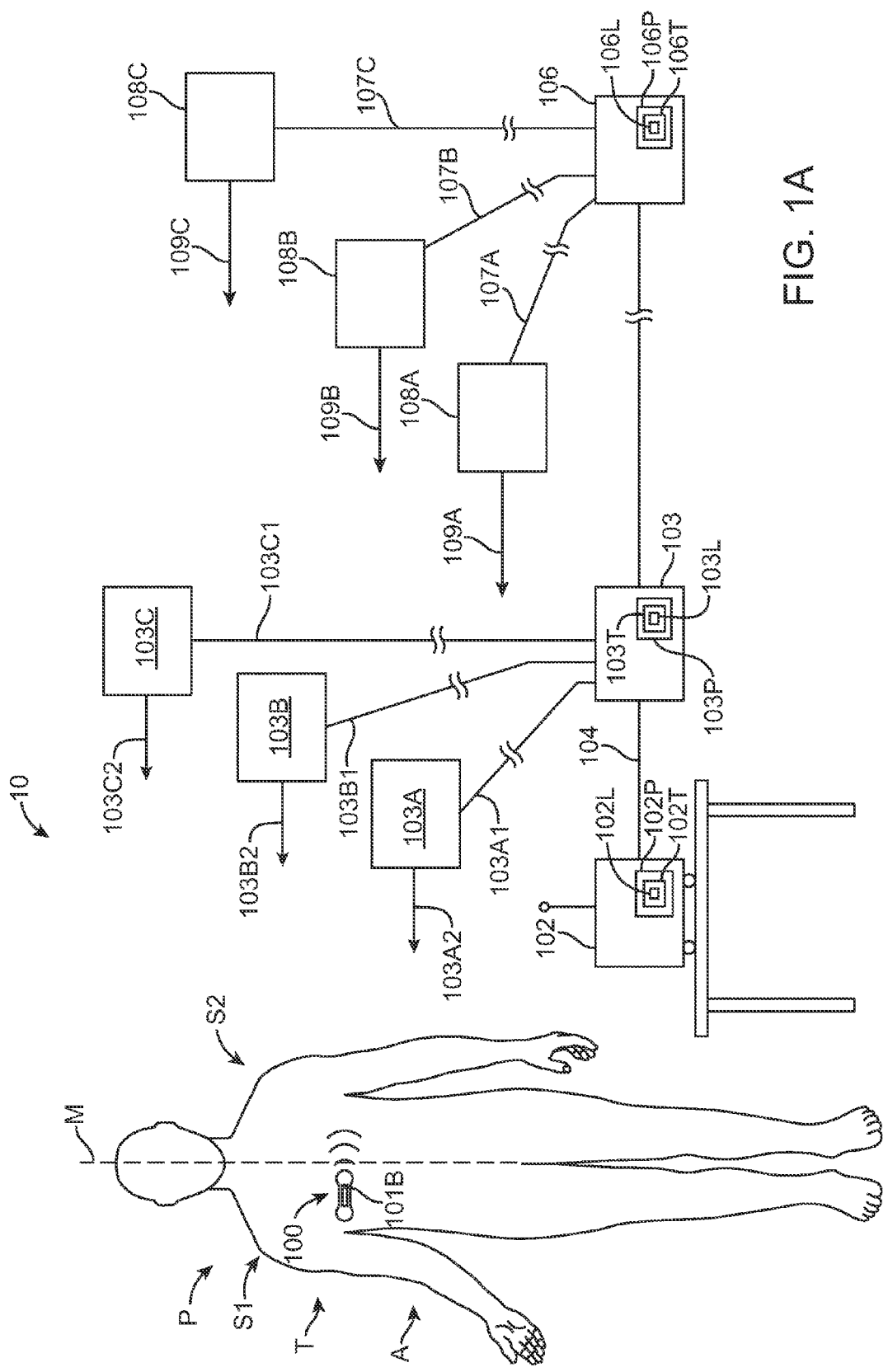
FIG. 1A shows a patient and a monitoring system for monitoring a plurality of patients, in which the monitoring system comprises adherent devices configured to adhere to the skin of the plurality of patients, according to embodiments of the present invention.

Embodiments of the present invention relate to patient monitoring. Although embodiments make specific reference to acute patient monitoring in a hospital, the system methods and device described herein may be applicable to any application in which physiological monitoring is used, for example wireless physiological monitoring for extended periods.

Embodiments comprise a system to monitor patients in a hospital ward with a dedicated wireless intranet. The system may comprise a monitoring station, for example a central monitoring station (CMS), and a plurality of patient measurement devices, for example a plurality of N adherent patient devices adhered to a plurality of N patients. The CMS may comprise a low power transceiver comprising a digital two way radio so as to communicate with the adherent patient devices. Each adherent patient device can measure patient physiological data such as heart rate, impedance based respiration, impedance based hydration and accelerometer signals, which are sent to the CMS. Each adherent patient device can be configured to pair with additional patient measurement devices, for example a weight scale, blood pressure cuff, and implanted measurement devices. The patients can be ambulatory and walk in the hospital ward with the adherent patch devices and transmit patient data to the CMS. At least some of the patients and the devices adhered to the patients may be out of range of the CMS radio. These out of range adherent devices can transmit data to the CMS through an adherent device that is in range of the CMS radio, for example with a first hop from the out of range adherent device to the in range adherent device and a second hop from the in range adherent device to the CMS. The adherent devices and CMS radio may comprise the dedicated intranet and may employ a known mesh protocol, for example ZigBee, which is the name of a specification for a suite of high level communication protocols using small, low-power digital radios based on the IEEE 802.15.4-2006 standard for wireless personal area networks (WPANs). Each of the adherent devices can be configured to dynamically change the route of the data from the adherent device to the monitoring station as the patients walk around the hospital.

Each patient may carry a gateway device that is separate from the adherent device, for example a belt worn device, in which each adherent device transmits patient data wirelessly from the adherent device to the gateway device on the patient and then with wireless communication from the gateway to the CMS. The communication from the gateway to the CMS may comprise direct communication with the CMS or indirect communication with the CMS. The gateway device of each patient that is within range of the CMS may communicate directly with the CMS, and the gateway device of each patient that is out of range of the CMS may communicate indirectly with the CMS using the gateway device of another patient that is in range of the CMS to transmit data to the CMS. Each of the adherent patient devices may comprise a unique device identifier transmitted with the patient data to identify the patient from whom that data originated, and each gateway device may comprise an unique gateway identifier to identify the communication route to the CNS. The adherent devices may comprise circuitry to locate the ambulatory patients, for example GPS circuitry, such that the patients are easy to find when a life threatening event occurs such as a heart attack.

Embodiments of the present invention comprise an in-hospital monitoring system, that can provide ICU-level monitoring to patients in general wards. A variety of physiological variables can be continuously monitored and provided to hospital staff with accompanying alerts/alarms. Depending on sensors of the device adhered to the patient, increasing monitoring levels can be provided from minimal monitoring, for example of a single patient variable such as heart rate, to advanced monitoring substantially similar intensive care ward monitoring. The system can provide a variety of customized alerts upon detection of a physiological event such as cardiac arrhythmias, heart failure status, renal disorders, low blood oxygen, fetal disorders. The system can also provide the ability for a monitored patient to initiate an emergency notification transmission from the adherent device by operating an emergency notification switch on the adherent device. The emergency notification switch can take many forms, for example, a mechanical switch, an electrical switch, an optical switch, a proximity sensor, a push button, a capacitive sensor, or many devices operable by the patient to generate a signal so as to trigger a transmission of an emergency notification from the adherent device. The patient-initiated emergency notification transmission can be processed by the system to generate an appropriate alert.

Although the system can be configured in many ways, the system components can include: an adherent patient device; a gateway device; an alarm; a central terminal; a front end server; and a back end server. The adherent patient device may comprise a patch of breathable material, for example breathable tape, such that the adherent patient device can be adherent to the patient with the patch of breathable material. The adherent patch can be configured to support the electronics circuitry for measuring patient data and communication circuitry to transmit that data when the patch is adhered to the patient.

The wireless adhesive patient device can be configured to be placed and adhered on the patient's chest with the patch. The patch device can comprise the capability to monitor at least one of the following physiological signals: heart rhythm, respiration, activity, and body fluid, pulse oximetry, or temperature. The adherent patient device can also comprise an emergency notification switch operable by the patient to trigger an emergency notification transmission from the adherent patient device.

The gateway device, which wirelessly communicates with the adherent patch device to download and transmit physiological data. Data transmission may occur via at least one of a wired phone line, internal hospital network (wireless or wired intranet), or internet (either wireless or wired).

Each gateway device can be configured to transmit data from the patient device to the backend server system at the remote site, for example through the front end server. The gateway may comprise a list of approved adherent patient devices. The data transmitted from the adherent patient device may be controlled with a list, for example a list of approved devices, to control the flow of data through the gateways and maintain integrity of the gateways. Each gateway can be stationary and configured to transmit a gateway identifier with the patient data, such that the patient can be located in response to the gateway identifier and the location of the gateway in the hospital.

The alarm device can be mounted on or around the outside of the patient's room, such that the alarm is visible and/or audible to hospital staff.

The central terminal can be placed, for example, at the ward's nurses' station. The central terminal can be web-enabled, and access patient data via a web browser. This terminal can be used to: 1) associate the patch device with the patient and/or with the patient's room/bed; 2) associate the patch device with the appropriate alarm targets: pager, cell phone, etc; 3) display the status of all patients in the ward, highlighting any relevant alerts; 4) display vital signs of monitored patients; and 5) display any patient emergency notification(s) transmitted from the adherent patient device(s). The central terminal may comprise the front end server.

The front end server can be located at the central terminal and can store patient data for the patients in the ward. The front end server may comprise a server with hospital data for the patients and can be in communication with additional servers that store patient data from other locations in the hospital, for example radiology and/or imaging data.

The backend server can receive patient data from the gateway, for example via the front end server, and perform data analysis. The back end server can issue alerts by communicating with the gateway device, central terminal, and/or alarm targets.

System deployment may occurs as follows. All rooms in a ward can be equipped with stationary gateway devices and alarm devices. When patients arrive in the ward, they can be issued a patch device with an individual serial number. The central terminal can be used to associate the patch device with the patient and/or with the patient's room/bed number. The patient device may also be associated with appropriate alarm targets (pager, cell phone, etc.) The patient device can be applied by hospital personnel to the patient's chest, and additional locations on the patient can be used. Data analysis can occur on at least one of the following: the adherent patient device, the gateway, the central terminal, and the backend server. When data analysis occurs primarily on the patient device, the data analysis may be of low computational intensity (for example, arrhythmia detection with a rate cutoff in the absence of activity).

The alerts may comprise one or more of the following. A light, beeper, and/or buzzer located on the adherent patient device. For example, the alarm may be manually deactivated with a button on the adherent patient device. A light, beeper, and/or buzzer located on the gateway device. The alarm may be manually deactivated with a button on the gateway device. A light, beeper, and/or buzzer can be located on the alarm device. The alarm may be manually deactivated with a button on the alarm device. A display, light, beeper, and/or buzzer can be located with the central terminal. The alerts can be issued to associated alarm targets. Additional alert targets can include a physician on call at the ward, and many specialists who may be on call, in response to the physiological signals measured with the adherent patient device.

The monitoring system and adherent patient device can be configured in many ways, based on the needs of the patient. In some embodiments, a dual patient device system can be employed with two or more adherent patient devices adhered to the patient, for example with patches device placed on opposite sides of the chest for enhanced data signal fidelity. The patch device, gateway, and/or central terminal may include a battery indicator and/or low battery alert when the stored energy of the battery of the patch device is low.

The system can be configured to locate the patient in the hospital. For example, the patch device may include a GPS receiver to allow for patch device localization, which may obviate a need to associate the patch device with a ward/room/bed. Also hospital-wide gateway network can be configured to allow patients to roam the hospital while being monitored, and the gateway network can be configured to locate the patient in response to pairing of the gateway with the patient.

The patient adherent device is configured to measure patient data. Many devices that transmit wireless data through a gateway can be incorporated with embodiments. For example, a gateway device can receive data from at least one patient worn device, for example a plurality of patient worn devices. Examples of patient worn devices that can be used to transmit wireless data include known wearable devices such as a Holter monitor or ambulatory electrocardiography device. The patient device may comprise one or more adherent devices simultaneously adhered to the patient, for example with a first adherent device adhered to a chest of the patient to measure patient physiology and a second adherent device adhered to a limb of the patient to measure patient movement, for example as described in U.S. Pat. App. No. 61/055,656, filed on May 23, 2008, entitled "Adherent Device for Sleep Disordered Breathing". The patient device may also comprise one or more of a plurality of patient worn device that are sequentially placed on the patient to measure physiologic status of the patient, for example as described in U.S. Pat. App. Nos. 60/972,537, filed on Sep. 14, 2007; 61/055,666, filed May 23, 2008; Ser. No. 12/209,288, filed Sep. 12, 2008; entitled "Adherent Device with Multiple Physiological Sensors". The patch device can be continuously adhered to the patient for an extended period of at least one week, for example for two weeks, when the patient is admitted to the hospital.

In specific embodiments, an adherent patient device comprises an adherent patch device which is configured to adhere to the skin of the patient with an adherent patch, for example breathable tape, to measure patient data. The device may comprise impedance circuitry coupled to at least four electrodes and can be configured to measure at least one of patient hydration or respiration, for example to detect sleep apnea and/or hypopnea. The impedance circuitry may be used to measure hydration of the patient, which can be useful evaluating the physiologic status of the patient, for example in combination with the detected sleep apnea and/or hypopnea. An accelerometer can be mechanically coupled to the adherent patch such that the accelerometer can be coupled to and move with the skin of the patient, thereby providing an accurate and reliable measurement of the orientation and/or activity of the patient, which can be helpful in determining that the patient is asleep. The accelerometer can be mechanically coupled to the adherent patch such that the accelerometer can detect motion of the jaw and/or legs. Electrocardiogram circuitry to generate an electrocardiogram signal may be coupled to at least two of the at least four electrodes, such that the sleep apnea and/or hypopnea can be detected in response to a heart rate variability from the electrocardiogram signal.

Embodiments of the present invention can be used to transmit important data relevant to patients with health conditions. For example, decompensation is failure of the heart to maintain adequate blood circulation. Although the heart can maintain at least some pumping of blood, the quantity is inadequate to maintain healthy tissues. Several symptoms can result from decompensation including pulmonary congestion, breathlessness, faintness, cardiac palpitation, edema of the extremities, and enlargement of the liver. Cardiac decompensation can result in slow or sudden death. Sudden Cardiac Arrest (hereinafter "SCA"), also referred to as sudden cardiac death, is an abrupt loss of cardiac pumping function that can be caused by a ventricular arrhythmia, for example ventricular tachycardia and/or ventricular fibrillation. Although decompensation and SCA can be related in that patients with decompensation are also at an increased risk for SCA, decompensation is primarily a mechanical dysfunction caused by inadequate blood flow, and SCA is primarily an electrical dysfunction caused by inadequate and/or inappropriate electrical signals of the heart.

The adherent patient device may be worn continuously for at least seven days, for example 14 days, and then replaced with another patch. Adherent devices with comfortable patches that can be worn for extended periods and in which patches can be replaced and the electronics modules reused are described in U.S. Pat. App. Nos. 60/972,537, entitled "Adherent Device with Multiple Physiological Sensors"; and 60/972,629, entitled "Adherent Device with Multiple Physiological Sensors", both filed on Sep. 14, 2007, the full disclosures of which have been previously incorporated herein by reference. In many embodiments, the adherent patch comprises a tape, which comprises a material, preferably breathable, with an adhesive, such that trauma to the patient skin can be minimized while the patch is worn for the extended period. The printed circuit board may comprise a flex printed circuit board that can flex with the patient to provide improved patient comfort.

FIG. 1A shows a patient P and a monitoring system 10 for monitoring a plurality of patients. Patient P comprises a midline M, a first side S1, for example a right side, and a second side S2, for example a left side. Monitoring system 10 comprises an adherent patient device 100. Adherent patient device 100 can be adhered to a patient P at many locations, for example thorax T of patient P. In many embodiments, the adherent device may adhere to one side of the patient, from which side data can be collected. Work in relation with embodiments of the present invention suggests that location on a side of the patient can provide comfort for the patient while the device is adhered to the patient. In some embodiments, the adherent patient device may have a rechargeable electronics module 101B, and may use dual battery and/or electronics modules, wherein one module can be recharged using a charging station while the other module is placed on the adherent patch with connectors. In some embodiments, the intermediate device 102 may comprise the charging module, data transfer, storage and/or transmission, such that one of the electronics modules can be placed in the intermediate device for charging and/or data transfer while the other electronics module is worn by the patient.

Monitoring system 10 includes components to transmit data to a local monitoring station 103 and a remote center 106. The local monitoring station 103 can be located in the hospital with the patient, for example at a nurses station comprising a central terminal. Remote center 106 can be located in a different building from the patient, for example in the same town as the patient, and can be located as far from the patient as a separate continent from the patient, for example the patient located on a first continent and the remote center located on a second continent. Adherent patient device 100 can communicate wirelessly to an intermediate device 102, for example with a single wireless hop from the adherent device on the patient to the intermediate device. Intermediate device 102 comprises a communication gateway. Intermediate device 102 comprising the communication gateway can communicate with remote center 106 with a connection 104 in many ways. For example, connection 104 may comprise at least one of an internet connection, a cellular connection, or a low power industrial science and medical (hereinafter "ISM") digital radio, for example ZigBee radio and protocol or Bluetooth radio and protocol.

In many embodiments, monitoring system 10 comprises a distributed processing system with at least one processor comprising a tangible medium of device 100, at least one processor 102P of intermediate device 102, and at least one processor 103P at local monitoring station 103, at least one processor 106P at remote center 106, each of which processors can be in electronic communication with the other processors. Each of the at least one processors may comprise a processor system. For example, at least one processor 102P may comprise a processor system, at least one processor 103P may comprise a processor system, and at least one processor 106P may comprise a processor system. At least one processor 102P comprises a tangible medium 102T, and tangible medium 102T may be configured so as to comprise a list 106L of approved devices and/or device identifiers. The list 106L is used to control and/or limit which adherent devices communicate with intermediate device 102. At least one processor 103P comprises a tangible medium 103T, and tangible medium 103T may be configured so as to comprise a master list 103L of approved device identifiers for each adherent device deployed on a patient in the hospital. At least one processor 106P comprises a tangible medium 106T, and tangible medium 106T may be configured so as to comprise a master list 106L of approved device identifiers, for several hospitals. The master list and/or components of the master list 103L and the master list 106L can be transmitted to tangible medium 102T from processor 106P so as to control which devices are allowed to communicate with intermediate device 102, which may comprise an intermediate gateway device.

Local processor 103P may comprise a front end server located at the monitoring station. Monitoring station 103 can be in communication with a health care provider 103A with a communication system 103A1, such as the Internet, an intranet, phone lines, wireless and/or satellite phone, a local area network, WiFi, ISM, BlueTooth, or ZigBee. Communication system 103A1 may comprise at least one of a pager device, a personal digital assistant, a cellular phone or an alarm, for example an alarm at the monitoring station. Health care provider 103A, for example a nurse or caregiver, can immediate physical access to patient P, for example by walking from the monitoring station to the patient's room, as indicated by arrow 103A2. Local monitoring station 103 can be in communication with a health care professional, for example a physician 103B located in the hospital, with a communication system 103B1, such as the Internet, an intranet, phone lines, wireless and/or satellite phone, a personal digital assistant, or a pager. Communication system 103B1 may comprise at least one of a pager device, a personal digital assistant, a cellular phone or an alarm, for example an alarm at the monitoring station. Physician 103B can have immediate access to patient P, for example by walking from the monitoring station to the patient's room. Local monitoring station 103 can be in communication with an emergency responder 103C, for example ICU personnel and code blue responders located in the hospital. A communication system 103C1 may be used to reach the emergency responder, and communication system 103C1 may comprise at least one of a pager device, a personal digital assistant, a cellular phone or an alarm, for example an alarm at the monitoring station. Emergency responder 108C can travel to the patient as indicated by arrow 103C2, for example to revive the patient. Thus, in many embodiments, monitoring system 10 comprises a closed loop system in which patient care can be monitored and implemented from the local monitoring station in response to signals from the adherent device.

Remote processor 106P may comprise a backend server located at the remote center. Remote center 106 can be in communication with a health care provider 108A with a communication system 107A, such as the Internet, an intranet, phone lines, wireless and/or satellite phone. Health care provider 108A, for example a family member, nurse or caregiver, can be in communication with patient P with a communication system, for example with a two way communication system, as indicated by arrow 109A, for example by cell phone, email, landline. Remote center 106 can be in communication with a health care professional, for example a physician 108B, with a communication system 107B, such as the Internet, an intranet, phone lines, wireless and/or satellite phone. Physician 108B can be in communication with patient P with a communication, for example with a two way communication system, as indicated by arrow 109B, for example by cell phone, email, landline. Remote center 106 can be in communication with an emergency responder 108C, for example a 911 operator and/or paramedic, with a communication system 107C, such as the Internet, an intranet, phone lines, wireless and/or satellite phone. Emergency responder 108C can travel to the patient as indicated by arrow 109C. Thus, in many embodiments, monitoring system 10 comprises a closed loop system in which patient care can be monitored and implemented from the remote center in response to signals from the adherent device.

In many embodiments, the adherent device may continuously monitor physiological parameters, communicate wirelessly with a remote center, and provide alerts when necessary. The system may comprise an adherent patch, which attaches to the patient's thorax and contains sensing electrodes, battery, memory, logic, and wireless communication capabilities. In some embodiments, the patch can communicate with the remote center, via the intermediate device in the patient's home. In some embodiments, remote center 106 receives the patient data and applies a patient evaluation algorithm, for example an algorithm to calculate the apnea hypopnea index. When a flag is raised, the center may communicate with the patient, hospital, nurse, and/or physician to allow for therapeutic intervention.

The adherent device may be affixed and/or adhered to the body in many ways. For example, with at least one of the following: an adhesive tape, a constant-force spring, suspenders around shoulders, a screw-in microneedle electrode, a pre-shaped electronics module to shape fabric to a thorax, a pinch onto roll of skin, or transcutaneous anchoring. Patch and/or device replacement may occur with a keyed patch (e.g. two-part patch), an outline or anatomical mark, a low-adhesive guide (place guide |remove old patch|place new patch|remove guide), or a keyed attachment for chatter reduction. The patch and/or device may comprise an adhesiveless embodiment (e.g. chest strap), and/or a low-irritation adhesive for sensitive skin. The adherent patch and/or device can comprise many shapes, for example at least one of a dog bone, an hourglass, an oblong, a circular or an oval shape.

System 10 can perform the following functions: initiation, programming, measuring, storing, analyzing, communicating, predicting, and displaying. The adherent device may contain a subset of the following physiological sensors: bioimpedance, respiration, respiration rate variability, heart rate (ave., min., max.), heart rhythm, heart rate variability (HRV), heart rate turbulence (HRT), heart sounds (e.g. S3), respiratory sounds, blood pressure, activity, posture, wake/sleep, orthopnea, temperature/heat flux, and weight. The activity sensor may comprise one or more of the following: ball switch, accelerometer, minute ventilation, HR, bioimpedance noise, skin temperature/heat flux, BP, muscle noise, posture.

The adherent device can wirelessly communicate with remote center 106. The communication may occur directly (via a cellular or Wi-Fi network), or indirectly through intermediate device 102. Intermediate device 102 may comprise multiple devices, which can communicate wired or wirelessly to relay data to remote center 106.

In many embodiments, instructions are transmitted from remote site 106 to a processor supported with the adherent patch on the patient, and the processor supported with the patient can receive updated instructions for the patient treatment and/or monitoring, for example while worn by the patient.

Figure 3:
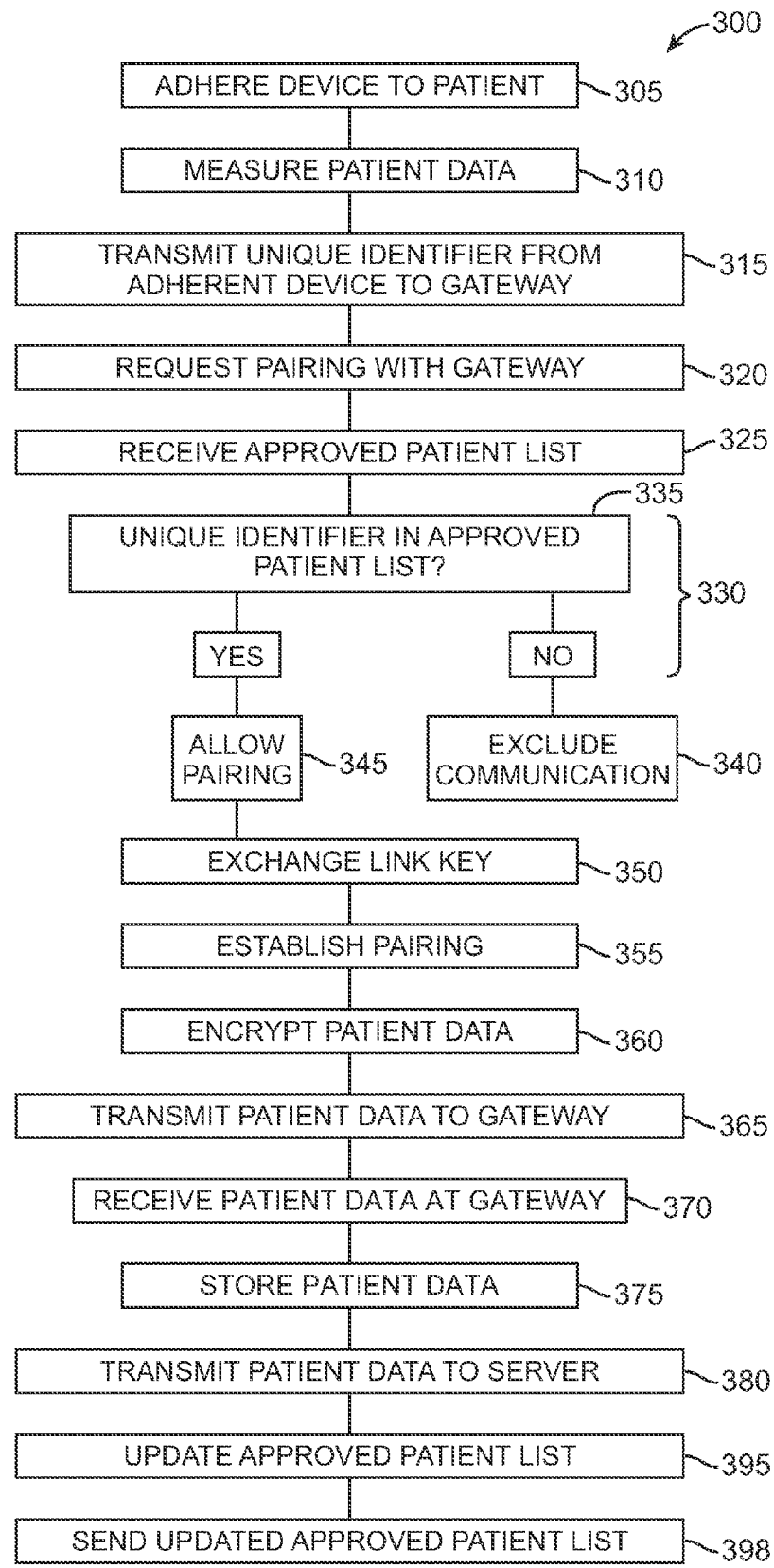
Figures 1, 3:
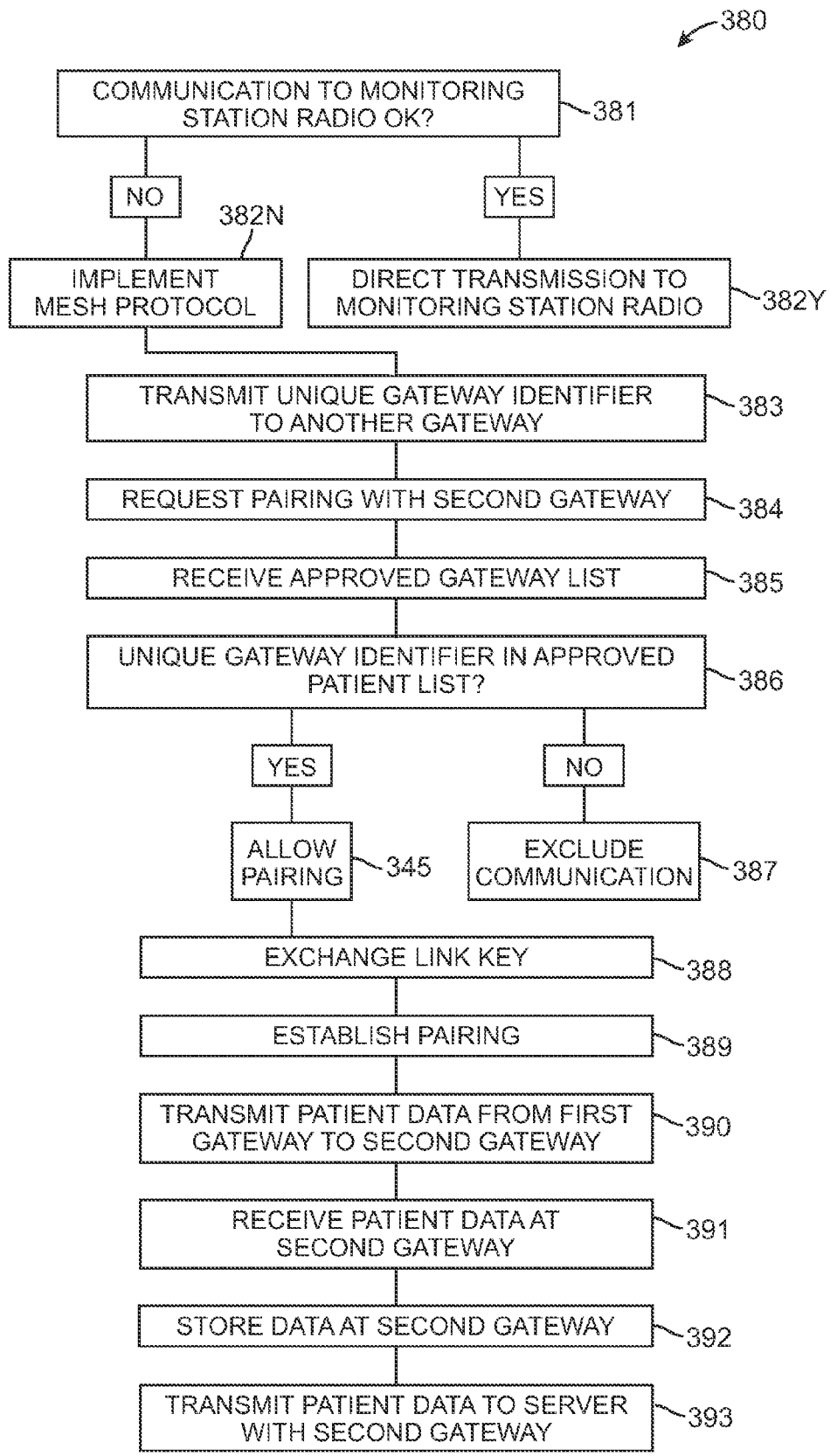

FIG. 1A1 shows a patient monitoring system 10 as in FIG. 1A configured to monitor patients admitted to a hospital ward HW. The patient P is shown ambulatory near local monitoring station 103, for example a nurses' central monitoring station. Local monitoring station 103 comprises a central terminal CT and the local processor 103P comprising the front end server, as described above. The front end server is configured to communicate with a plurality of adherent patient devices, such as such as adherent device 100. The central terminal CT comprises a plurality of central terminal displays CTD, which may comprise a plurality of computer displays, to show patient data from the adherent devices at the local monitoring station 103. The plurality of central displays may also be configured to display the status of the patient devices adhered to patients, for example configured to display at least one of a battery power level or a status of a connection of the device to the patient. The local processor 103P is coupled to the remote center 106 comprising the remote processor 106P, as described above.

The local monitoring station can be configured to admit patient P to the hospital ward and to associate adherent device 100 with patient P. A nurse N can use the processor system to admit patient P to the hospital ward. The local at least one processor 103P may comprise a processor system with the front end server and at least one hand held processor device 103HD, such as a personal digital assistant (hereinafter "PDA"), such that the nurse can admit the patient. The at least one hand held processor device 103HD may comprise a touch screen display, wireless communication circuitry to communicate with the adherent device and the front end server, and a processor comprising a tangible computer memory medium such as random access memory (hereinafter "RAM"), flash RAM, a hard drive and read only memory. For example nurse N can hold the at least one hand held processor device 103HD when patient P is admitted to the hospital, and the device 103HD held by the nurse can transmit a unique adherent device identifier when the adherent device is adhered to the patient. The at least one hand held processor device 103HD may comprise many known PDA devices such as at least one of an IPhone™, a Blackberry™, or a tablet PC.

The adherent patient device can be configured to pair with the at least one hand held processor device 103HD in response to the adherent device being adhered to the skin of the patient. For example, the adherent patient device can be configured to turn on when the patient device is adhered to the patient as described in U.S. 60/972,336; 61/046,196; Ser. Nos. 12/209,276; and 12/209,274; the full disclosures of which have been previously incorporated by reference. The pairing of the adherent patient device with the at least one hand held processor device 103HD can make it easier for the nurse to associate the adherent patient device with the patient, for example when the unique device identifier of the adherent patient device is transmitted with wireless communication from the patient device to the local processor system.

The nurse, or other hospital staff, can associate the adherent patient measurement device with the patient in many ways. For example, adherent device 100 may comprise a unique adherent device identifier such as a hexadecimal serial number, and serial number of the adherent device can be associated with the patient, for exampled keyed to the patient, such that the serial number of the adherent device corresponds to the patient. The unique adherent device identifier can be entered into the local processor system in many ways, for example by at least one of wireless communication from the adherent device, transmission from the back end server, optical scanning, radiofrequency identification (hereinafter "RFID"), data entry from a key board, or selection from a list. The patient may have a unique patient identifier, and the patient may be assigned the unique identifier when the patient is admitted to the ward or before. The unique patient identifier can be provided to the local processor system in many ways, for example similar to the unique adherent device identifier. The unique patient identifier can be used to associate the patient with at least some aspects of the ward, for example the room of the patient, the gateway of the patient and the bed of the patient. As the adherent device identifier is unique, the alerts can be based on the adherent device and may also be based on the unique patient identifier, such as a unique hexadecimal number.

The patient specific alerts sent in response to patient data from the patch can be customized, for example at the monitoring station. The customized alerts can include alerts from the backend end server of the remote center, and also alerts from the monitoring station. For example, the local processor system can include a calendar of physician schedules, and can automatically update the alert to the physician who is present at the ward. The alert can also be customized based on the condition of the patient. For example, when the patient is diagnosed to have heart trouble or suspected heart trouble, the alter can be customized to alert a cardiologist, for example a cardiologist who present at the hospital based on the physician schedules and date and time. The processor system can also be configured to alert a treating physician in response to the kind of problem the patient has. For example if the patient shows edema in response to impedance measurements, a nephrologist can be sent an alert in response to the change in tissue resistance, for example a decrease. As a decrease in tissue resistance can also indicate an impending cardiac decompensation the cardiologist who is present at the hospital of the ward can be sent an alert in response to the measured decrease in tissue resistance.

The general ward includes a plurality of patient rooms, for example room R1, room R2, room R3, room R4, room R5 and room R6. Each room may comprise at least one patient bed, for example two beds. Room R1 comprises a first bed B1A and a second bed BIB. Room R2 comprises a first bed B2A and a second bed B2B. Room R3 comprises a first bed B3A and a second bed B3B. Room R4 comprises a first bed B4A and a second bed B4B. Room R5 comprises a first bed B5A and a second bed B5B. Room R6 comprises a first bed B6A and a second bed B6B. At least one gateway may be located in each room. For example, room R1 may have a gateway 102A. Room R2 may have a gateway 102B. Room R3 may have a gateway 102C. Room R4 may have a gateway 102D. Room R5 may have a gateway 102E. Room R6 may have a gateway 102F.

An alarm can be located for each room and coupled to each gateway. For example, an alarm A1 can be located at the entrance to room R1 and coupled to gateway 102A. An alarm A2 can be located at the entrance to room R2 and coupled to gateway 102B. An alarm A3 can be located at the entrance to room R3 and coupled to gateway 102C. An alarm A4 can be located at the entrance to room R4 and coupled to gateway 102D. An alarm A5 can be located at the entrance to room R5 and coupled to gateway 102E. An alarm A6 can be located at the entrance to room R6 and coupled to gateway 102F.

Each of the alarms may have a patient specific alert associated with the patient assigned to a bed in the ward, for example alarm A1 can have a patient specific alert A1A for the patient assigned to bed B1A, and a patient specific alert A1B for the patient assigned to bed BIB. Alarm A2 can have a patient specific alert A2A for the patient assigned to bed B2A, and a patient specific alert A2B for the patient assigned to bed B2B. Alarm A3 can have a patient specific alert A3A for the patient assigned to bed B3A, and a patient specific alert A3B for the patient assigned to bed B3B. Alarm A4 can have a patient specific alert A4A for the patient assigned to bed B4A, and a patient specific alert A4B for the patient assigned to bed B4B. Alarm A5 can have a patient specific alert A5A for the patient assigned to bed B5A, and a patient specific alert A5B for the patient assigned to bed B5B. Alarm A6 can have a patient specific alert A6A for the patient assigned to bed B6A, and a patient specific alert A6B for the patient assigned to bed B6B. Each of the alarms may comprise a switch, for example a button, to manually deactivate the alarm device, for example a button on each of alarm A1, A2, A3, A4, A5 and A6.

Each of the patients may be ambulatory, and system 10 can be configured to monitory ambulatory patients, such that the ambulatory patient can be located and the data can be transmitted to the front end server in a controlled manner. Patient PA can be assigned to bed B1A of room R1, and gateway 102A can be configured to pair with patient PA. Patient PD can be assigned to bed B2A of room R2, and gateway 102B can be configured to pair with patient PB. Patient PC can be assigned to bed B3A of room R3, and gateway 102C can be configured to pair with patient PC. Patient PD can be assigned to bed B4A of room R4, and gateway 102D can be configured to pair with patient PD. Additional gateways and beds can be similarly assigned to patients admitted to the ward.

The unique identification number of each adherent patient device can be used to locate each ambulatory patient in the ward, and each adherent device can be configured to pair with more than of the gateways in the ward to transmit patient data when the patient wanders about the ward. For example, the adherent patient devices and the gateways can each be configured to include the unique identifier, and each adherent device can be configured to pair with the nearest allowed gateway with the strongest signal when the patient wanders out of range of a paired gateway. Patient PA is shown wearing adherent device 100A1 configured to pair with gateways 102A, 102B and 102C. When patient PA is nearest gateway 102A of allowed gateways 102A, 102B and 102C, adherent device 102A1 can pair with gateway 102A. Patient PB is shown wearing adherent device 100B1 configured to pair with gateways 102A, 102B and 102C. When patient PB is nearest gateway 102B of allowed gateways 102A, 102B and 102C, adherent device 102B1 can pair with gateway 102B. Patient PC is shown wearing adherent device 100C1 configured to pair with gateways 102A, 102B and 102C. When patient PC is nearest gateway 102B of allowed gateways 102A, 102B and 102C, adherent device 102C1 can pair with gateway 102B. Patient PD is shown wearing adherent device 100D1 configured to pair with gateways 102D, 102E and 102F. When patient PD is nearest gateway 102F of allowed gateways 102E, 102F and 102G, adherent device 102D1 can pair with gateway 102F. For example, patient PD can undergo cardiac arrest requiring immediate resuscitation, and can be located near gateway 102F based on the unique gateway identifier transmitted from patch 100D1 and the unique adherent device identifier corresponding to adherent device 100D1 which is associated with patient PD. The at least one processor 103P, for example of the front end server, can trigger an alarm at alarm A6 corresponding to a code blue alarm, and monitoring station 103 can display an alarm and the location of patient PD near gateway 102F of room R6, even though the patient has been assigned to room R4. The cardiologist on call for patient PD, ICU staff, and other alert targets can also be notified with alerts when the code blue alarm is triggered for patient PD, for example with a customized alert configured when the patient is admitted to the hospital ward.

FIG. 1A1-1 a patient monitoring system as in FIGS. 1A and 1A1, in which many of the patients carry hand held portable gateway configured to pair with the patient. The portable hand held gateways can be carried in many ways by the patient, for example with wrist band, attached to a belt, in a purse, or on a strap around the patient's wrist. Gateway 102A comprises a portable hand held gateway that patient 100A can carry. Gateway 102B comprises a portable hand held gateway that patient 100B can carry. Gateway 102C comprises a portable hand held gateway that patient 100C can carry. Gateway 102D comprises a portable hand held gateway that patient 100D can carry. Patient 100D is shone lying prone and having fallen and dropped his gateway 102D, such that patient 100D requires urgent care. As some parts of the ward may have walls that include metal, steel and rebar, the gateways can switch to a mesh network protocol to transmit the patient data to the monitoring station 103 when a direct wireless link to transceiver located at the monitoring station is not available.

Monitoring station 103 may comprise wireless communication circuitry 103WC configured to communicate with the portable handheld gateways. Wireless communication circuitry 103C comprises a transceiver configured to communicate with the gateways. Wireless circuitry 103C is coupled to at least one processor 103P located near the monitoring station. For example, wireless communication circuitry 103C can be located in the same room as monitoring station 103 and at least one processor 103P of the front end server, such that wireless communication circuitry 103C can be readily connected to the processor of the monitoring station.

Figure 2:
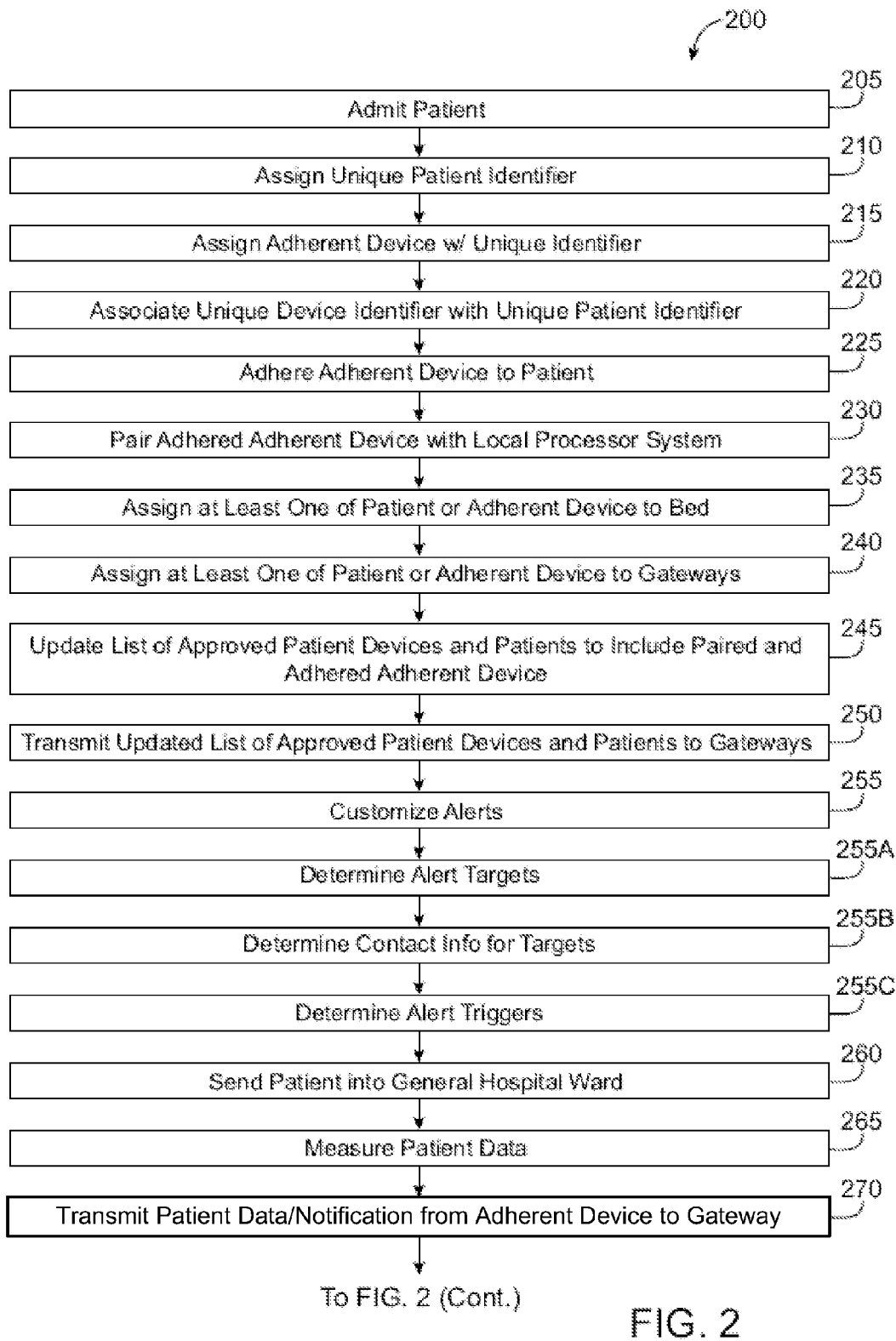
Figure 2:
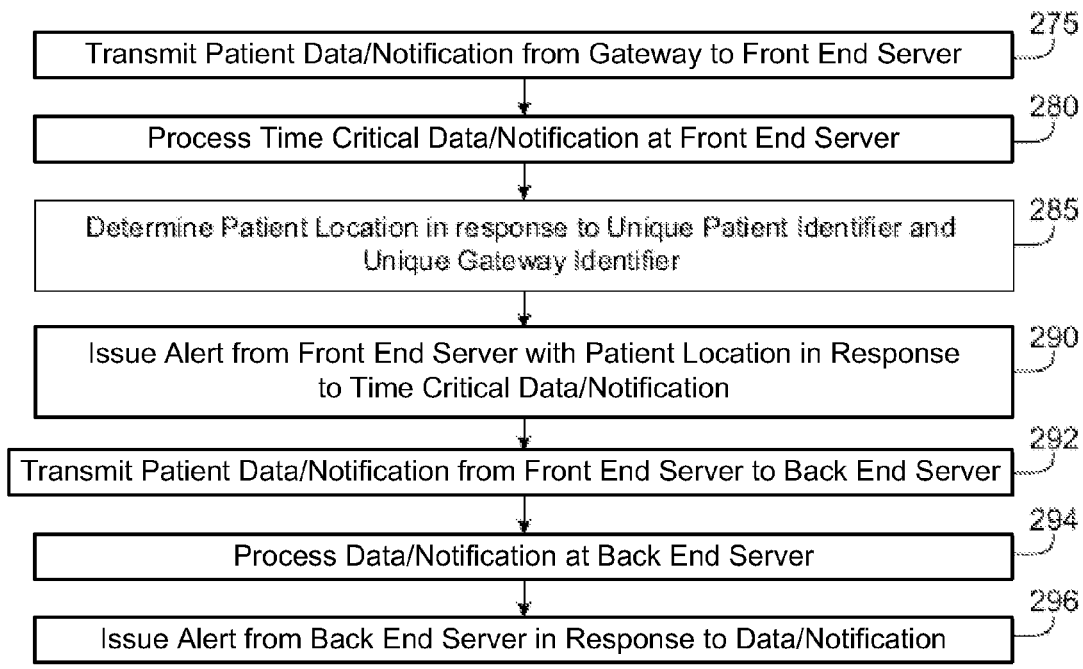

FIG. 1A2 shows monitoring a plurality of patients with monitoring system 10. The plurality of patients comprises at least two patients, for example a first patient PA, a second patient PB, a third patient PC and a fourth patient PD. Each of the plurality of patients has at least one device adhered or implanted into the patient to measure patient data. Intermediate device 102 comprises a plurality of at least two intermediate devices, for example a first intermediate device comprising a first gateway 102A, a second intermediate device comprising a second gateway 102B, a third intermediate device comprising a third gateway 102C; and a fourth intermediate device comprising a fourth gateway 102D. Each of the plurality of intermediate devices may comprise an approved patient device list that controls communication of the device with the gateway. For example first gateway 102A comprises a first approved device list 102AL. Second gateway 102B comprises a second approved device list 102BL. Third gateway 102C comprises a third approved device list 102CL. Fourth gateway 102D comprises a fourth approved device list 102DL. Each gateway allows the patient device to communicate with the back end server system at the remote center 106 when the device is on the approved device list, and each gateway may exclude communication with the backend server system at the remote center 106 when the patient device is not identified on the approved device list for the gateway. Remote center 106 comprises a master approved device 106L list that comprises each patient device approved for each gateway.

Each gateway may comprise a processor comprising a tangible medium configured to determine when the device is on the approved patch list. For example, first gateway 102A comprises a first processor 102AP. Second gateway 102B comprises a second processor 102BP. Third gateway 102C comprises a third processor 102CP. Fourth gateway 102D comprises a fourth processor 102DP.

Each of gateways 102A, 102B, 102C and 102D can send data to remote center 106 through each of connections 104A, 104B, 104C and 104D, respectively. Connections 104A, 104B, 104C and 104D may be, for example, a wireless connection, a cellular connection, a ZigBee connection, a Blue-Tooth connection, an Internet connection, an intranet connection, a wired connection, a cable connection or the like. The connection between the gateway and the backend server may comprise a dedicated connection when the gateway is paired to the adherent patient device, for example a dedicated cellular connection from a phone number dialed by the gateway.

More than one patient device can correspond to each patient. For example, a box of adherent patches can be provided for each patient, and each patch may comprise a unique identifier which is associated with the patient so as to correspond to the patient. The adherent patches can be adhered to the patient sequentially. For example, a first patch may be replaced after about one week with a second patch from the box. In some embodiments, a patient may have more than one patch simultaneously adhered to the patient, for example to measure data at two or more separate locations on the patient.

System 10 comprises a first plurality of patches for first patient PA, a second plurality of patches for second patient PB, a third plurality of patches for patient PC and a fourth plurality of patches provided for patient PD. The first plurality of adherent devices comprises adherent devices 100A1, 100A2, 100A3 and 100A4. Each of adherent devices 100A1, 100A2, 100A3 and 100A4 are configured to adhere to a patient, for example patient PA. The second plurality of adherent devices comprises adherent devices 100B1, 100B2, 100B3 and 100B4. Each of adherent devices 100B1, 100B2, 100B3 and 100B4 are configured to adhere to a patient, for example patient PB. The third plurality of adherent devices comprises adherent devices 100C1, 100C2, 100C3 and 100C4. Each of adherent devices 100C1, 100C2, 100C3 and 100C4 are configured to adhere to a patient, for example patient PC. The fourth plurality of adherent devices comprises adherent devices 100D1, 100D2, 100D3 and 100D4. Each of adherent devices 100D1, 100D2, 100D3 and 100D4 are configured to adhere to adhere to a patient, for example patient PD.

As noted above, each adherent device may have a device identifier, for example a unique device identifier such as a serial number. The device identifier can be transmitted with the patient data so as to allow the remote server system to identify the device. The device identifier may be encrypted. The adherent devices can be manufactured with a device identifier built into them, for example a device identifier stored in EPROM or non-volatile storage.

Each of gateways 102A, 102B, 102C, and 102D may each include an approved patient device list, such as a list of approved patient device serial numbers, and/or range of approved patient device identifiers. Each adherent patient device may transmit the device identifier to any gateway within range of the wireless communication signal transmitted by the adherent device.

When a specific adherent device is in the list and/or within the range of device identifiers of a specific gateway, the gateway can "pair" to the specific adherent device, such that data is transmitted from the adherent device to the backend server system at remote center 106. For example, patient data from one of the adherent devices can be transmitted to remote center 106, which may comprise the backend server or system. When the patient device is paired to the gateway, the gateway can provide a dedicated connection to from the gateway to the backend server system, such that the communication channel integrity is maintained.

Each device can pair with at least one of the gateways, in response to the approved list of the gateway. Each of adherent devices 100A1, 100A2, 100A3 and 100A4 may pair with the intermediate device comprising gateway 102A with pairing 100A1P, 100A2P, 100A3P and 100A4P, respectively, in response to approved patient device list 102AL. As noted above, the pairing can be sequential, for example when one of the adherent devices replaces a prior adherent device after an extended period of about one week. Each of adherent devices 100B1, 100B2, 100B3 and 100B4 may pair with the intermediate device comprising gateway 102B with pairing 100B1P, 100B2P, 100B3P and 100B4P, respectively, in response to approved patient device list 102BL. Each of adherent devices 100C1, 100C2, 100C3 and 100C4 may pair with the intermediate device comprising gateway 102C with pairing 100C1P, 100C2P, 100C3P and 100C4P, respectively, in response to approved patient device list 102CL. Each of adherent devices 100D1, 100D2, 100D3 and 100D4 may pair with the intermediate device comprising gateway 102D with pairing 100D1P, 100D2P, 100D3P and 100D4P, respectively, in response to approved device list 102DL.

Each of the adherent devices can communicate with the backend server when paired to the intermediate device comprising the gateway. Each of adherent devices 100A1, 100A2, 100A3 and 100A4 may be in paired electronic communication with the intermediate device comprising gateway 102A and transmit data to the backend server at remote center 106 when paired. Each of adherent devices 100B1, 100B2, 100B3 and 100B4 may be in sequential paired electronic communication with the intermediate device comprising gateway 102B and transmit data to the backend server at remote center 106 when paired. Each of adherent devices 100C1, 100C2, 100C3 and 100C4 may be in sequential paired electronic communication with the intermediate device comprising gateway 102C and transmit data to the backend server at remote center 106 when paired. Each of adherent devices 100D1, 100D2, 100D3 and 100D4 may be in electronic communication with the intermediate device comprising gateway 102D and transmit data to the backend server at remote center 106 when paired.

Although the pairing of the patient device to the gateways can occur in many ways, the protocol for pairing of each of the adherent devices with each of the gateways can be similar. For example, when adherent patient device 100A1 communicates with gateway 100A, adherent patient device 100A1 can be configured transmits its serial number SN to gateway 100A. The processor of gateway 102A may query approved device list 102AL and performs logic operations. If the serial number of device 100A is in the approved patient list 102AL, then device 100A will be allowed to pair with gateway 102A to send data to remote center 106. When the serial number of device 100A is not in the approved patient list 102AL, device 100A is excluded from pairing with gateway 102. In many embodiments, when device 100A pairs with gateway 102 to send data to remote center 106, gateway 102 adds the device identifier of device 100A to a packet of data from gateway 102 so that remote center 106 detect pairing between device 100A and gateway 102. Similar protocols can be used to transmit data for additional patient devices and gateways.

As the pairing of each device with the gateway is controlled with the approved patient device list, one intermediate device can be allowed to communicate with a plurality of patient devices for a plurality of patients. For example, the second intermediate device comprising second gateway 102B can be configured to communicate with device 100A1 when approved device list 102BL comprises the identifier for device 100A1 for first patient PA. The first intermediate device comprising first gateway 102A can be configured to communicate with device 100B1 when approved device list 102AL comprises the identifier for device 100B1 for second patient PB. With such a configuration, patient devices 100C1-100C4 for patient PC and patient devices 100D1-100D4 for patient PD can be excluded from paired communication the first intermediate device comprising gateway 102A and the second intermediate device comprising gateway 102B. Such configurations can be helpful when patients are mobile, for example in a ward of a hospital where many patient devices can be within range of a gateway device.

The gateways configured to pair with devices in response to the approved patch list allows for great flexibility in controlling the communication. For example, the adherent device can be paired to either zero or one gateway, in response to the approved patch list at each gateway, while a single gateway may be paired with many adherent patches. For example, a gateway using a Bluetooth connection may have at least 8 simultaneous connections for 8 adherent devices from 8 patients. The adherent patient device may actively search for a gateway to pair with, for example by searching and sorting gateway signals from strongest to weakest and stopping the search process when the adherent patient device has paired with the gateway with the strongest signal and in which the approved device list allows communication.

The gateways configured to pair with devices in response to the approved patch list allows for the communication to be controlled dynamically with dynamic updating of the approved device list. For example gateway 102A may comprise an approved device list 102AL which may be sent from remote center 106 or another server through two-way connection 104A. Approved device list 102AL may comprise, for example, a binary file, a hexadecimal file, an ASCII file or an encrypted file stored on tangible medium. Approved device list 102AL may comprise a list of serial numbers of approved adherent devices. Approved device list 102AL can be dynamic. For example, the list of serial numbers of approved adherent devices of list 102AL may change and/or be updated at any time, for example, with instructions from the backend server located at remote center 106. List 102AL may be sent from remote center 106 at any time to instruct a gateway 102A as to which adherent devices to pair with. For example, the list can be updated when a new patch is applied to a patient and/or when a patient is supplied with a box of adherent devices. In some instances, the gateway can be located in the patient's home and the list updated when the patient is sent home with a box of patches and gateway.

Each of gateways 102A, 102B, 102C, and 102D may have its own device identifier, for example a unique device identifier such as a serial number. The device identifier may be encrypted. Gateways 102A, 102B, 102C, and 102D can be manufactured with a device identifier built into them, for example a device identifier stored in EPROM or non-volatile storage. An adherent device and a gateway may be configured to exchange a link key so as to pair the gateway with the patient device.

Although FIG. 1A2 shows four patients PA, PB, PC and PD, each with a set of four adherent devices configured to attached to him or her, many patients, for example at least 100 patients, and many gateways, for example at least 25 gateways, may be provided.

FIG. 1A2-1 shows the patient monitoring system of FIGS. 1A to 1A2, in which each gateway is configured to transmit patient data to the monitoring station with a wireless mesh networking standard in response to a list of allowed patient devices corresponding to patients of the ward. Gateway 102A is configured couple to wireless communication circuitry 103WC of monitoring station with direct wireless communication 104A1. Gateway 102B is configured couple to wireless communication circuitry 103WC of monitoring station with direct wireless communication 104B1. Gateway 102C is configured couple to wireless communication circuitry 103WC of monitoring station with direct wireless communication 104C1. Gateway 102D is configured couple to wireless communication circuitry 103WC of monitoring station with direct wireless communication 104D1.

The direct wireless communication may comprise at least one of direct cellular communication or indirect communication with a mesh protocol. For example each of gateway 104A, gateway 104B, gateway 104C and gateway 104D can be configured to establish a cellular connection, which can be beneficial when direct communication is available and high data transmission rate throughput is beneficial. Alternatively or in combination, each of gateway 104A, gateway 104B, gateway 104C and gateway 104D can be configured to establish a mesh network to transmit data to monitoring station 103, such that at least some of the data transmission comprises indirect communication from one gateway to at least one other gateway and from the at least one other gateway to the transceiver of the monitoring station. The mesh network protocol can be beneficial when a cellular connection may not be available, and in situations where data transmission rate is not critical.

The mesh network protocol can establish communication among the gateways with connections extending between the gateways. Wireless mesh network communication can include direction communication from one gateway to another. The mesh network protocol may comprise bidirectional communication, for example such that the adherent devices can receive instructions to collect and transmit data from at least one of the monitoring station or the back end server. A wireless connection 104BA may extend from gateway 102B to gateway 102A. A wireless connection 104CB may extend from gateway 102C to gateway 102B. A wireless connection 104DC may extend from gateway 102D to gateway 102C. Additional connections can be established among the gateways, for example with a ZigBee protocol.

FIG. 1A2-2 shows the patient monitoring system as in FIG. 1A2-1, in which the gateways establish communication with each other in response to a weak signal between a first gateway and the monitoring station. Direct connection 104C1 is not available to gateway 102C, for example due to a weak signal, for example due to the patient wandering out of range or an obstruction such as a wall with steel or substantial multipath interference. Gateway 102C establishes communication with gateway 102B in response to the weak signal. Connection 104BC is shown established between gateway 102B and gateway 102C.

The mesh network can be configured for many wireless connections among the gateways to transmit patient data to the monitoring station. For example, if a direct communication with circuitry 103WC is not available to gateway 102B, gateway 102B can transmit patient data from gateway 102C to gateway 102A. Alternatively or in combination, gateway 102C may establish communication directly with gateway 102A and transmit patient data from patient PC directly to gateway 102A.

FIG. 1A3 shows master approved patient device list 106L and first approved patient device list 102AL transmitted to first gateway 102A, second approved patient device list 102BL transmitted to second gateway 102B, third approved patient device list 102CL transmitted to third gateway 102C, and fourth approved patient device list 102DL transmitted to fourth gateway 102D. The master approved patient device list 106L may comprise a field for each of a unique patient identifier, unique patient device identifier and a unique gateway identifier. The master list may comprise an entry with the unique patient device identifier, the unique gateway identifier and the unique patient device identifier for each patient device, for example patient PTA with patient device 100A1 and gateway 102A.

Connections from the backend server at the remote site can update the list at each gateway to dynamically control communication with the patient devices at each gateway. The backend server at remote center 106 can use connection 104A from remote center 106 to gateway 102A to dynamically update list 102AL at gateway 102A. Connection 104B from remote center 106 to gateway 102B can similarly be used to dynamically update list 102BL at gateway 102B. Connection 104C from remote center 106 to gateway 102C can also be used to dynamically update list 102CL at gateway 102C. The backend server at remote center 106 can use connection can also use connection 104D from remote center 106 to gateway 102D to dynamically update list 102DL at gateway 102D.

As shown in FIG. 1A3, one entry may include: a unique patient identifier PTA associated with a unique device identifier 100A1 and a unique gateway identifier 102A. Other entries include: a unique patient identifier PTA associated with a unique device identifier 100A2 and a unique gateway identifier 102A; a unique patient identifier PTA associated with a unique device identifier 100A3 and a unique gateway identifier 102A; a unique patient identifier PTA associated with a unique device identifier 100A4 and a unique gateway identifier 102A; a unique patient identifier PTB associated with a unique device identifier 100B1 and a unique gateway identifier 102B; a unique patient identifier PTB associated with a unique device identifier 100B2 and a unique gateway identifier 102B; a unique patient identifier PTB associated with a unique device identifier 100B3 and a unique gateway identifier 102B; a unique patient identifier PTB associated with a unique device identifier 100B4 and a unique gateway identifier 102B; a unique patient identifier PTC associated with a unique device identifier 100C1 and a unique gateway identifier 102C; a unique patient identifier PTC associated with a unique device identifier 100C2 and a unique gateway identifier 102C; a unique patient identifier PTC associated with a unique device identifier 100C3 and a unique gateway identifier 102C; a unique patient identifier PTC associated with a unique device identifier 100C4 and a unique gateway identifier 102C; a unique patient identifier PTD associated with a unique device identifier 100D1 and a unique gateway identifier 102D; a unique patient identifier PTD associated with a unique device identifier 100D2 and a unique gateway identifier 102D; a unique patient identifier PTD associated with a unique device identifier 100D3 and a unique gateway identifier 102D; and a unique patient identifier PTD associated with a unique device identifier 100D4 and a unique gateway identifier 102D.

The approved patient device lists and the master list can be configured in many ways. For example, the approved patient device list at each gateway may comprise master approved device list 106L such that the list at each gateway is the same and the processor at each gateway compares the gateway identifier to the patients on the master list that correspond to the gateway identifier.

As shown in FIG. 1A3, the approved patient device list at each gateway may include the unique patient device identifiers and a unique patient identifier. Gateway 102A comprises list 102AL. List 102AL comprises unique device identifiers 100A1, 100A2, 100A3, and 100A4 for each device given to the patient corresponding to unique patient identifier PTA. Gateway 102B comprises list 102BL. List 102BL comprises unique patient device identifiers 100B1, 100B2, 100B3, and 100B4 for each device given to the patient corresponding to the unique patient identifier PTB. Gateway 102C comprises list 102CL. List 102CL comprises the unique patient device identifiers 100C1, 100C2, 100C3, and 100C4 for each device given to the patient corresponding to the unique patient identifier PTA. Gateway 102D comprises list 102DL. List 102DL comprises unique patient device identifiers 100D1, 100D2, 100D3, and 100D4 for each device given to the patient corresponding to the unique patient identifier PTD.

In some embodiments, the adherent patient devices may comprise a digital communication protocol similar ZigBee, which forms a web or mesh of devices, such that the patient wireless data can hop from one adherent device to a neighboring adherent device and then to a gateway to transmit patient data. When the data transmission hops through intermediate neighboring adherent devices, the unique identifier of each intermediate adherent device through which the data travels can be appended to the data packet such that the location of the patient can be determined based on the unique adherent device identifiers and the gateway identifiers of the adherent devices and gateways through which the data is sent to the front end server. At least some of the adherent patient devices, for example intermediate devices, may include a GPS device to determine the location of the patient from whom the data originated.

The gateways may also comprise mobile gateways such that each patient can carry his or her gateway when walking. The mobile gateway may transmit the patient data wirelessly to the front end server. The adherent device may include a GPS device to determine the location of the patient from whom the data originated.

FIG. 1A3-1 shows a master approved patient device list and corresponding lists of allowed patient devices and allowed gateways for each gateway of the patient monitoring system as in FIGS. 1A-1 to 1A3. The list stored on the tangible medium of each gateway may be configured such that the gateways can communicate with each other in a mesh network configuration. List 102AL includes a list of allowed gateways. The list of allowed gateways may include a unique gateway identifier for each gateway of the monitoring system, or selected gateways of the monitoring system. The processor of the gateway may be configured to communicate only with the gateways on the list, such that communication among the gateways can be limited such that the integrity of the network can be maintained. For example, the gateways can be configured as a mesh network in response to the list. List 102AL includes unique gateway identifiers corresponding to gateways 102B, 102C and 102D. List 102BL includes unique gateway identifiers corresponding to gateways 102A, 102C and 102D. List 102CL includes unique gateway identifiers corresponding to gateways 102A, 102B and 102D. List 102DL includes unique gateway identifiers corresponding to gateways 102A, 102B and 102C. Each of the gateway may communicate with any gateway on the list.

The lists comprising the unique patient device identifiers and unique gateway identifiers can be used with the gateways, such that the configuration of the network can be controlled with great flexibility. As each of the gateways can communicate with the patient devices and other gateways in response to the list, the list stored on the tangible medium at each gateway can be updated so that the configuration of the network can be controlled with great flexibility. As the unique patient device identifier list of each gateway may correspond to one patient, each patient may have his or her own gateway to transmit patient data. The pairing of the gateways to each other may also be controlled with the list. For example, the list can be configured such that the gateways cannot communicate with each other and so that each gateway transmits patient data directly to the monitoring station.

FIG. 1A4 shows master list 106L updated to a second configuration from a first configuration shown in FIG. 1A3, so as to accommodate additional devices and/or to remove devices from the list and to disable communication of the devices removed from the list. The list at each gateway can be updated in response to the updated master list. There may be more than one unique patient device identifier for a given unique patient identifier, and there may be only one unique patient device identifier for a given unique patient identifier.

Master list 106L can be updated to allow a plurality of patient devices to communicate with each gateway, for example four patient devices. For example, entries of the updated master approved patient device list 106L may include: a unique patient identifier PTA, a unique device identifier 100A1, and a unique gateway identifier 102A; a unique patient identifier PTE, a unique device identifier 100E1, and a unique gateway identifier 102A; a unique patient identifier PTI, a unique device identifier 100I1, and a unique gateway identifier 102A; a unique patient identifier PTM, a unique device identifier 100M1, and a unique gateway identifier 102A; a unique patient identifier PTB, a unique device identifier 100B1, and a unique gateway identifier 102B; a unique patient identifier PTF, a unique device identifier 100F1, and a unique gateway identifier 102B; a unique patient identifier PTJ, a unique device identifier 100J1, and a unique gateway identifier 102B; a unique patient identifier PTN, a unique device identifier 100N1, and a unique gateway identifier 102B; a unique patient identifier PTC, a unique device identifier 100C1, and a unique gateway identifier 102C; a unique patient identifier PTG, a unique device identifier 100G1, and a unique gateway identifier 102C; a unique patient identifier PTK, a unique device identifier 100K1, and a unique gateway identifier 102C; a unique patient identifier PTO, a unique device identifier 100O1, and a unique gateway identifier 102C; a unique patient identifier PTD, a unique device identifier 100D1, and a unique gateway identifier 102D; a unique patient identifier PTH, a unique device identifier 100H1, and a unique gateway identifier 102D; a unique patient identifier PTL, a unique device identifier 100L1, and a unique gateway identifier 102D; and a unique patient identifier PTP, a unique device identifier 100P1, and a unique gateway identifier 102D.

The list at each gateway can be updated in response to the master list to allow a plurality of patient devices to communicate with each gateway, for example two three, and four our more devices per gateway. For example, each gateway may include a plurality of entries for unique patient device identifiers and unique device identifiers in response to the updated master list 106L. For example, gateway 102A comprises updated list 102AL comprising unique device identifier 100A1, 100E1, 100I1, and 100M1 for unique patient identifier PTA, PTE, PTI, and PTM, respectively. Gateway 102B comprises updated list 102BL comprising unique device identifier 100B1, 100F1, 100J1, and 100N1 for unique patient identifier PTB, PTF, PTJ, and PTN, respectively. Gateway 102C comprises updated list 102CL comprising unique device identifier 100C1, 100G1, 100K1, and 100O1 for unique patient identifier PTC, PTG, PTK, and PTO. Gateway 102D comprises updated list 102DL comprising unique device identifier 100D1, 100H1, 100L1, and 100P1 for unique patient identifier PTD, PTH, PTL, and PTP, respectively.

System 10 can be configured for mobile patients in many ways and may also be configured to accommodate many patients and/or beds per gateway. For example, each gateway on a first side of the ward can be configured to allow patients assigned to beds from the same side of the ward. Each of gateways 102A, 102B and 102C may each comprise the same list of adherent patient devices and/or patients, and each of gateways 102D, 102E and 102F, as described above, may each comprise the same list of adherent patient devices and/or patients. Each of list 102AL, 102BL and 103CL may each comprise unique patient identifiers PTA, PTE, PTI, PTM, PTB, PTF, PTJ, PTN, PTC, PTG, PTK, PTO corresponding to unique adherent device identifiers 100A1, 100E1, 100I1, 100M1, 100B1, 100F1, 100J1, 100N1, 100C1, 100G1, 100K1, 100O1, respectively. Gateways 102E and 102F may comprise lists similar to list 102D, so as to allow the patients to be located when roaming the ward. For example, the list of allowed devices of each of gateways 102D, 102E and 102F may comprise unique patient identifiers PTD, PTH, PTL and PTP corresponding to unique adherent device identifiers 100D1, 100H1, 100L1, 100P1.

FIG. 1A4-1 shows an updated master approved patient device list 106L and corresponding updated lists stored on the tangible medium of each gateway, in which each of the gateways is configured to communicate with the adherent devices of a plurality of patients and in which the gateways are configured to communicate with each other with a mesh network for the system as in FIGS. 1A to 1A4. Each of the adherent devices may pair directly with one or more of the gateways having the unique identifier stored on the gateway corresponding to the adherent device, for example with a Bluetooth protocol.

List 102AL of gateway 102A comprises unique patient device identifiers corresponding to patient PTA, patient PTE, patient PTI and patient PTM, such that gateway 102A can communicate with the devices adhered to patient PTA, patient PTE, patient PTI and patient PTM when patient PTA carries gateway 102A about the ward. List 102AL of gateway 102A comprises unique gateway identifiers corresponding to gateway 102B, gateway 102C and gateway 102D, such that gateway 102A can form a mesh network, for example with a ZigBee communication protocol, with gateway 102B, gateway 102C and gateway 102D, for example when one or more of the allowed gateways is unable to establish direct communication with the monitoring station.

List 102BL of gateway 102B comprises unique patient device identifiers corresponding to patient PTB, patient PTF, patient PTJ and patient PTN, such that gateway 102B can communicate with the devices adhered to patient PTB, patient PTF, patient PTJ and patient PTN when patient PTB carries gateway 102B about the ward. List 102BL of gateway 102B comprises unique gateway identifiers corresponding to gateway 102A, gateway 102C and gateway 102D, such that gateway 102B can form a mesh network, for example with a ZigBee communication protocol, with gateway 102A, gateway 102C and gateway 102D, for example when one or more of the allowed gateways is unable to establish direct communication with the monitoring station.

List 102CL of gateway 102C comprises unique patient device identifiers corresponding to patient PTC, patient PTG, patient PTK and patient PTO, such that gateway 102C can communicate with the devices adhered to patient PTC, patient PTG, patient PTK and patient PTO when patient PTC carries gateway 102C about the ward. List 102CL of gateway 102C comprises unique gateway identifiers corresponding to gateway 102A, gateway 102B and gateway 102D, such that gateway 102C can form a mesh network, for example with a ZigBee communication protocol, with gateway 102A, gateway 102B and gateway 102D, for example when one or more of the allowed gateways is unable to establish direct communication with the monitoring station.

List 102DL of gateway 102D comprises unique patient device identifiers corresponding to patient PTD, patient PTH, patient PTL and patient PTP, such that gateway 102D can communicate with the devices adhered to patient PTD, patient PTH, patient PTL and patient PTP when patient PTD carries gateway 102D about the ward. List 102DL of gateway 102D comprises unique gateway identifiers corresponding to gateway 102A, gateway 102B and gateway 102C, such that gateway 102D can form a mesh network, for example with a ZigBee communication protocol, with gateway 102A, gateway 102B and gateway 102C, for example when one or more of the allowed gateways is unable to establish direct communication with the monitoring station.

Figure 1B:
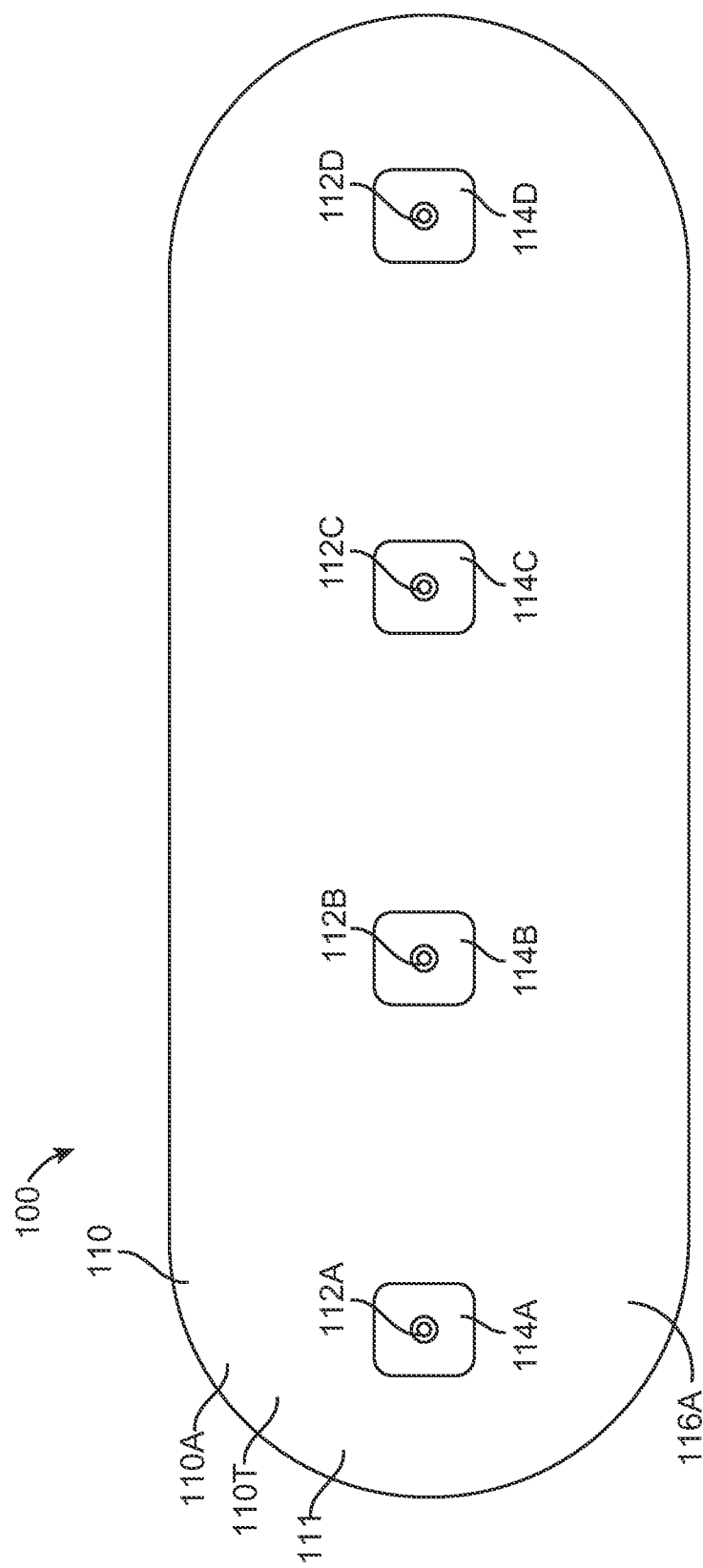
FIG. 1B shows a bottom view of the adherent device as in FIG. 1A comprising an adherent patch.

FIG. 1B shows a bottom view of adherent patient device 100 as in FIG. 1A comprising an adherent patch 110. Each of the adherent patient devices described above may be similar to adherent patch 100. Adherent patch 110 comprises a first side, or a lower side 110A, that is oriented toward the skin of the patient when placed on the patient. In many embodiments, adherent patch 110 comprises a tape 110T which is a material, preferably breathable, with an adhesive 116A. Patient side 110A comprises adhesive 116A to adhere the patch 110 and adherent patient device 100 to patient P. Electrodes 112A, 112B, 112C and 112D are affixed to adherent patch 110. In many embodiments, at least four electrodes are attached to the patch, for example six electrodes. In some embodiments, the patch comprises two electrodes, for example two electrodes to measure the electrocardiogram (ECG) of the patient. Gel 114A, gel 114B, gel 114C and gel 114D can each be positioned over electrodes 112A, 112B, 112C and 112D, respectively, to provide electrical conductivity between the electrodes and the skin of the patient. In many embodiments, the electrodes can be affixed to the patch 110, for example with known methods and structures such as rivets, adhesive, stitches, etc. In many embodiments, patch 110 comprises a breathable material to permit air and/or vapor to flow to and from the surface of the skin.

Figure 1C:
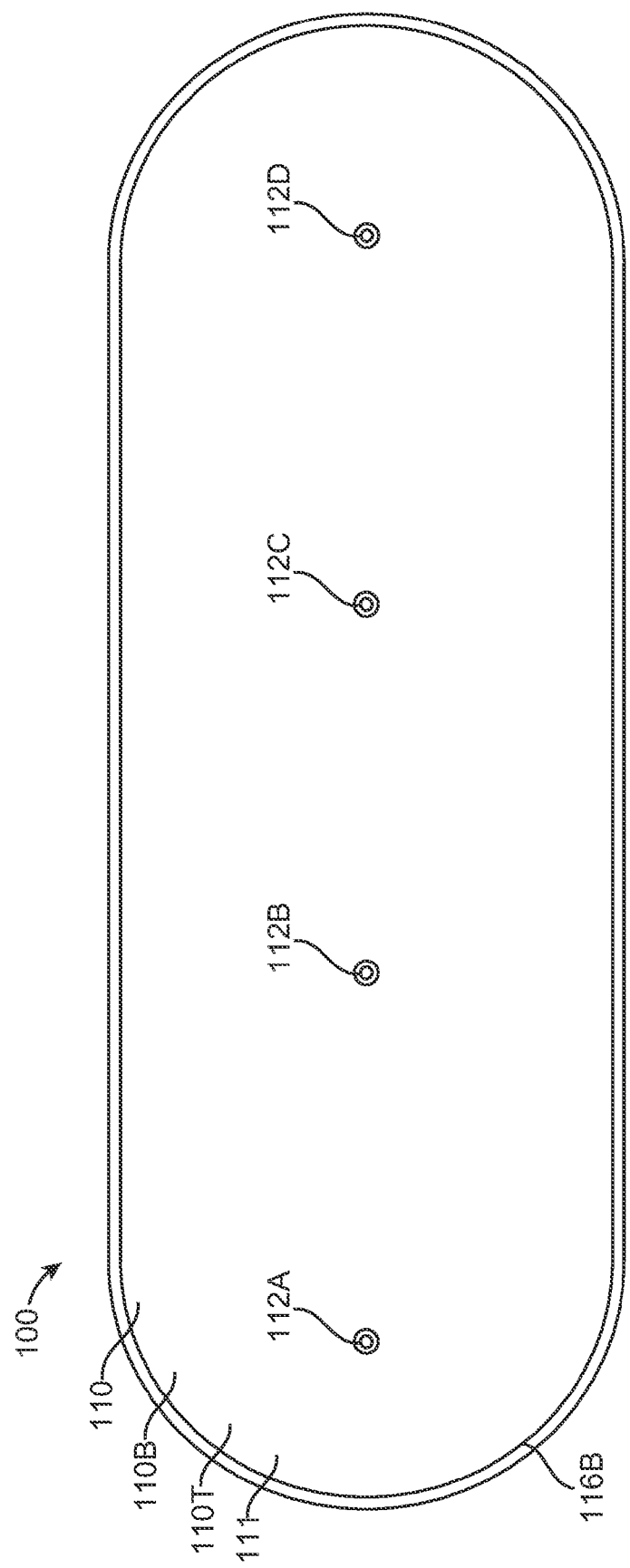
FIG. 1C shows a top view of the adherent patch, as in FIG. 1B.

FIG. 1C shows a top view of the adherent patch 100, as in FIG. 1B. Adherent patch 100 comprises a second side, or upper side 110B. In many embodiments, electrodes 112A, 112B, 112C and 112D extend from lower side 110A through adherent patch 110 to upper side 110B. An adhesive 116B can be applied to upper side 110B to adhere structures, for example a breathable cover, to the patch such that the patch can support the electronics and other structures when the patch is adhered to the patient. The PCB may comprise completely flex PCB, rigid PCB, rigid PCB combined flex PCB and/or rigid PCB boards connected by cable.

FIG. 1D shows a printed circuit boards and electronic components over adherent patch 110, as in FIG. 1A to 1C. In some embodiments, a printed circuit board (PCB), for example flex printed circuit board 120, may be connected to electrodes 112A, 112B, 112C and 112D with connectors 122A, 122B, 122C and 122D. Flex printed circuit board 120 can include traces 123A, 123B, 123C and 123D that extend to connectors 122A, 122B, 122C and 122D, respectively, on the flex PCB. Connectors 122A, 122B, 122C and 122D can be positioned on flex printed circuit board 120 in alignment with electrodes 112A, 112B, 112C and 112D so as to electrically couple the flex PCB with the electrodes. In some embodiments, connectors 122A, 122B, 122C and 122D may comprise insulated wires and/or a film with conductive ink that provide strain relief between the PCB and the electrodes. For example, connectors 122A, 122B, 122C and 122D may comprise a flexible polyester film coated with conductive silver ink. In some embodiments, additional PCB's, for example rigid PCB's 120A, 120B, 120C and 120D, can be connected to flex printed circuit board 120. Electronic components 130 can be connected to flex printed circuit board 120 and/or mounted thereon. In some embodiments, electronic components 130 can be mounted on the additional PCB's.

Electronic components 130 comprise components to take physiologic measurements, transmit data to remote center 106 and receive commands from remote center 106. In many embodiments, electronics components 130 may comprise known low power circuitry, for example complementary metal oxide semiconductor (CMOS) circuitry components. Electronics components 130 comprise an activity sensor and activity circuitry 134, impedance circuitry 136 and electrocardiogram circuitry, for example ECG circuitry 136. In some embodiments, electronics circuitry 130 may comprise a microphone and microphone circuitry 142 to detect an audio signal from within the patient, and the audio signal may comprise a heart sound and/or a respiratory sound, for example an S3 heart sound and a respiratory sound with rales and/or crackles.

Electronics circuitry 130 may comprise a temperature sensor and a heat flux sensor, for example a thermistor in contact with the skin of the patient and a heat flux sensor in contact with the skin of the patient, both of which are coupled to temperature circuitry 144 to measure a skin temperature and heat flux of the patient to determine a core temperature of the patient. The temperature circuitry may be used to determine the sleep and wake state of the patient. The temperature of the patient can decrease as the patient goes to sleep and increase when the patient wakes up.

Work in relation to embodiments of the present invention suggests that skin temperature may effect impedance and/or hydration measurements, and that skin temperature measurements may be used to correct impedance and/or hydration measurements. In some embodiments, increase in skin temperature or heat flux can be associated with increased vasodilation near the skin surface, such that measured impedance measurement decreased, even through the hydration of the patient in deeper tissues under the skin remains substantially unchanged. Thus, use of the temperature sensor can allow for correction of the hydration signals to more accurately assess the hydration, for example extra cellular hydration, of deeper tissues of the patient, for example deeper tissues in the thorax.

Electronics circuitry 130 may comprise a processor 146. Processor 146 comprises a tangible medium, for example read only memory (ROM), electrically erasable programmable read only memory (EEPROM) and/or random access memory (RAM). Processor 146 may comprise many known processors with real time clock and frequency generator circuitry, for example the PIC series of processors available from Microchip, of Chandler, Ariz. In some embodiments, processor 136 may comprise the frequency generator and real time clock. The processor can be configured to control a collection and transmission of data from the impedance circuitry electrocardiogram circuitry and the accelerometer. In many embodiments, device 100 comprise a distributed processor system, for example with multiple processors on device 100.

Electronics circuitry 130 may comprise additional circuitry 148 for measuring patient data. For example, circuitry 148 may comprise global positioning system (GPS) circuitry to measure location of the patient. Alternatively or in combination, circuitry 148 may comprise a pulsed oximeter sensor to measure oxygen in the blood of the patient. Circuitry 148 can be connected to processor to send the patient data to the processor and the wireless communication circuitry for transmission. For example circuitry 148 may comprise GPS circuitry to send patient location such that the patient can be located by hospital staff in response to the GPS circuitry signal sent from the adherent device to monitoring station.

In many embodiments, electronics components 130 comprise wireless communications circuitry 132 to communicate with remote center 106. The wireless communication circuitry can be coupled to the impedance circuitry, the electrocardiogram circuitry and the accelerometer to transmit to a remote center with a communication protocol at least one of the hydration signal, the electrocardiogram signal or the inclination signal. In specific embodiments, wireless communication circuitry is configured to transmit the hydration signal, the electrocardiogram signal and the inclination signal to the remote center with a single wireless hop, for example from wireless communication circuitry 132 to intermediate device 102. The communication protocol comprises at least one of Bluetooth, ZigBee, WiFi, WiMAX, IR, amplitude modulation or frequency modulation. In many embodiments, the communications protocol comprises a two way protocol such that the remote center is capable of issuing commands to control data collection.

Intermediate device 102 may comprise a data collection system to collect and store data from the wireless transmitter. The data collection system can be configured to communicate periodically with the remote center. The data collection system can transmit data in response to commands from remote center 106 and/or in response to commands from the adherent device.

Activity sensor and activity circuitry 134 can comprise many known activity sensors and circuitry. In many embodiments, the accelerometer comprises at least one of a piezoelectric accelerometer, capacitive accelerometer or electromechanical accelerometer. The accelerometer may comprises a 3-axis accelerometer to measure at least one of an inclination, a position, an orientation or acceleration of the patient in three dimensions. Work in relation to embodiments of the present invention suggests that three dimensional orientation of the patient and associated positions, for example sitting, standing, lying down, can be very useful when combined with data from other sensors, for example ECG data and/or bioimpedance data, for example a respiration rate of the patient.

Impedance circuitry 136 can generate both hydration data and respiration data. In many embodiments, impedance circuitry 136 is electrically connected to electrodes 112A, 112B, 112C and 112D in a four pole configuration, such that electrodes 112A and 112D comprise outer electrodes that are driven with a current and comprise force electrodes that force the current through the tissue. The current delivered between electrodes 112A and 112D generates a measurable voltage between electrodes 112B and 112C, such that electrodes 112B and 112C comprise inner, sense, electrodes that sense and/or measure the voltage in response to the current from the force electrodes. In some embodiments, electrodes 112B and 112C may comprise force electrodes and electrodes 112A and 112B may comprise sense electrodes. The voltage measured by the sense electrodes can be used to measure the impedance of the patient and determine the respiration rate and/or hydration of the patient.

In many embodiments, an adherent patient device comprises an emergency notification switch operable by the patient to trigger an emergency notification transmission from the adherent patient device. For example, the electronics circuitry 130 can comprise an emergency notification button 149 that can be pressed by the patient to trigger the transmission of an emergency notification by the wireless communication circuitry 132. While the emergency notification switch is shown as the emergency notification button 149, the emergency notification switch can take many forms, for example, a mechanical switch, an electrical switch, an optical switch, a proximity sensor, a push button, a capacitive sensor, or anything operable by the patient to generate a signal so as to trigger a transmission of an emergency notification from the adherent device. For example, the emergency notification switch can be coupled to the processor of the adherent device so as to generate an interrupt request (hereinafter "IRQ") signal to activate and/or wake up a micro-controller of the electronics circuitry 130 and so as to trigger the emergency notification transmission from the adherent patient device. The emergency notification switch can be conveniently configured and located on the adherent patient device so as to be easily operable by the patient without being susceptible to nuisance activations due to contact between the adherent patient device and another object, for example, a hospital bed. For example, the emergency button 149 can be located under a soft cover of the adherent patient device and can be configured to activate in response to a deliberate patient push on the button and not activate in response to more incidental contact. A transmitted emergency notification can be processed by the system to generate an appropriate alert, for example, similar to the generation of patient data based alerts described herein.

FIG. 1D1 shows an equivalent circuit 152 that can be used to determine optimal frequencies for measuring patient hydration. Work in relation to embodiments of the present invention indicates that the frequency of the current and/or voltage at the force electrodes can be selected so as to provide impedance signals related to the extracellular and/or intracellular hydration of the patient tissue. Equivalent circuit 152 comprises an intracellular resistance 156, or R(ICW) in series with a capacitor 154, and an extracellular resistance 158, or R(ECW). Extracellular resistance 158 is in parallel with intracellular resistance 156 and capacitor 154 related to capacitance of cell membranes. In many embodiments, impedances can be measured and provide useful information over a wide range of frequencies, for example from about 0.5 kHz to about 200 KHz. Work in relation to embodiments of the present invention suggests that extracellular resistance 158 can be significantly related extracellular fluid and to cardiac decompensation, and that extracellular resistance 158 and extracellular fluid can be effectively measured with frequencies in a range from about 0.5 kHz to about 20 kHz, for example from about 1 kHz to about 10 kHz. In some embodiments, a single frequency can be used to determine the extracellular resistance and/or fluid. As sample frequencies increase from about 10 kHz to about 20 kHz, capacitance related to cell membranes decrease the impedance, such that the intracellular fluid contributes to the impedance and/or hydration measurements. Thus, many embodiments of the present invention measure hydration with frequencies from about 0.5 kHz to about 20 kHz to determine patient hydration.

In many embodiments, impedance circuitry 136 can be configured to determine respiration of the patient. In specific embodiments, the impedance circuitry can measure the hydration at 25 Hz intervals, for example at 25 Hz intervals using impedance measurements with a frequency from about 0.5 kHz to about 20 kHz.

ECG circuitry 138 can generate electrocardiogram signals and data from two or more of electrodes 112A, 112B, 112C and 112D in many ways. In some embodiments, ECG circuitry 138 is connected to inner electrodes 112B and 122C, which may comprise sense electrodes of the impedance circuitry as described above. In some embodiments, ECG circuitry 138 can be connected to electrodes 112A and 112D so as to increase spacing of the electrodes. The inner electrodes may be positioned near the outer electrodes to increase the voltage of the ECG signal measured by ECG circuitry 138. In many embodiments, the ECG circuitry may measure the ECG signal from electrodes 112A and 112D when current is not passed through electrodes 112A and 112D, for example with switches as described in U.S. App. No. 60/972,527, the full disclosure of which has been previously incorporated herein by reference.

Figure 1E:
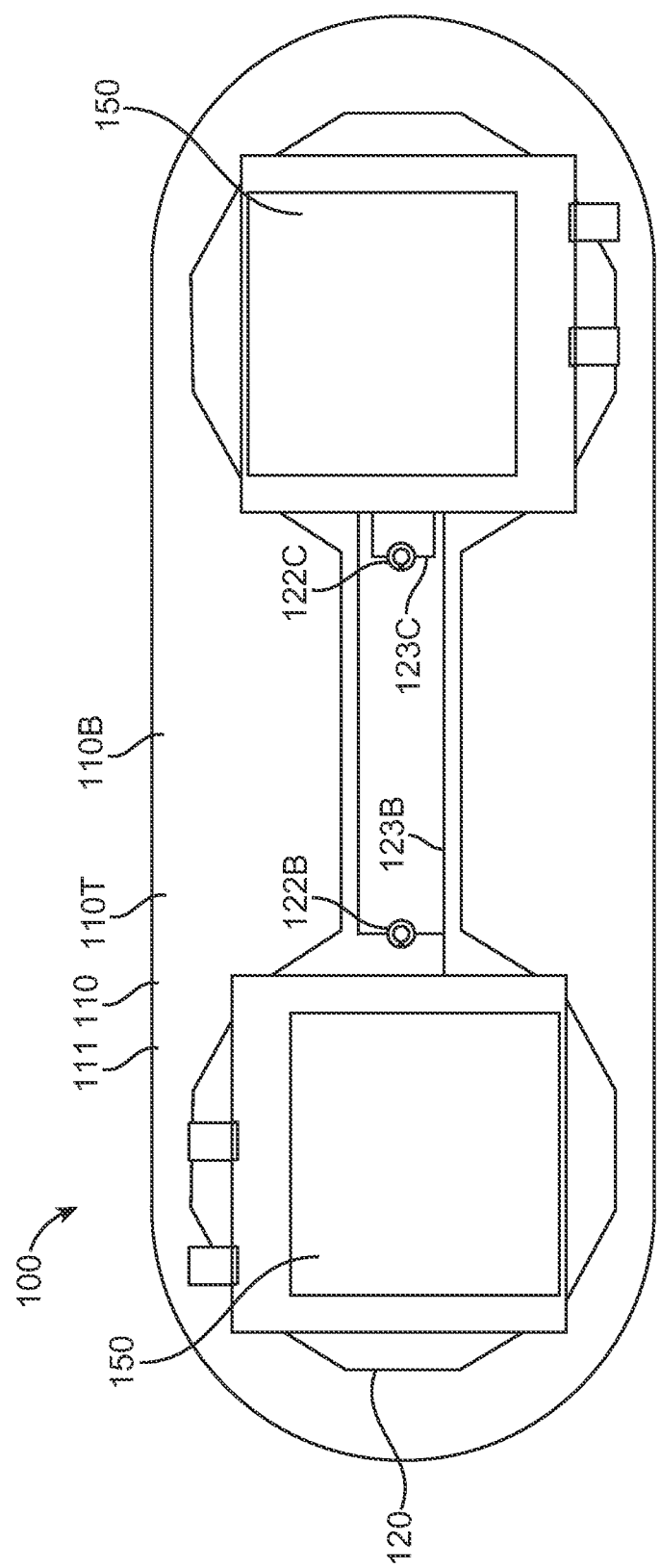
FIG. 1E shows batteries positioned over the printed circuit board and electronic components as in FIG. 1D.

FIG. 1E shows batteries 150 positioned over the flex printed circuit board and electronic components as in FIG. 1D. Batteries 150 may comprise rechargeable batteries that can be removed and/or recharged. In some embodiments, batteries 150 can be removed from the adherent patch and recharged and/or replaced.

Figure 1F:
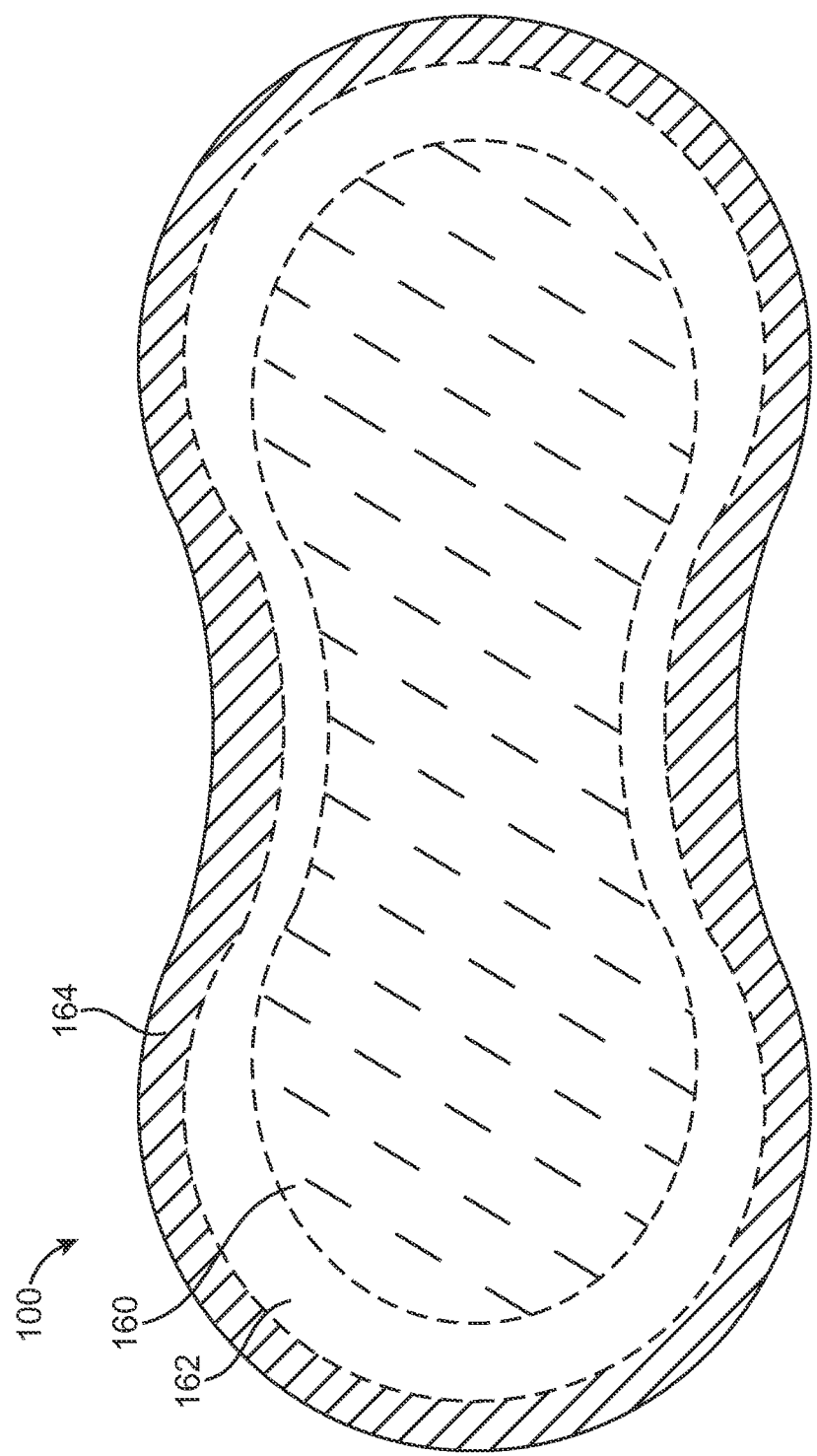
FIG. 1F shows a top view of an electronics housing and a breathable cover over the batteries, electronic components and printed circuit board as in FIG. 1E.

FIG. 1F shows a top view of a cover 162 over the batteries, electronic components and flex printed circuit board as in FIGS. 1A to 1E. In many embodiments, an electronics housing 160 may be disposed under cover 162 to protect the electronic components, and in some embodiments electronics housing 160 may comprise an encapsulant over the electronic components and PCB. In some embodiments, cover 162 can be adhered to adherent patch 110 with an adhesive 164 on an underside of cover 162. In many embodiments, electronics housing 160 may comprise a water proof material, for example a sealant adhesive such as epoxy or silicone coated over the electronics components and/or PCB. In some embodiments, electronics housing 160 may comprise metal and/or plastic. Metal or plastic may be potted with a material such as epoxy or silicone.

Cover 162 may comprise many known biocompatible cover, casing and/or housing materials, such as elastomers, for example silicone. The elastomer may be fenestrated to improve breathability. In some embodiments, cover 162 may comprise many known breathable materials, for example polyester, polyamide, and/or elastane (Spandex). The breathable fabric may be coated to make it water resistant, waterproof, and/or to aid in wicking moisture away from the patch.

Figure 1H:
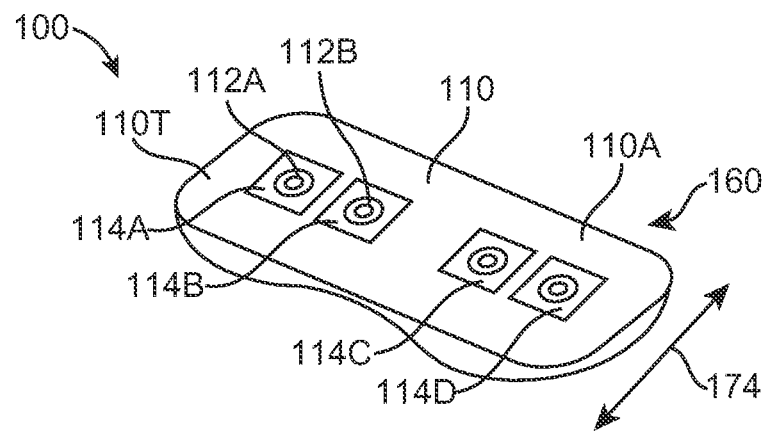
FIG. 1H shown a bottom isometric view of the adherent device as in FIGS. 1A to 1G.
Figure 1G:
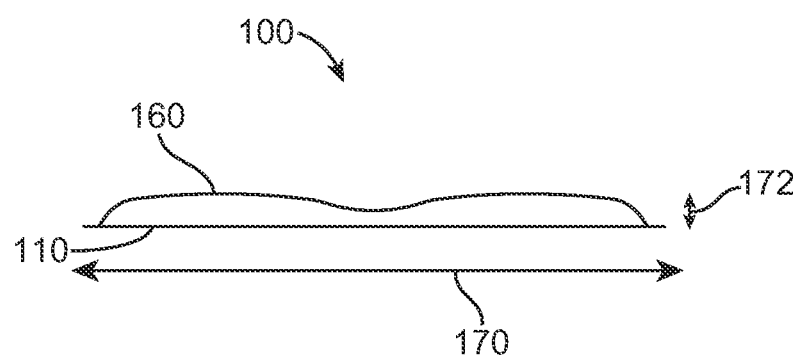
FIG. 1G shows a side view of the adherent device as in FIGS. 1A to 1F.

FIG. 1G shows a side view of adherent patient device 100 as in FIGS. 1A to 1F. Adherent patient device 100 comprises a maximum dimension, for example a length 170 from about 2 to 10 inches (from about 50 mm to about 250 mm), for example from about 4 to 6 inches (from about 100 mm to about 150 mm). In some embodiments, length 170 may be no more than about 6 inches (no more than about 150 mm). Adherent patient device 100 comprises a thickness 172. Thickness 172 may comprise a maximum thickness along a profile of the device. Thickness 172 can be from about 0.1 inches to about 0.4 inches (from about 5 mm to about 10 mm), for example about 0.3 inches (about 7.5 mm).

FIG. 1H shown a bottom isometric view of adherent patient device 100 as in FIGS. 1A to 1G. Adherent patient device 100 comprises a width 174, for example a maximum width along a width profile of adherent patient device 100. Width 174 can be from about 1 to about 4 inches (from about 25 mm to 100 mm), for example about 2 inches (about 50 mm).

Figure 1J:
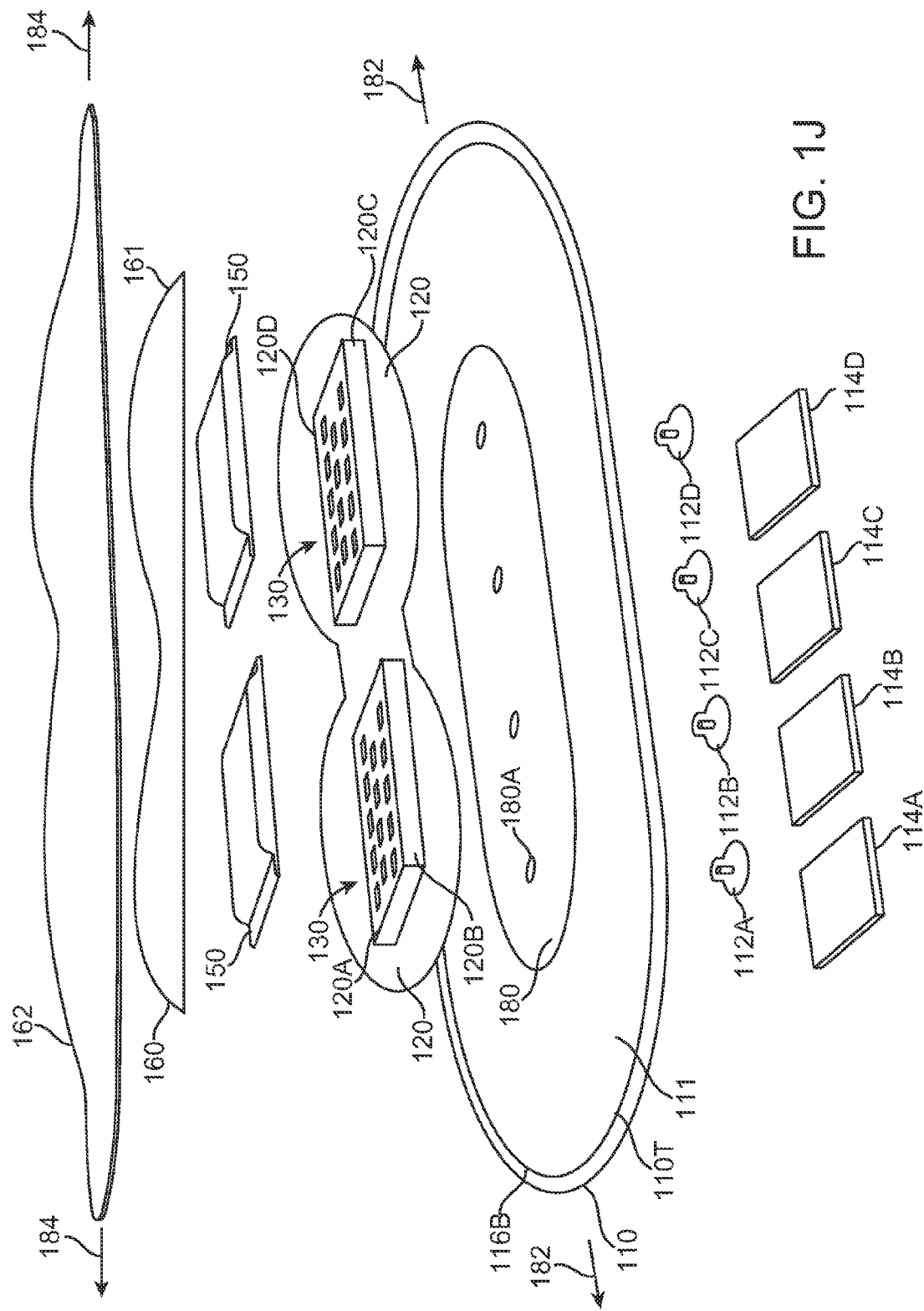

FIGS. 1I and 1J show a side cross-sectional view and an exploded view, respectively, of adherent patient device 100 as in FIGS. 1A to 1H. Device 100 comprises several layers. Gel 114A, or gel layer, is positioned on electrode 112A to provide electrical conductivity between the electrode and the skin. Electrode 112A may comprise an electrode layer. Adherent patch 110 may comprise a layer of breathable tape 110T, for example a known breathable tape, such as tricot-knit polyester fabric. An adhesive 116A, for example a layer of acrylate pressure sensitive adhesive, can be disposed on underside 110A of adherent patch 110.

A gel cover 180, or gel cover layer, for example a polyurethane non-woven tape, can be positioned over patch 110 comprising the breathable tape. A PCB layer, for example flex printed circuit board 120, or flex PCB layer, can be positioned over gel cover 180 with electronic components 130 connected and/or mounted to flex printed circuit board 120, for example mounted on flex PCB so as to comprise an electronics layer disposed on the flex PCB layer. In many embodiments, the adherent device may comprise a segmented inner component, for example the PCB may be segmented to provide at least some flexibility. In many embodiments, the electronics layer may be encapsulated in electronics housing 160 which may comprise a waterproof material, for example silicone or epoxy. In many embodiments, the electrodes are connected to the PCB with a flex connection, for example trace 123A of flex printed circuit board 120, so as to provide strain relive between the electrodes 112A, 112B, 112C and 112D and the PCB.

Gel cover 180 can inhibit flow of gel 114A and liquid. In many embodiments, gel cover 180 can inhibit gel 114A from seeping through breathable tape 110T to maintain gel integrity over time. Gel cover 180 can also keep external moisture, for example liquid water, from penetrating though the gel cover into gel 114A while allowing moisture vapor from the gel, for example moisture vapor from the skin, to transmit through the gel cover.

In many embodiments, cover 162 can encase the flex PCB and/or electronics and can be adhered to at least one of the electronics, the flex PCB or adherent patch 110, so as to protect at least the electronics components and the PCB. Cover 162 can attach to adherent patch 110 with adhesive 116B. Cover 162 can comprise many known biocompatible cover materials, for example silicone. Cover 162 can comprise an outer polymer cover to provide smooth contour without limiting flexibility. In many embodiments, cover 162 may comprise a breathable fabric. Cover 162 may comprise many known breathable fabrics, for example breathable fabrics as described above. In some embodiments, the breathable cover may comprise a breathable water resistant cover. In some embodiments, the breathable fabric may comprise polyester, nylon, polyamide, and/or elastane (Spandex) to allow the breathable fabric to stretch with body movement. In some embodiments, the breathable tape may contain and elute a pharmaceutical agent, such as an antibiotic, anti-inflammatory or antifungal agent, when the adherent device is placed on the patient.

The breathable cover 162 and adherent patch 110 comprise breathable tape can be configured to couple continuously for at least one week the at least one electrode to the skin so as to measure breathing of the patient. The breathable tape may comprise the stretchable breathable material with the adhesive and the breathable cover may comprises a stretchable water resistant material connected to the breathable tape, as described above, such that both the adherent patch and cover can stretch with the skin of the patient. Arrows 182 show stretching of adherent patch 110, and the stretching of adherent patch can be at least two dimensional along the surface of the skin of the patient. As noted above, connectors 122A, 122B, 122C and 122D between PCB 130 and electrodes 112A, 112B, 112C and 112D may comprise insulated wires that provide strain relief between the PCB and the electrodes, such that the electrodes can move with the adherent patch as the adherent patch comprising breathable tape stretches. Arrows 184 show stretching of cover 162, and the stretching of the cover can be at least two dimensional along the surface of the skin of the patient. Cover 162 can be attached to adherent patch 110 with adhesive 116B such that cover 162 stretches and/or retracts when adherent patch 110 stretches and/or retracts with the skin of the patient. For example, cover 162 and adherent patch 110 can stretch in two dimensions along length 170 and width 174 with the skin of the patient, and stretching along length 170 can increase spacing between electrodes. Stretching of the cover and adherent patch 110, for example in two dimensions, can extend the time the patch is adhered to the skin as the patch can move with the skin such that the patch remains adhered to the skin. Electronics housing 160 can be smooth and allow breathable cover 162 to slide over electronics housing 160, such that motion and/or stretching of cover 162 is slidably coupled with housing 160. The printed circuit board can be slidably coupled with adherent patch 110 that comprises breathable tape 110T, such that the breathable tape can stretch with the skin of the patient when the breathable tape is adhered to the skin of the patient, for example along two dimensions comprising length 170 and width 174. Electronics components 130 can be affixed to printed circuit board 120, for example with solder, and the electronics housing can be affixed over the PCB and electronics components, for example with dip coating, such that electronics components 130, printed circuit board 120 and electronics housing 160 are coupled together. Electronics components 130, printed circuit board 120, and electronics housing 160 are disposed between the stretchable breathable material of adherent patch 110 and the stretchable water resistant material of cover 160 so as to allow the adherent patch 110 and cover 160 to stretch together while electronics components 130, printed circuit board 120, and electronics housing 160 do not stretch substantially, if at all. This decoupling of electronics housing 160, printed circuit board 120 and electronic components 130 can allow the adherent patch 110 comprising breathable tape to move with the skin of the patient, such that the adherent patch can remain adhered to the skin for an extended time of at least one week, for example two or more weeks.

An air gap 169 may extend from adherent patch 110 to the electronics module and/or PCB, so as to provide patient comfort. Air gap 169 allows adherent patch 110 and breathable tape 110T to remain supple and move, for example bend, with the skin of the patient with minimal flexing and/or bending of printed circuit board 120 and electronic components 130, as indicated by arrows 186. Printed circuit board 120 and electronics components 130 that are separated from the breathable tape 110T with air gap 169 can allow the skin to release moisture as water vapor through the breathable tape, gel cover, and breathable cover. This release of moisture from the skin through the air gap can minimize, and even avoid, excess moisture, for example when the patient sweats and/or showers.

The breathable tape of adherent patch 110 may comprise a first mesh with a first porosity and gel cover 180 may comprise a breathable tape with a second porosity, in which the second porosity is less than the first porosity to minimize, and even inhibit, flow of the gel through the breathable tape. The gel cover may comprise a polyurethane film with the second porosity.

In many embodiments, the adherent device comprises a patch component and at least one electronics module. The patch component may comprise adherent patch 110 comprising the breathable tape with adhesive coating 116A, at least one electrode, for example electrode 114A and gel 114. The at least one electronics module can be separable from the patch component. In many embodiments, the at least one electronics module comprises the flex printed circuit board 120, electronic components 130, electronics housing 160 and cover 162, such that the flex printed circuit board, electronic components, electronics housing and cover are reusable and/or removable for recharging and data transfer, for example as described above. In many embodiments, adhesive 116B is coated on upper side 110A of adherent patch 110B, such that the electronics module can be adhered to and/or separated from the adhesive component. In specific embodiments, the electronic module can be adhered to the patch component with a releasable connection, for example with Velcro™, a known hook and loop connection, and/or snap directly to the electrodes. Two electronics modules can be provided, such that one electronics module can be worn by the patient while the other is charged, as described above. Monitoring with multiple adherent patches for an extended period is described in U.S. Pat. App. No. 60/972,537, the full disclosure of which has been previously incorporated herein by reference. Many patch components can be provided for monitoring over the extended period. For example, about 12 patches can be used to monitor the patient for at least 90 days with at least one electronics module, for example with two reusable electronics modules.

At least one electrode 112A can extend through at least one aperture 180A in the breathable tape 110 and gel cover 180.

In some embodiments, the adhesive patch may comprise a medicated patch that releases a medicament, such as antibiotic, beta-blocker, ACE inhibitor, diuretic, or steroid to reduce skin irritation. The adhesive patch may comprise a thin, flexible, breathable patch with a polymer grid for stiffening. This grid may be anisotropic, may use electronic components to act as a stiffener, may use electronics-enhanced adhesive elution, and may use an alternating elution of adhesive and steroid.

Second adherent patient device 100J and third adherent patient device 100A may comprise components similar to adherent patient device 100, described above. The processor of adherent patient device 100, described above may comprise a system controller to control communication and/or actions of first adherent patient device 100J and second device 100A, for example data collection and transmission. In many embodiments, data collected from second adherent patient device 100J and third adherent patient device 100A is sent wirelessly to device 100, which device 100 transmits the data to the intermediate device. In some embodiments, adherent patient device 100, second adherent patient device 100J and third adherent patient device 100A can each communicate data wirelessly with the intermediate device and may each receive instructions from the intermediate device.

FIG. 1K shows at least one electrode 190 configured to electrically couple to a skin of the patient through a breathable tape 192. In many embodiments, at least one electrode 190 and breathable tape 192 comprise electrodes and materials similar to those described above. Electrode 190 and breathable tape 192 can be incorporated into adherent devices as described above, so as to provide electrical coupling between the skin an electrode through the breathable tape, for example with the gel.

Figure 1L:
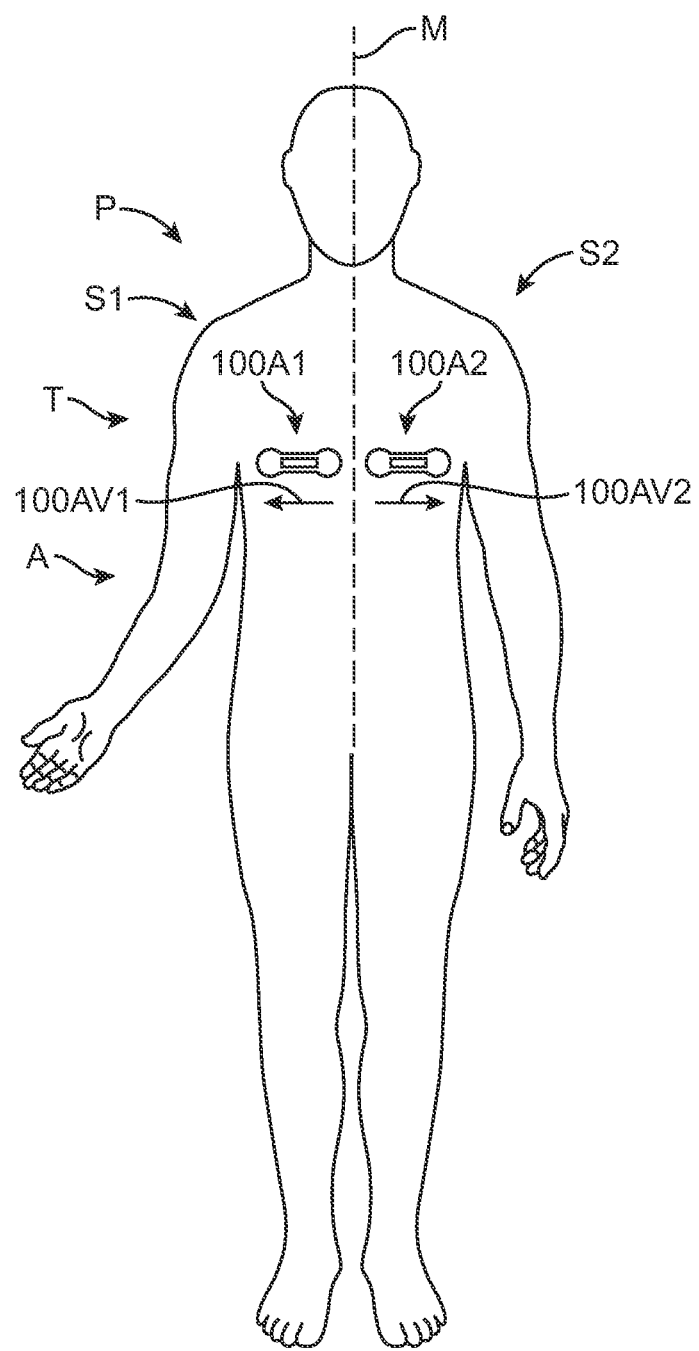
FIG. 1L shows a plurality of adherent patient devices simultaneously adhered to the patient, in accordance with embodiments of the present invention.

FIG. 1L shows a plurality of adherent patch devices simultaneously adhered to the patient. The plurality of adherent patient devices simultaneously adhered to the patient may comprise a first adherent patient device similar to adherent device 100 described above, for example adherent patient device 100A1 and a second adherent patient device similar to adherent device 100, for example adherent device 100A2. The first adherent device 100A1 and the second adherent device 100A2 are shown adhered to first side S1 and second side S2, respectively, of patient P, such that first adherent device 100A1 is adhered opposite to second adherent device 100A2 across midline M of patient P, with each adherent device placed on opposing sides of the patient. Adherent device 100A1 measures a first vector 100A1V, for example an electrocardiogram vector with at least two electrodes of adherent device 100A1. Adherent device 100A2 measures a second vector 100A2V, for example an electrocardiogram vector with at least two electrodes of adherent device 100A2.

The adherent devices can transmit the first vector and the second vector to the gateway in many ways. For example each of the simultaneously adhered adherent devices can transmit the vector data with direct pairing of each adherent device to one or more of the gateways, as described above. The adherent devices may also pair among them selves. For example adherent device 100A2 can pair with adherent device 100A1 to transmit vector 100A2V to adherent device 100A1, and adherent device 100A1 can pair with one or more of the gateways, as described above, to transmit vector 100A1 and vector 100A2.

FIG. 2 shows a method 200 of monitoring patient. A step 205 admits the patient to the hospital, for example to the general ward of the hospital. A step 210 assigns a unique patient identifier to the patient, for example a unique hexadecimal serial number. A step 215 assigns an adherent device with a unique adherent device identifier to the patient. The unique adherent device identifier may comprise a serial number, for example a hexadecimal serial number. The assigned adherent device may also comprise an emergency notification switch (as described above) that can be operated by the patient to trigger an emergency notification transmission from the adherent device. A step 220 associates the unique device identifier with the patient, for example with the unique patient identifier, such that the unique device identifier corresponds to at least one of the patient or the unique patient identifier. A step 225 adheres the adherent patient device with the unique adherent device identifier to the patient. Additional adherent devices can be adhered to the patient. A step 230 pairs the adherent local device with the local processor system, for example with a hand held device of the local processor system, and transmits the unique adherent device identifier to the local processor system. A step 235 assigns at least one of the patient or the adherent device to a bed of the hospital, for example assigns both. The patient can be assigned to the bed based on the unique patient identifier, and the adherent device can be assigned to the bed based on the unique adherent device identifier. A step 240 assigns at least one of the patient or the adherent device to one or more of the gateways, and this assignment can be based on the unique device identifier and the unique gateway identifier. For example, both the adherent device and the patient can be assigned to each of the gateways on one side of the ward, as described above, so as to transmit patient data and determine the location of the patient when the patient wanders about the ward. A step 245 updates a list of approved patient devices and patients so as to include the adherent device adhered to the patient and the patient. The list may also include the gateways assigned to the adherent device. A step 250 transmits the list of approved patient devices and patients to the gateways. The list can be transmitted to the gateways in many ways. For example the list can be subdivided into portions and the relevant portion of the list for each gateway can be transmitted to the corresponding gateway. This use of lists can regulate the pairing of gateways and improve throughput, as explained below.

A step 255 customizes the alerts. The alerts can be customized in many ways so as to suit the health condition and personal circumstances of each individual patient. The alerts can also be customized to provide an appropriate alert for each individual patient corresponding to a patient-initiated emergency notification transmission from the patient's adherent device. A sub-step 255A can determine the alert targets. The alert targets can comprise many appropriate targets, for example the treating physician present in the hospital, an attending specialist who is present at the hospital, a resident physician specialist who is present at the hospital, a referring physician located outside the hospital, a primary care physician located outside the hospital, nurses at the monitoring station, ICU personnel, and a family member. A step 255 determines the contact information for the alerts, for example at least one of a pager number, an email address or a phone number. The contact information may already be loaded into a hospital directory. The contact information and targets can be automatically updated based on the time and date and known schedule of hospital personnel, for example the pager number of the attending cardiologist can be automatically updated when the rotation changes and a new attending cardiologist checks in with the hospital, such that the alerts are automatically directed to the new cardiologist when the rotation changes.

A step 255C determines the alert triggers. The alert triggers can be customized based on the patient condition, and the alert target can be determine in response to the patient condition that triggers the alert. The special condition of the patient may comprise at least one of a cardiac condition, a kidney condition or a fetal condition, and the attending specialist may comprise at least one of an attending cardiologist, an attending nephrologist or an attending obstetrician, respectively. For example, with a patient admitted with a heart problem, such as tachycardia, the alerts triggers can be customized to detect heart trouble, such as from the EEG signal and to notify the attending cardiologist. For a patient admitted with kidney trouble, the alert trigger can be set to an attending nephrologist in response to patient hydration. The alert triggers can also be customized based on physician input, for example a threshold can be adjusted by the physician such that the attending physician or a resident can be notified when the threshold is crossed.

The alert triggers determined in step 255C may comprise alert triggers determined in response to patient data measured from sensors of the adherent device. For example, the adherent device may comprise a three axis accelerometer, as described above, and the alert can be triggered in response to a fall of the patient. The adherent device may comprise impedance circuitry to measure respiration, as described above, and the alert may be triggered in response to respiratory distress of the patient. The adherent device may comprise a pulsed oximeter to measure patient blood oxygen amounts, for example saturation, and the alert may be triggered in response to oxygen distress of the patient.

The alert triggers determined in step 255C may comprise alert triggers determined in response to a patient-initiated emergency notification transmitted from the adherent device. For example, a patient-initiated emergency notification can trigger an alert that notifies health-care professional to check in on the patient. Alert triggers can also be determined in response to both a patient-initiated emergency notification transmission and patient data measured by the adherent patient device so that an alert of appropriate urgency can be generated when a patient-initiated emergency notification is accompanied by patient data indicative of a serious patient condition.

The patient can be sent into the general ward and data collected. A step 260 sends the patient into the general ward of the hospital. The patient can be free to move about the hospital. A step 265 measures patient data, for example when the device is adhered to the patient. The measured patient data may comprise many kinds of patient, for example as described above. A step 270 transmits the measured patient data and/or any patient-initiated emergency notification from the adherent device to the gateway. The data and/or patient-initiated emergency notification can be transmitted with the unique device identifier, such that the patient from whom the data were measured and/or from whom the notification was received can be determined when the data and/or notification arrives at the front end server and the back end server. A step 275 transmits the patient data and/or notification from the gateway to the front end server. The data and/or notification can be transmitted from the gateway to the front end server with the unique gateway identifier. The front end server may comprise at least one display of the monitoring station, as for example the nurses' monitoring station as described above. A step 280 processes time critical data and/or notification. The front end server can be configured to detect an immediate life threatening condition of the patient. As examples, the immediate life threatening condition may comprise at least one of an immediate life threatening heart condition or an immediate life threatening fetal condition. For example, patient vital signs can be processed to determine when the patient requires resuscitation. A step 285 determines the patient location in response to the unique patient identifier and the unique gateway identifier. A step 290 issues an alert from the front end server with the patient location in response to the time critical patient data and/or notification. For example, an alert can be sent to the attending cardiologist in response to patient tachycardia.

A step 292 transmits the patient data and/or notification from the front end server to the back end server. The patient data and/or notification sent to the back end server may comprise critical patient data and/or notification that is not time critical, for example data that changes slowly with time such as patient hydration data. The back end server can be configured to detect a non-immediate life threatening condition, for example a slight increase in hydration of the patient that is not life threatening. The patient data sent to the back end server may also comprise time critical patient data sent to the back end server for processing with the non-time critical data. A step 294 processes the patient data and/or notification at the back end server. A step 296 issues an alert from the back end server in response to the patient data and/or notification. For example, a change in patient hydration status can be sent to an attending nephrologist for a patient who is treated with dialysis. The alert from the back end server may comprise an alert indicating that that patient is at risk for an impending cardiac decompensation, for example when patient hydration increases.

Method 200 can be used during the admission of additional patients to the hospital, and the above steps can be repeated as additional patients are admitted to the hospital.

It should be appreciated that the specific steps illustrated in FIG. 2 provide a particular method of monitoring a patient, according to some embodiments of the present invention. Other sequences of steps may also be performed according to alternative embodiments. For example, alternative embodiments of the present invention may perform the steps outlined above in a different order. Moreover, the individual steps illustrated in FIG. 2 may include multiple sub-steps that may be performed in various sequences as appropriate to the individual step. Furthermore, additional steps may be added or removed depending on the particular applications. One of ordinary skill in the art would recognize many variations, modifications, and alternatives.

FIG. 3 shows a method 300 of monitoring at least one patient, for example a plurality of patients. Method 300 can be performed with the monitoring system described above, and method 300 can fully incorporate the entirety of method 200, as described above, and with a plurality of patients admitted to the hospital in accordance with method 200. A step 305 adheres a monitoring device to a patient. Each of the patient worn devices may be similar to adherent patient device 100 as described above. A step 310 measures patient data, for example, the parameters described above. The patient worn device performs a step 315 to transmit a unique identifier, such as a serial number, to an intermediate device, for example, a gateway or intermediate device 102 as described above. The identifier may be transmitted via, for example, a wireless connection, a cellular connection, a ZigBee connection, a BlueTooth connection, an Internet connection, an intranet connection, a wire connection, a cable connection or the like. The patient worn device performs a step 320 to request pairing with the gateway or intermediate device. Often, the gateway or intermediate device may include a list and/or range of allowed devices, patients, and/or device serial numbers, for instance an approved patient list, as previously described. The gateway or intermediate device performs a step 325 to receive the approved patient list. The gateway or intermediate device performs a logic step 330 in which a sub-step 335 determines whether the identifier is in the approved patient list and/or within the range of allowed devices. If the identifier is not in the approved patient list or within the range of allowed devices, the gateway or intermediate device performs step 340 which excludes communication between the patient worn device with the identifier in question and the gateway. If the identifier is in the approved patient list or within the range of allowed devices, the gateway or intermediate device performs step 345 which allows pairing or paired communication between the gateway and the patient worn device. If pairing is allowed, patient worn device performs a step 350 to exchange a link key between the patient worn device and the gateway or intermediate device. A step 344 pairs the patient device with the gateway. The exchanged link key allows the patient worn device to pair with the gateway in step 355. The patient worn device performs a step 360 to encrypt the patient data. The patient worn device performs a step 365 to transmit the encrypted patient data to the gateway or intermediate device. The gateway or intermediate device receives the encrypted patient data in a step 370 and decrypts the encrypted patient data in a step 375. The exchanged link key may enable the gateway or intermediate device to decrypt the patient data. The gateway or intermediate device performs a step 380 which transmit the patient data to a server at the monitoring station and may transmit the patient data to a backend server or system at a remote center and/or site as previously described. The patient data may also be decrypted by server or the backend server or system and transmitted as encrypted data from the patient worn device to the gateway or intermediate device to server or the backend server or system. The approved patient list may be updated by the backend system or server with a step 385. Once the approved device list or range of allowed device serial number has been updated, the backend system or server performs a step 390 to send the updated approved patient or device list or range of allowed devices to a gateway or intermediate device. Gateway or intermediate device may then repeat logic step 330.

It should be appreciated that the specific steps illustrated in FIG. 3 provide a particular method of monitoring a patient, according to an embodiment of the present invention. Other sequences of steps may also be performed according to alternative embodiments. For example, alternative embodiments of the present invention may perform the steps outlined above in a different order. Moreover, the individual steps illustrated in FIG. 3 may include multiple sub-steps that may be performed in various sequences as appropriate to the individual step. Furthermore, additional steps may be added or removed depending on the particular applications. One of ordinary skill in the art would recognize many variations, modifications, and alternatives.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A system to monitor a plurality of patients, the system comprising:
    a plurality of adherent patient devices, each adherent patient device comprising a unique patient device identifier, an adhesive and wireless communication circuitry, said each device configured to adhere to a skin of one of the plurality of patients to measure patient data and support the wireless communication circuitry, the wireless communication circuitry configured to transmit the patient data;
    a local processor system comprising a tangible medium and at least one display disposed at a monitoring station, the local processor system configured to receive the patient data and display the patient data to a user at the monitoring station; and
    a plurality of gateways configured to receive the patient data from the wireless communication circuitry and transmit the patient data to the local processor system, wherein each gateway is positioned at a unique location and wherein each gateway of the plurality of gateways comprises a unique gateway identifier and wherein each gateway of the plurality of gateways is configured to transmit the unique gateway identifier, the unique patient device identifier and the patient data to the local processor system and wherein the local processor system is configured to determine the location of each patient in response to the unique gateway identifier and the unique patient device identifier.

2. The system of claim 1 wherein the monitoring station comprises a nurses' station, the user comprises a plurality of nurses and the at least one display comprises a central terminal disposed at the nurses' station to display the patient data to the plurality of nurses and wherein the at least one display is configured to display a status of each of the plurality of patients.

3. The system of claim 1 wherein each adherent patient device comprises a unique device identifier and wherein the local processor system is configured to customize an alert for each adherent device of the plurality based on the unique device identifier.

4. The system of claim 3 wherein each patient has a unique patient identifier and wherein the local processor system is configured to associate the unique device identifier with at least one of the unique patient identifier, a name of the patient, an assigned room of the patient or an assigned bed of the patient.

5. The system of claim 4 wherein the local processor system is configured to associate the unique device identifier with the unique patient identifier and send the customized alter to the physician in response to the unique device identifier.

6. The system of claim 3 wherein the local processor system comprises at least one handheld mobile device configured to customize the alert.

7. The system of claim 3 wherein the local processor system is configured to customize the alerts with at least one of a physician to notify, a family member to notify or a health care provider to notify.

8. The system of claim 3 wherein the local processor system is configured to customize the alerts in response to a condition of the patient and to select a specialized physician to notify in response to a special condition of the patient, the specialized physician comprising at least one of a cardiologist, a nephrologist or an obstetrician and wherein the specialized condition comprises at least one of a heart condition, a kidney condition or a fetal condition.

9. The system of claim 1 further comprising a plurality of alert devices comprising at least one of a light, a beeper, a buzzer and wherein each of the plurality of alert devices is located on one or more of the adherent patient device, the gateway, the monitoring station or an alarm device coupled to the gateway.

10. The system of claim 9 wherein the alert device comprises the alarm device coupled to the gateway and wherein the local processor system is configured to activate each alarm device in response to a unique gateway identifier and a unique adherent device identifier.

11. The system of claim 9 wherein each alert device comprises a switch to deactivate the alert device.

12. The system of claim 1 wherein the local processor system comprises a front end server connected to the plurality of gateways, the front end server configured to receive the patient data from the plurality of gateways and show the patient data on the at least one display.

13. The system of claim 1 further comprising a remote processor system having a back end server located remote from the front end server, the back end server configured to receive at least a portion of the patient data from the front end server.

14. The system of claim 13 wherein the local processor system is configured to detect an immediate life threatening condition of the patient and issue an alert in response to the patient data and wherein the remote processor system is configured to detect a non-immediate life threatening condition of the patient and issue an alert in response to the patient data.

15. The system of claim 14 wherein the immediate life threatening condition comprises at least one of an immediate life threatening heart condition or an immediate life threatening fetal condition and wherein the non-immediate life threatening condition comprises at least one of a non-life threatening heart condition, a non-life threatening kidney condition or a non-life threatening fetal condition.

16. The system of claim 15 wherein the life immediate threatening condition comprises the immediate life threatening heart condition and the immediate life threatening heart condition comprises at least one of a ventricular tachycardia or a ventricular fibrillation and wherein the non-life threatening condition comprises the non-life threatening heart condition and the non-life threatening heart condition comprises at least one of a non-sustained ventricular tachycardia or an atrial fibrillation.

17. The system of claim 1 wherein each adherent patient device comprises an adherent device processor comprising a tangible medium configured to process the patient data, each gateway comprises a gateway processor comprising a tangible medium configured to process patient data and wherein the local processor system is configured to process patient data transmitted from the plurality of gateway devices and transmit processed patient data to a remote processor system.

18. The system of claim 1 wherein each adherent patient device comprises a unique patient device identifier and wherein the local processor system is configured to store a list with the unique patient device identifier for each adherent patient device adhered to the patient, and wherein each gateway of the plurality of gateways is configured to communicate with at least one of the plurality of patient devices in response to the list.

19. The system of claim 18 wherein each gateway is configured to transmit patient data and the unique patient device identifier in response to the list.

20. The system of claim 18 wherein local processor system is configured to receive the patient data and determine locations of the plurality of patients when at least some of the patients are mobile.

21. The system of claim 18 wherein the local processor system is configured to change the list to an updated list and transmit at least a portion of the updated list to at least a portion of the plurality of gateways when one of the plurality of adherent devices is at least one of adhered to or removed from one of the patients.

22. The system of claim 20 wherein a first portion of the plurality of gateways is configured to communicate with a first portion of the plurality of adherent patient devices adhered to a first portion of the plurality of patients and wherein a second portion of the plurality of gateways is configured to communicate with a second portion of the plurality of adherent patient devices adhered to a second portion of the plurality of patients.

23. The system of claim 22 wherein the first portion of the plurality of gateways cover a first area and wherein the second portion of the plurality of gateways cover a second area, the first area overlapping substantially with the second area, such that the first portion of adherent devices transmit patient data through the first portion of the plurality of gateways when the first portion of the plurality of patients roam through the second area and wherein the second portion of adherent devices transmit patient data through the second portion of the plurality of gateways when the second portion of the plurality of patients roam through the first area.

24. The system of claim 22 wherein the first portion of the plurality of gateways comprises a first unique gateway device list comprising the unique identifiers of the first portion of patient devices and wherein the second portion of the plurality of gateways comprises a second unique gateway device list comprising the unique identifiers of the second portion of patient devices.

25. The system of claim 24 wherein the first portion of the plurality of gateways comprises at least about five gateways and the first portion of the plurality of adherent patient devices comprises at least about ten adherent patient devices and wherein the second portion of the plurality of gateways comprises at least about five gateways and the second portion of the plurality of adherent patient devices comprises at least about ten adherent patient devices.

26. The system of claim 1 wherein the adherent patient device comprises a plurality of adherent patient devices configured to adhere simultaneously to the patient on opposite sides of a chest of the patient to enhance fidelity of data signal measured from the patient.

27. The system of claim 1 wherein the plurality of adherent patient devices comprises a first adherent device comprising first wireless communication circuitry and a second adherent device comprising second wireless communication circuitry, the first adherent device comprising a first at least two electrodes to measure a first cardiac vector on a first side of the chest and the second adherent device comprises a second adherent device comprising a second at least two electrodes to measure a second cardiac vector, and wherein the first wireless communication circuitry is configured to transmit the first cardiac vector and the second wireless communication circuitry is configured to transmit the second cardiac vector.

28. The system of claim 1 wherein the adherent patient device comprises a GPS receiver to locate the adherent patient device adhered to the patient.

29. The system of claim 1 wherein at least one of the adherent patient device, the gateway or the monitoring station comprise a battery indicator to indicate battery power.

30. The system of claim 1 wherein the plurality of gateways comprises a hospital-wide gateway network configured to monitor the plurality of patients when at least some the patients are ambulatory and roam the hospital.

31. The system of claim 1 wherein each gateway of the plurality of gateways comprises first wireless communication circuitry configured to communicate with one or more of the plurality of adherent patch devices and second wireless communication circuitry configured to communicate with a transceiver of the local processor system.

32. The system of claim 31 wherein each gateway of the plurality of gateways is configured to be carried by a patient of the plurality of patients.

33. The system of claim 32 wherein each gateway of the plurality of gateways is configured to communicate directly with the transceiver of the local processor system.

34. The system of claim 33 wherein each gateway of the plurality of gateways is configured to communicate with a cellular connection to the transceiver of the local processor system.

35. The system of claim 32 wherein each gateway of the plurality of gateways is configured to communicate with at least one other gateway of the plurality of gateways with a mesh wireless communication protocol.

36. The system of claim 35 wherein the mesh wireless communication protocol comprises ZigBee.

37. The system of claim 35 wherein each gateway of the plurality of gateways comprises a unique gateway device identifier.

38. The system of claim 37 wherein each gateway of the plurality is configured to communicate with at least one other gateway in response to the unique gateway device identifier of the at least one other gateway.

39. The system of claim 38 wherein each gateway of the plurality comprises a list of unique gateway device identifiers and wherein each gateway is configured to communicate with the at least one other gateway in response to the list.

40. The system of claim 39 wherein the list at each gateway comprises at least one unique gateway identifier and at least one of a unique patient identifier or a unique device identifier, and wherein each gateway is configured to communicate with the at least one other gateway in response to the at least one unique gateway identifier and to communicate with one or more of the plurality of adherent devices in response to the at least one of the unique patient identifier or the unique adherent device identifier.

41. The system of claim 39 wherein each gateway of the plurality is configured to transmit the unique gateway device identifier with the patient data to determine which gateways transmit the patient data for each patient to the local processor system.

42. The system of claim 41 wherein each gateway of the plurality is configured to transmit the unique gateway device identifier with the patient data to determine a path of the patient data.

43. The system of claim 1 wherein each adherent patient device comprises, impedance circuitry configured to measure patient impedance data to determine at least one of patient hydration or patient respiration, electrocardiogram circuitry configured to measure an electrocardiogram data of the patient, accelerometer circuitry to measure acceleration data of the patient, oximeter circuitry to measure blood oxygen data of the patient, and at least one of a temperature sensor or a heat flux sensor configured to measure temperature data of the patient, wherein the wireless communication circuitry is configured to transmit the impedance data, the electrocardiogram data, the accelerometer data or the temperature data to at least one gateway of the plurality of gateways.

44. The system of claim 1 at least one of the local processor system or the processor of the adherent patch device is configured to trigger an alert in response to at least one of a patient fall, a patient respiratory distress or a patient oxygen distress.

45. The system of claim 1, wherein each adherent patient device comprises an emergency switch operable by the patient to trigger an emergency notification transmission.

46. The system of claim 45, wherein: each adherent patient device comprises a unique device identifier; the patient-initiated emergency notification transmission comprises the unique device identifier; and the local processor system is configured to receive the patient-initiated emergency notification transmission and identify the originating adherent patient device in response to the received emergency notification.

47. The system of claim 46, wherein: each patient has a unique patient identifier; and the local processor system is configured to associate the unique device identifier of the received emergency notification with at least one of the unique patient identifier, a name of the patient, an assigned room of the patient, or an assigned bed of the patient.

48. A method of monitoring a plurality of patients, the method comprising:
adhering at least one adherent patient device comprising wireless communication circuitry to a skin of at least one patient of the plurality of patients to measure patient data, such that the wireless communication circuitry is supported with the skin of the patient, wherein the at least one adherent patient device comprises a plurality of adherent patient devices in which each of the adherent patient devices comprises a unique device identifier;
transmitting the patient data from the at least one adherent device with the wireless communication circuitry to at least one gateway, wherein the at least one gateway comprises a list of unique adherent device identifiers and wherein the at least one gateway comprises a plurality of wireless communication gateways each having a unique gateway identifier and the list of unique adherent device identifiers; and transmitting the patient data and unique gateway identifier from the at least one gateway to a local processor system, wherein a location of the patient is determined in response to the unique adherent device identifier and the unique gateway identifier when the patient is ambulatory.

49. The method of claim 48 wherein the local processor system is configured to send customized alerts in response to the patient data.

50. The method of claim 48 the patient data are transmitted with wireless communication from the at least one gateway to a local processor system.

51. The method of claim 50 wherein the at least one gateway is carried by the at least one patient.

52. The method of claim 51 wherein the at least one gateway transmits the patient data directly to a transceiver of the local processor system.

53. The method of claim 52 wherein each gateway of the plurality of gateways is configured to communicate with a cellular connection to the transceiver of the local processor system.

54. The method of claim 53 wherein at least one gateway communicates with at least one other gateway a mesh wireless communication protocol, such that the patient data is transmitted indirectly from the gateway to the local processor system via the at least one other gateway.

55. The method of claim 48, further comprising transmitting an emergency notification from one of the at least one adherent patient device in response to the patient operating an emergency notification switch on said adherent patient device to trigger the emergency notification transmission.

56. The method of claim 55, wherein the emergency notification is transmitted to said at least one gateway, the method further comprising transmitting the emergency notification from said at least one gateway to said local processor system.

57. The method of claim 56, wherein each adherent patient device comprises a unique device identifier and the patient-initiated emergency notification transmission comprises the unique device identifier, the method further comprising indicating the originating adherent patient device by said local processor system in response to the emergency notification.

58. The method of claim 57, wherein each patient has a unique identifier, the method further comprising indicating by said local processor system in response to the received emergency notification at least one of the unique patient identifier, a name of the patient, an assigned room of the patient, or an assigned bed of the patient.

59. A method of monitoring a plurality of patients, the method comprising:
transmitting first patient data from a first patient measurement device on a first patient to a first gateway with wireless communication;
transmitting the first patient data from the first gateway to a transceiver of a local processor system with a first wireless communication link;
transmitting second patient data from a second patient measurement device on a second patient to a second gateway with wireless communication; and
transmitting the second patient data from the second gateway to the first gateway in response to decoupling of the second gateway with the transceiver.

60. The method of claim 59 wherein the first gateway transmits the second patient data to the transceiver of the local processor system with the first wireless communication link.

61. The method of claim 59 wherein the second gateway is initially coupled directly to the transceiver and is decoupled from the second transceiver in response to movement of the second patient.

62. A system to monitor a plurality of patients, the system comprising:
- a plurality of patient measurement devices configured to measure patient data from a plurality of patients and transmit the patient data;
- a local processor system comprising a tangible medium and at least one display disposed at a monitoring station, the local processor system comprising a transceiver configured to receive the patient data and display the patient data to a user at the monitoring station; and
- a plurality of gateways configured to receive the patient data from the plurality of patient measurement devices, each gateway configured to couple with at least one of the patient measurement devices and transmit the patient data to the local processor system, wherein each of the gateways is configured to couple directly with the transceiver of the processor system when the transceiver is suitable for coupling and to couple with another gateway of the plurality when the transceiver signal is weak.

63. The system of claim 62 wherein the transceiver of the local processor system is configured for placement at the monitoring station.

* * * * *